(12) United States Patent
Fujita

(10) Patent No.: US 10,398,329 B2
(45) Date of Patent: Sep. 3, 2019

(54) BIOLOGICAL STATE ANALYZER AND COMPUTER PROGRAM

(71) Applicant: DELTA TOOLING CO., LTD., Hiroshima-shi (JP)

(72) Inventor: Etsunori Fujita, Hiroshima (JP)

(73) Assignee: DELTA TOOLING CO., LTD., Hiroshima-shi (JP)

( * ) Notice: Subject to any disclaimer, the term of this patent is extended or adjusted under 35 U.S.C. 154(b) by 784 days.

(21) Appl. No.: 14/407,813

(22) PCT Filed: May 30, 2013

(86) PCT No.: PCT/JP2013/065097
§ 371 (c)(1),
(2) Date: Dec. 12, 2014

(87) PCT Pub. No.: WO2013/187243
PCT Pub. Date: Dec. 19, 2013

(65) Prior Publication Data
US 2015/0182141 A1    Jul. 2, 2015

(30) Foreign Application Priority Data
Jun. 16, 2012 (JP) .................... 2012-136460

(51) Int. Cl.
*A61B 5/00* (2006.01)
*A61B 5/18* (2006.01)
(Continued)

(52) U.S. Cl.
CPC ........ *A61B 5/02444* (2013.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS 3,434,151 A * 3/1969 Bader .................. A61B 5/044
346/107.1
4,676,253 A * 6/1987 Newman .............. A61B 5/029
600/506
(Continued)

FOREIGN PATENT DOCUMENTS

JP   2007-7075    1/2007
JP   2010-046236  3/2010
(Continued)

OTHER PUBLICATIONS

Nitzan et al.,The difference in pulse transit time to the toe and finger measured by photoplethysmography, Physiol. Meas. 23 (2002) 85-93.*

(Continued)

*Primary Examiner* — Tiffany Weston
*Assistant Examiner* — Jay B Shah
(74) *Attorney, Agent, or Firm* — Oblon, McClelland, Maier & Neustadt, L.L.P.

(57) ABSTRACT

A novel technique for analyzing a biological state is provided. A body trunk biological signal (aortic pulse wave) extracted from the back of a body trunk is differentiated twice. By using a resultant second derivative waveform, a waveform component of a maximum amplitude of a low frequency appearing as a result of switch of an amplitude from attenuation to amplification in transition from a contracting phase to a diastolic phase of a ventricle is specified in each period of the second derivative waveform. Inflection points are specified that appear before and after the maximum amplitude waveform component. A biological state is analyzed using information about each of the inflection points. The two inflection points obtained from a reference form of the second derivative waveform of the aortic pulse wave substantially agree in time phase with first heart sound and second heart sound (or an R wave and a T wave in an (Continued)

electrocardiogram) indicating the dynamic state of a cardiovascular system. This enables analysis of a biological state.

6 Claims, 55 Drawing Sheets

(51) Int. Cl.
    *A61B 5/024* (2006.01)
    *A61B 5/0205* (2006.01)
    *A61B 5/0245* (2006.01)
    *A61B 5/11* (2006.01)
    *A61B 5/026* (2006.01)

(52) U.S. Cl.
    CPC .............. *A61B 5/1107* (2013.01); *A61B 5/18* (2013.01); *A61B 5/4035* (2013.01); *A61B 5/6823* (2013.01); *A61B 5/6826* (2013.01); *A61B 5/6893* (2013.01); *A61B 5/7235* (2013.01); *A61B 5/7239* (2013.01); *A61B 5/7275* (2013.01); *A61B 5/0261* (2013.01); *A61B 5/02416* (2013.01); *A61B 5/4809* (2013.01); *A61B 5/6887* (2013.01)

(56) References Cited

U.S. PATENT DOCUMENTS

| | | | | |
|---|---|---|---|---|
| 4,802,486 A | * | 2/1989 | Goodman | .......... A61B 5/02416 600/324 |
| 2002/0002339 A1 | * | 1/2002 | Sugo | ................. A61B 5/02125 600/485 |
| 2006/0247542 A1 | | 11/2006 | Watanabe et al. | |
| 2007/0016085 A1 | | 1/2007 | Inukai et al. | |
| 2013/0030256 A1 | | 1/2013 | Fujita et al. | |

FOREIGN PATENT DOCUMENTS

| | | | | |
|---|---|---|---|---|
| JP | 2010046236 A | * | 3/2010 | ............. A61B 5/113 |
| JP | 2011-167362 | | 9/2011 | |
| WO | 2005/000119 | | 1/2005 | |
| WO | 2010/021227 | | 2/2010 | |
| WO | 2010/021228 | | 2/2010 | |

OTHER PUBLICATIONS

Takazawa et al., Assessment of Vasoactive Agents and Vascular Aging by the Second Derivative of Photoplethysmogram Waveform, Hypertension. 1998;32:365-370.*
International Search Report dated Jul. 23, 2013 in PCT/JP13/065097 Filed May 30, 2013.

* cited by examiner (a) SEATED POSTURE   (b) LAYING POSTURE

Fig. 9
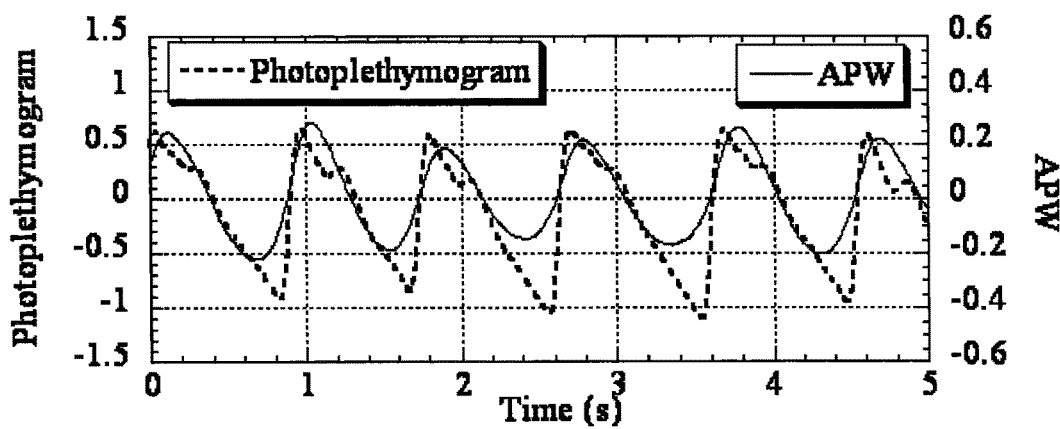
(a) TIME-SERIES WAVEFORM
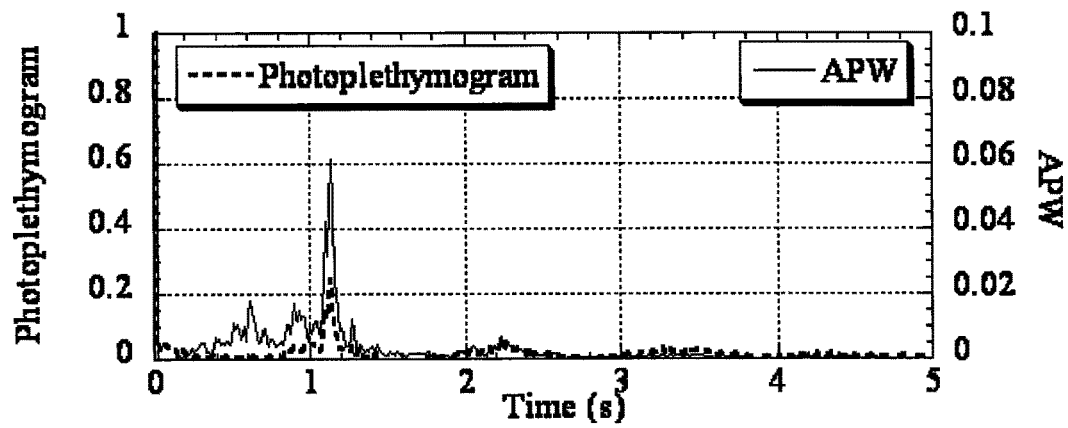
(b) FREQUENCY ANALYSIS RESULT

Fig. 24

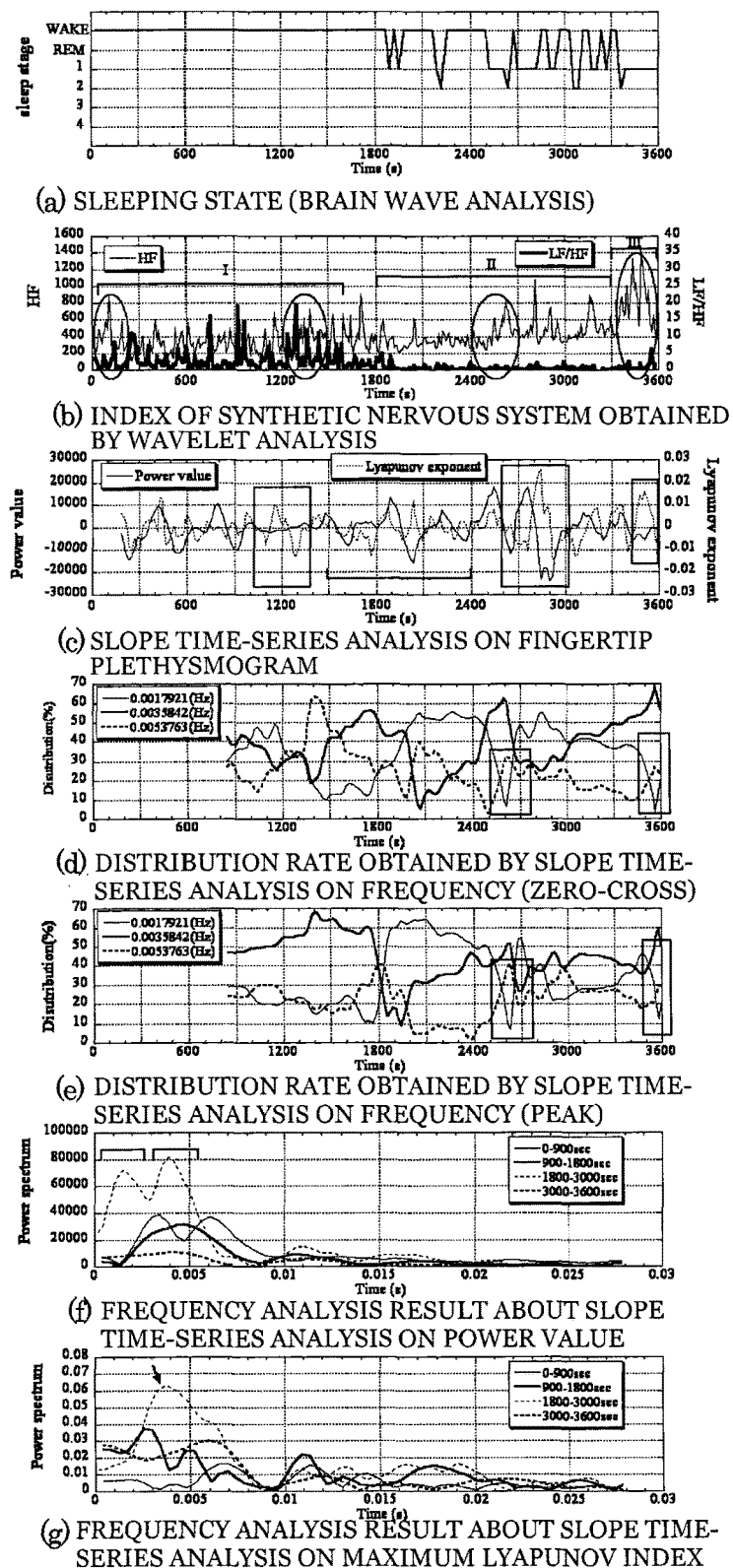

(a) SLEEPING STATE (BRAIN WAVE ANALYSIS)

(b) INDEX OF SYNTHETIC NERVOUS SYSTEM OBTAINED BY WAVELET ANALYSIS (c) SLOPE TIME-SERIES ANALYSIS ON FINGERTIP PLETHYSMOGRAM (d) DISTRIBUTION RATE OBTAINED BY SLOPE TIME-SERIES ANALYSIS ON FREQUENCY (ZERO-CROSS)

(e) DISTRIBUTION RATE OBTAINED BY SLOPE TIME-SERIES ANALYSIS ON FREQUENCY (PEAK)

(f) FREQUENCY ANALYSIS RESULT ABOUT SLOPE TIME-SERIES ANALYSIS ON POWER VALUE (g) FREQUENCY ANALYSIS RESULT ABOUT SLOPE TIME-SERIES ANALYSIS ON MAXIMUM LYAPUNOV INDEX

Fig. 25

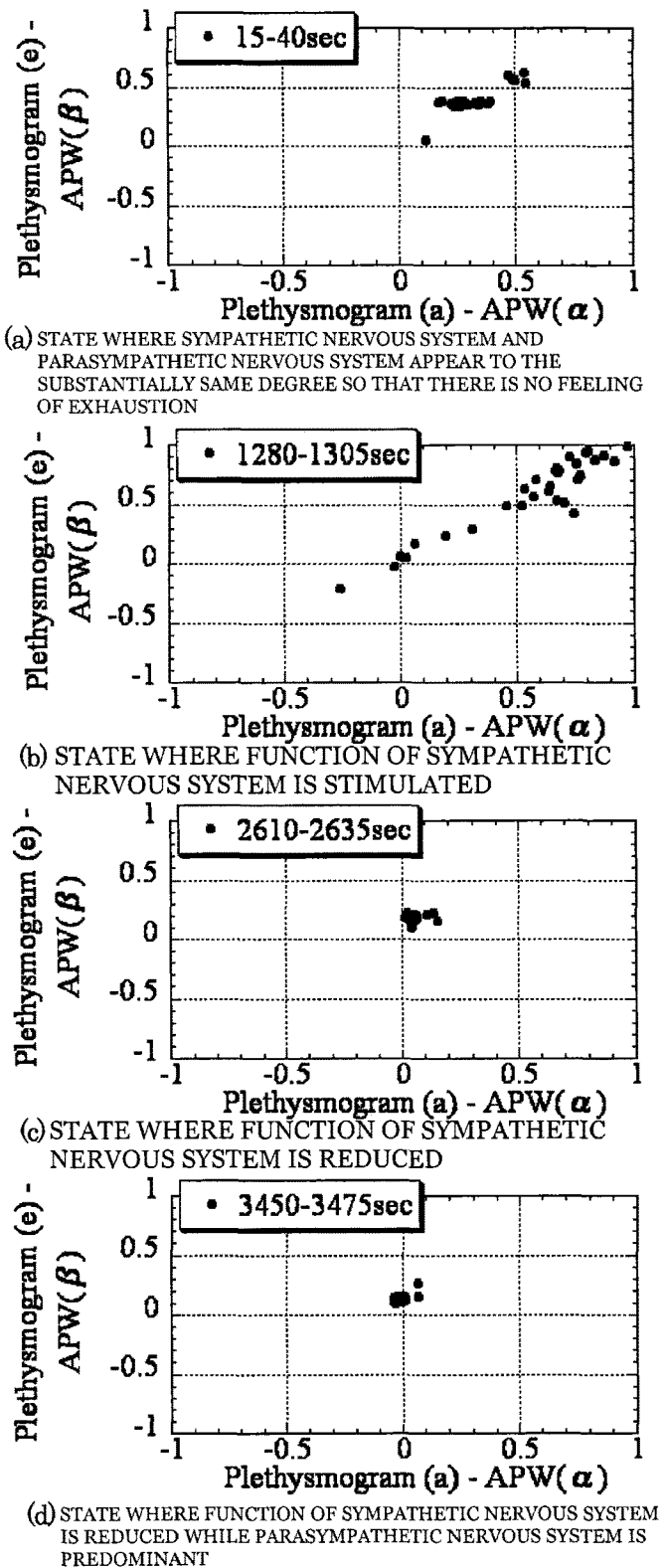

(a) STATE WHERE SYMPATHETIC NERVOUS SYSTEM AND PARASYMPATHETIC NERVOUS SYSTEM APPEAR TO THE SUBSTANTIALLY SAME DEGREE SO THAT THERE IS NO FEELING OF EXHAUSTION (b) STATE WHERE FUNCTION OF SYMPATHETIC NERVOUS SYSTEM IS STIMULATED (c) STATE WHERE FUNCTION OF SYMPATHETIC NERVOUS SYSTEM IS REDUCED (d) STATE WHERE FUNCTION OF SYMPATHETIC NERVOUS SYSTEM IS REDUCED WHILE PARASYMPATHETIC NERVOUS SYSTEM IS PREDOMINANT

Fig. 26
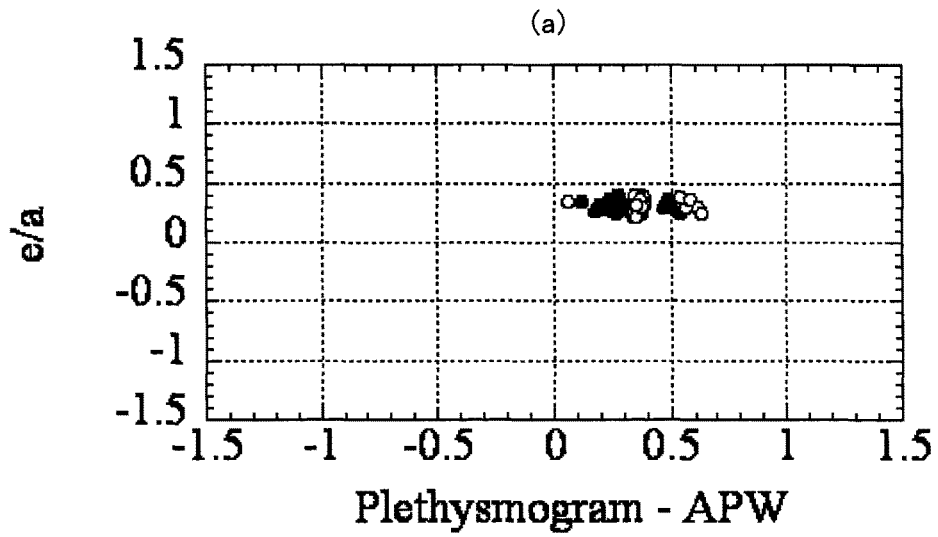
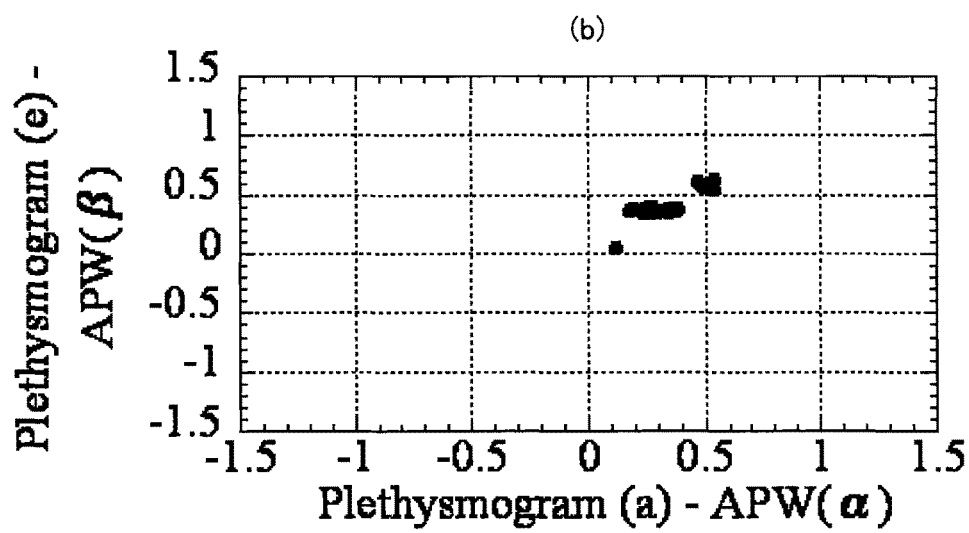

Fig. 27
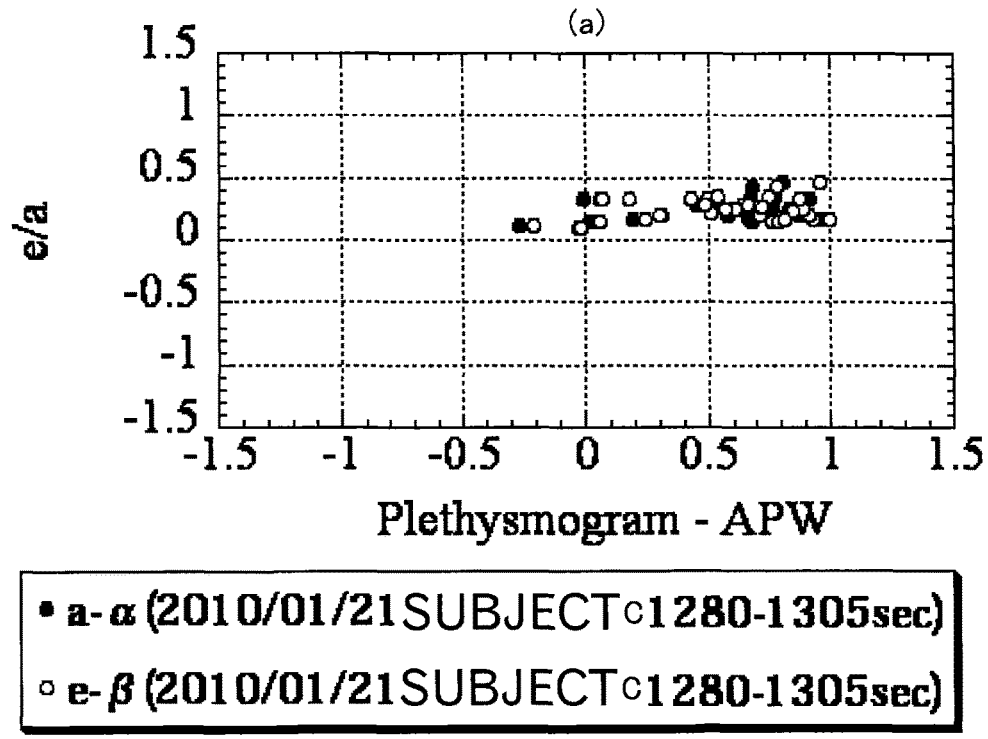
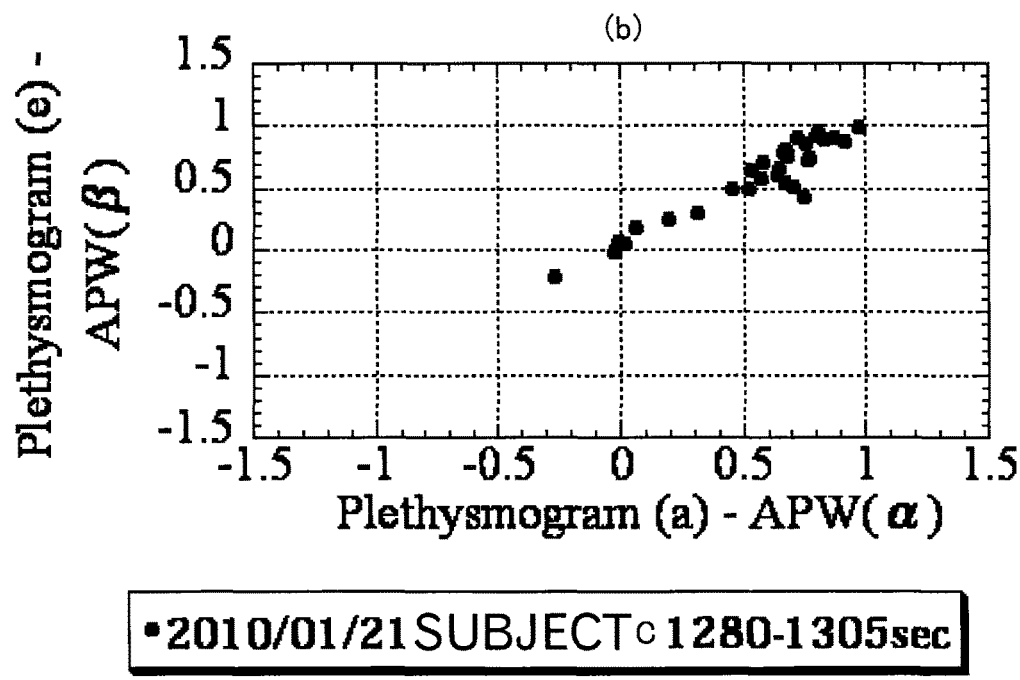

Fig. 28
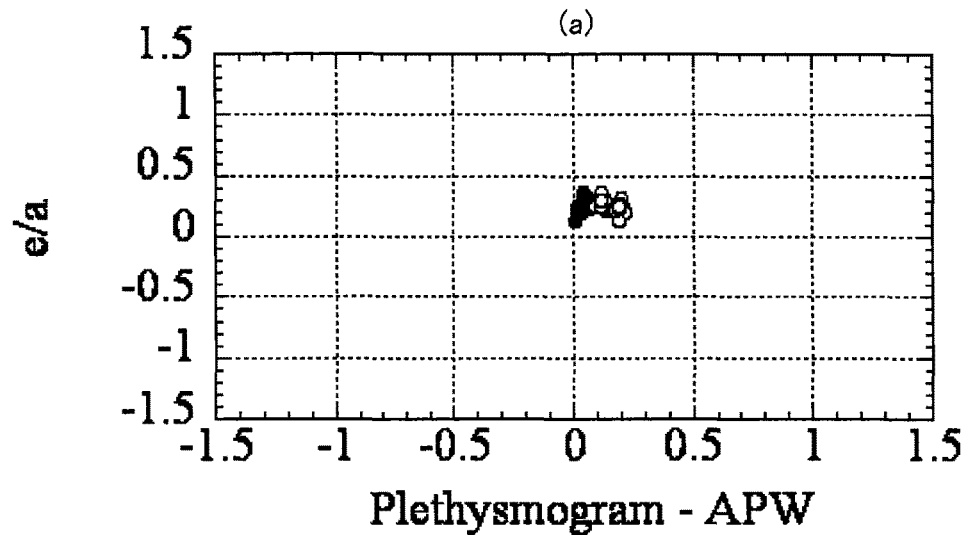
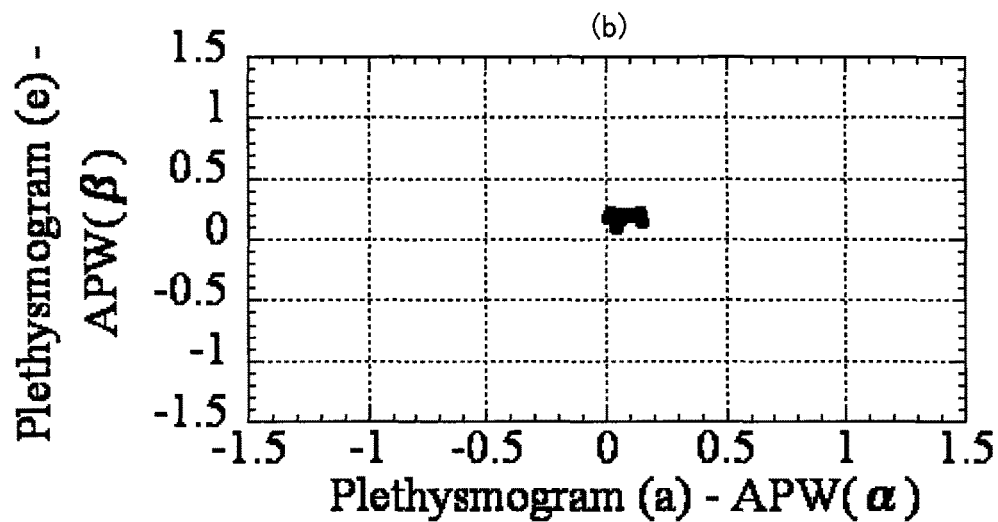

Fig. 29
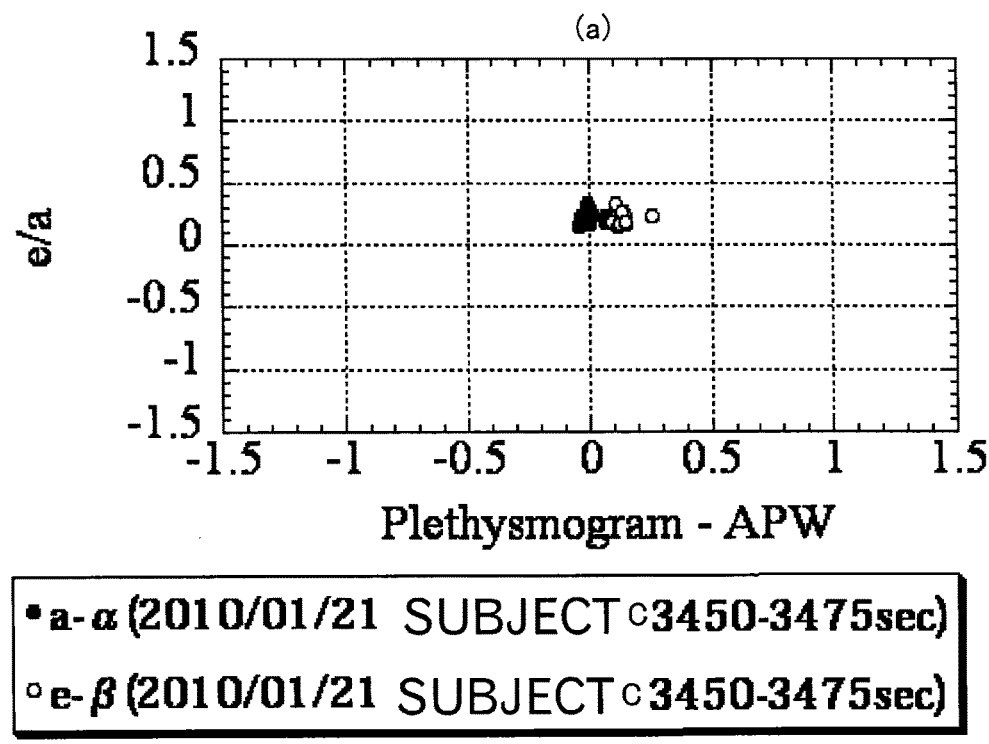
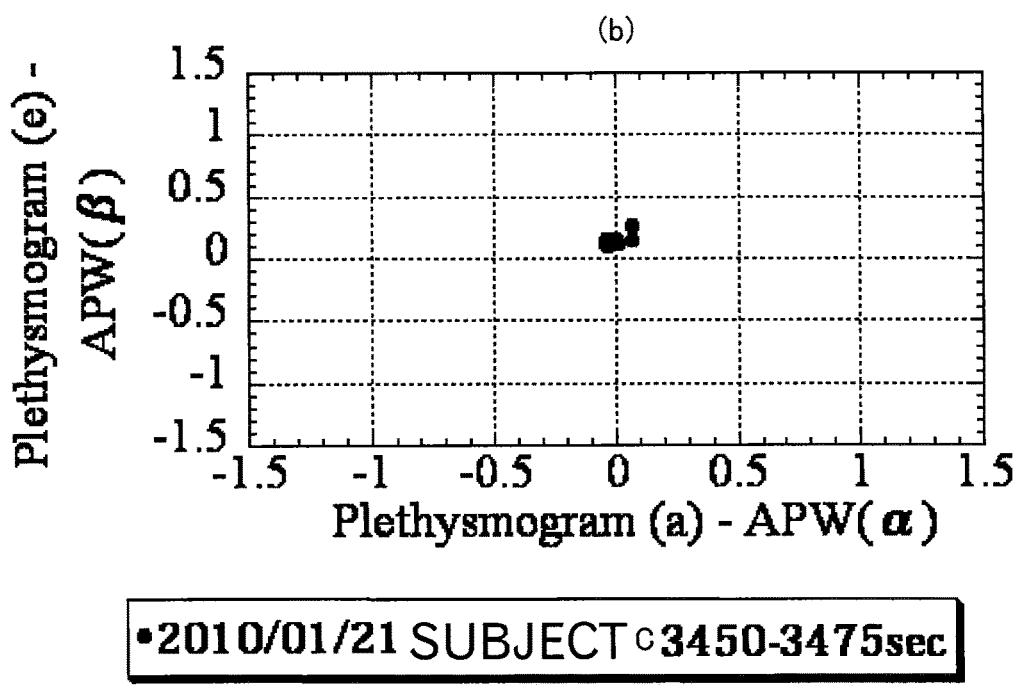

Fig. 30
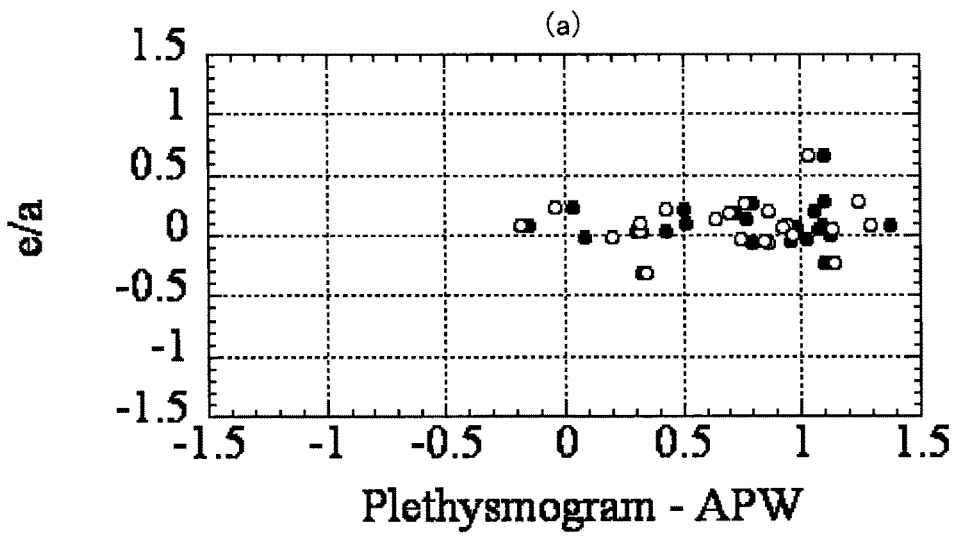
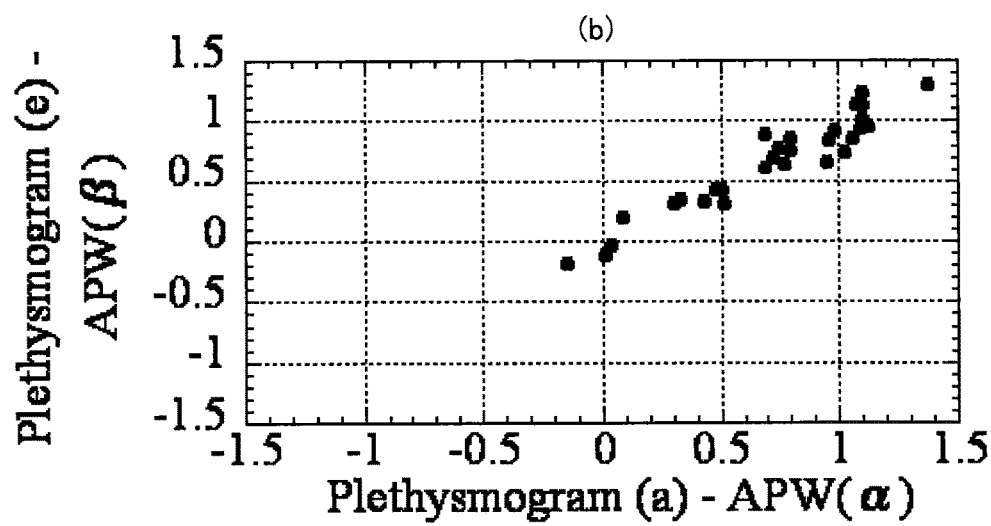

Fig. 31
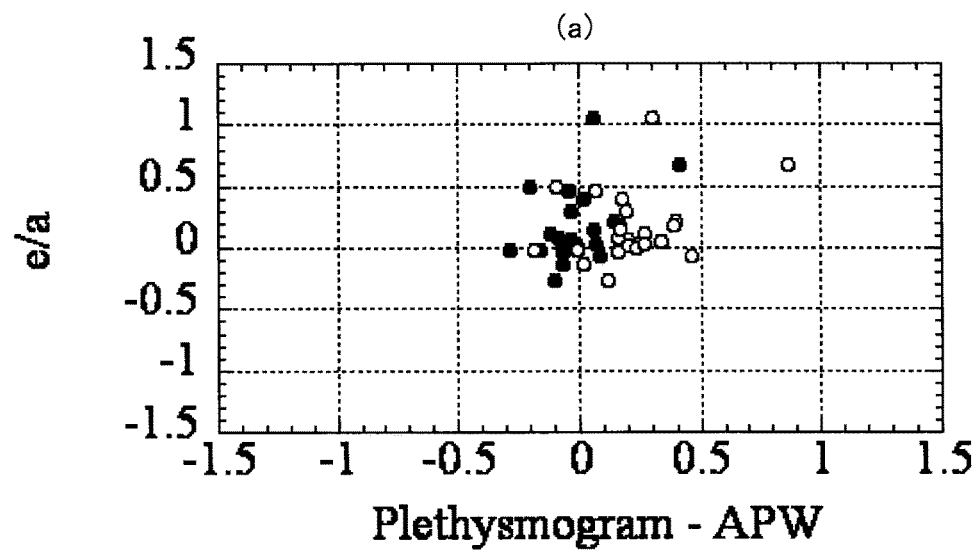
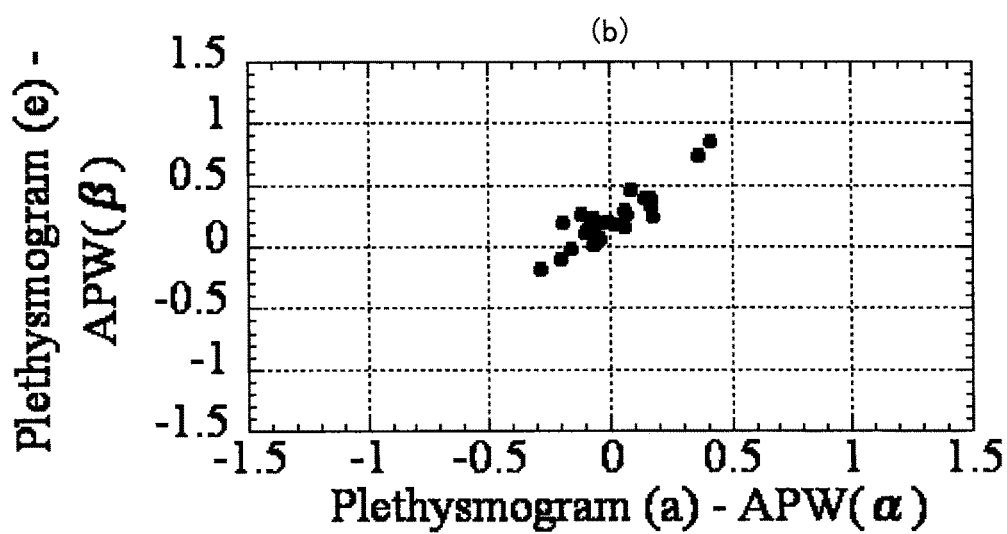

Fig. 32
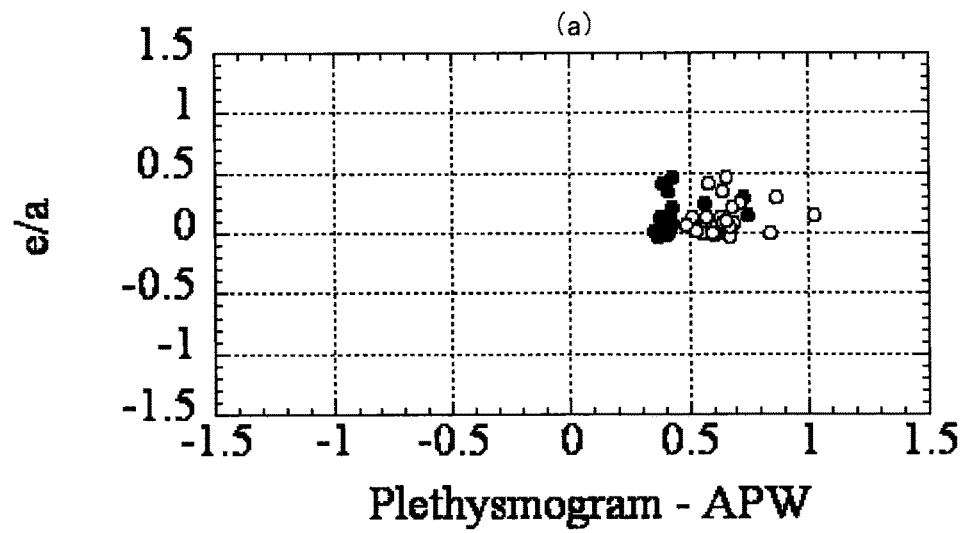
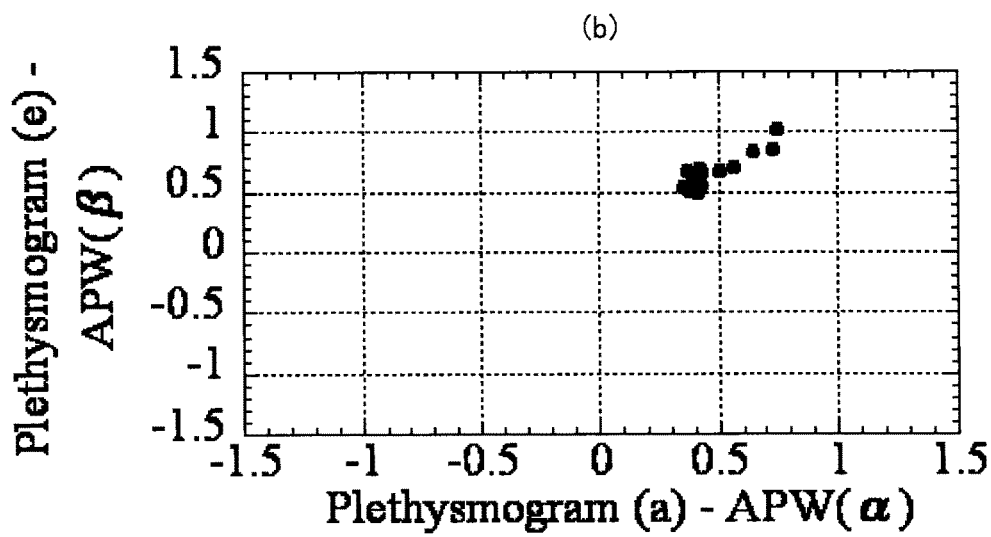

Fig. 33
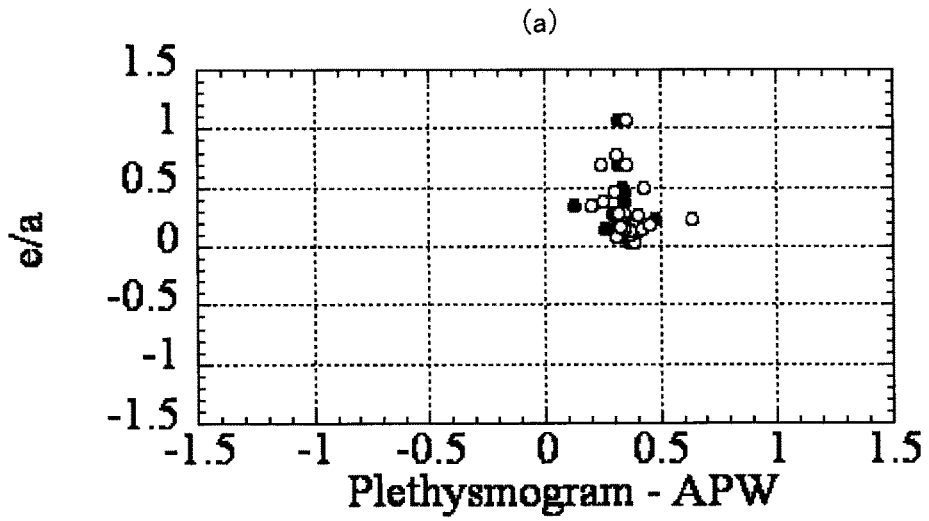
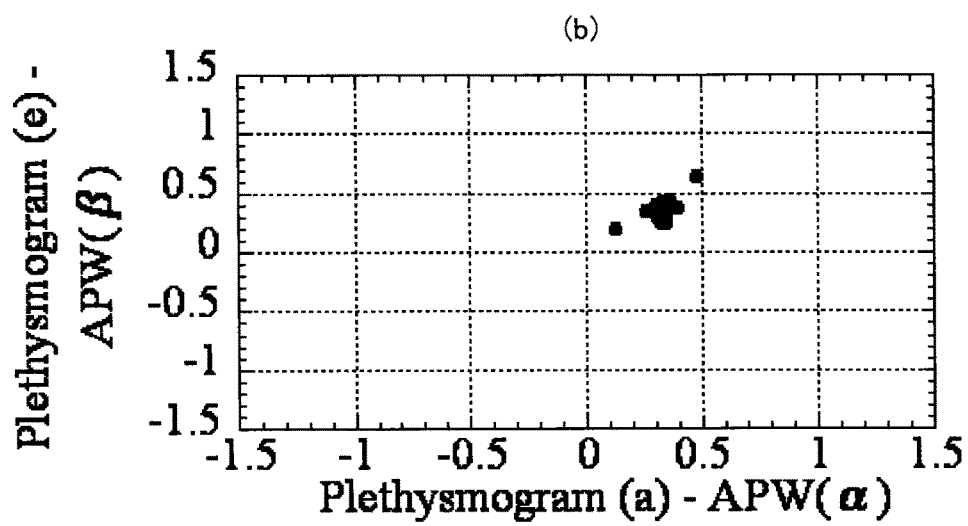

Fig. 34
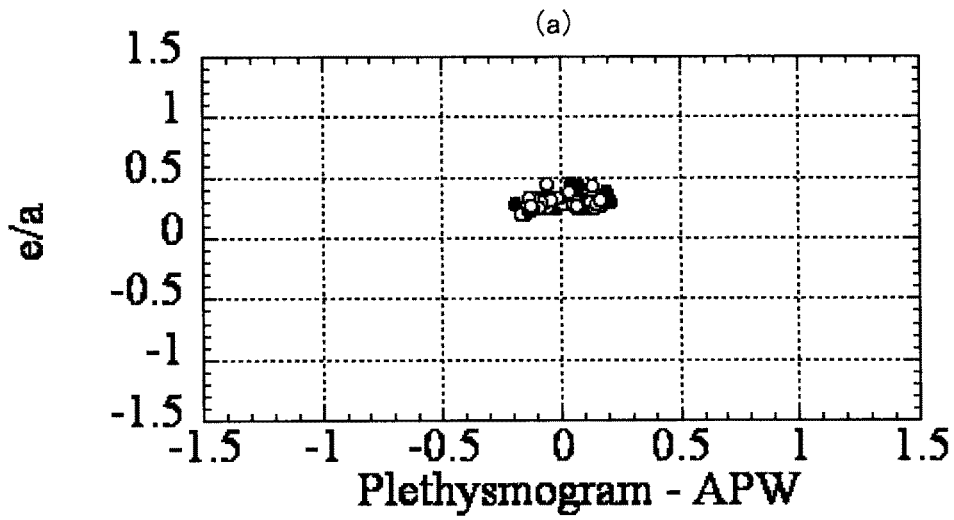
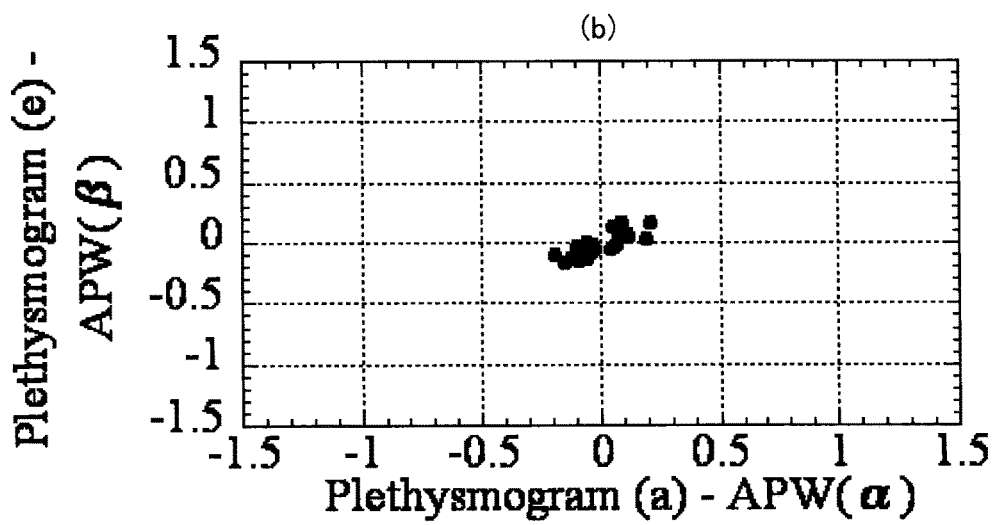

Fig. 35
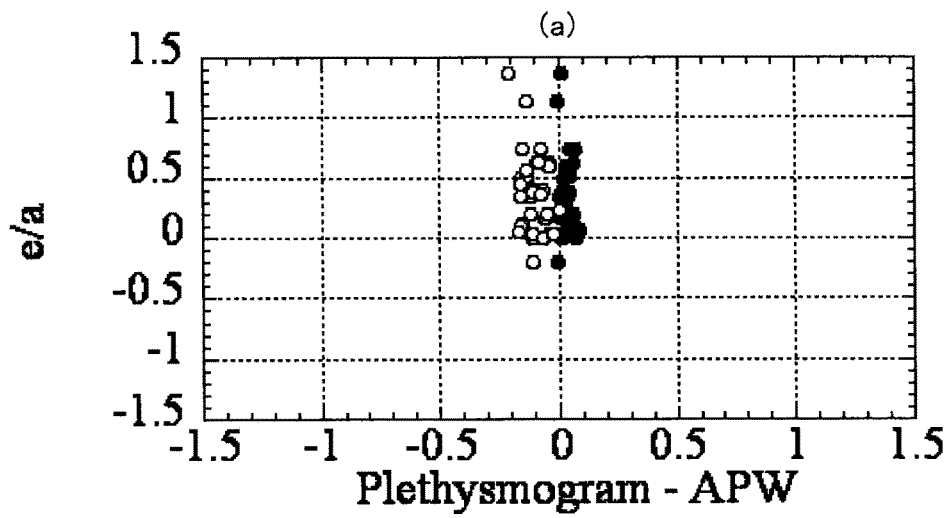
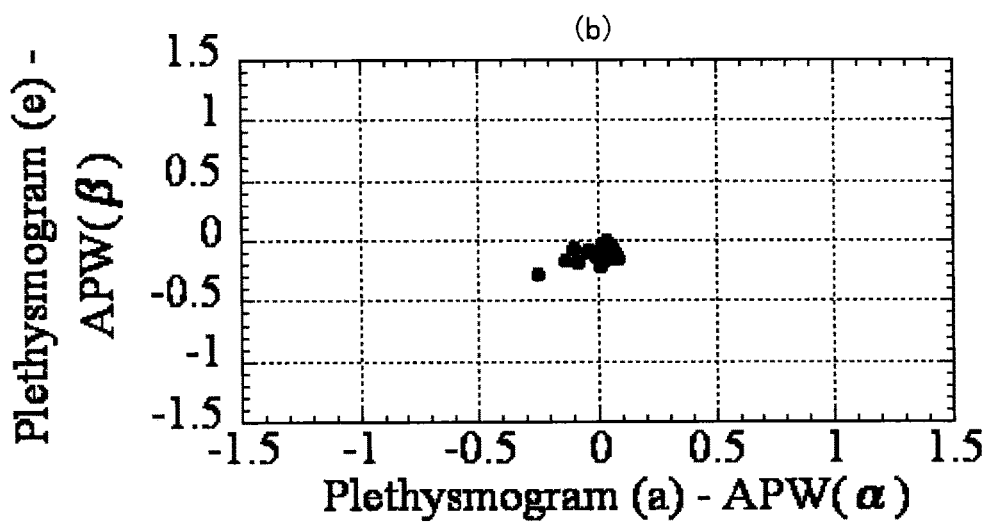

Fig. 43

(a) OUTPUT RESULT (1)

HORIZONTAL AXIS: FINGERTIP (a)
− APW (Eα : ELECTROCARDIOGRAM)
VERTICAL AXIS: e/a (FINGERTIP)

HORIZONTAL AXIS: FINGERTIP (e)
− APW (Eβ : ELECTROCARDIOGRAM)
VERTICAL AXIS: e/a (FINGERTIP)

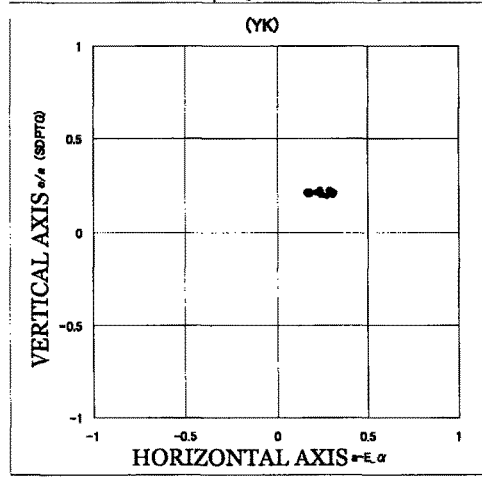
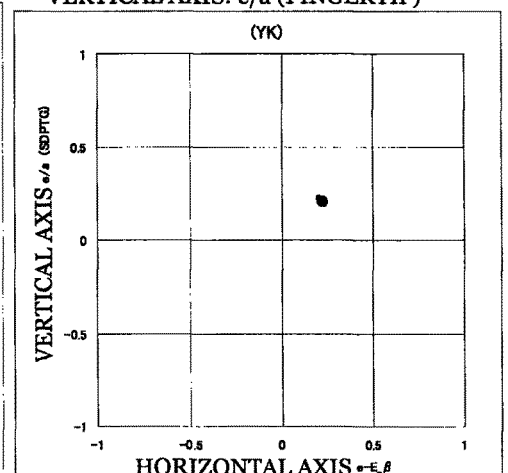

(b) OUTPUT RESULT (2)

HORIZONTAL AXIS: APW (Pα: FINGERTIP)
− APW (Eα: ELECTROCARDIOGRAM)
VERTICAL AXIS: e/a (FINGERTIP)

HORIZONTAL AXIS: APW (Pβ: FINGERTIP)
− APW (Eβ: ELECTROCARDIOGRAM)
VERTICAL AXIS: e/a (FINGERTIP)

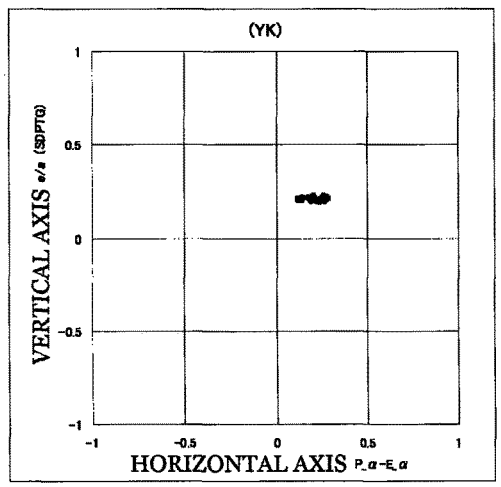
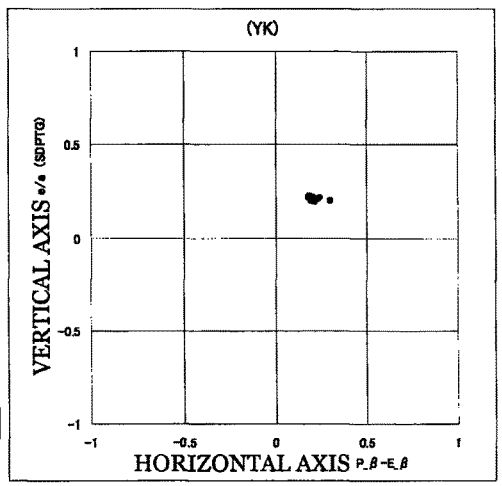

Fig. 46
(a) OUTPUT RESULT (3)
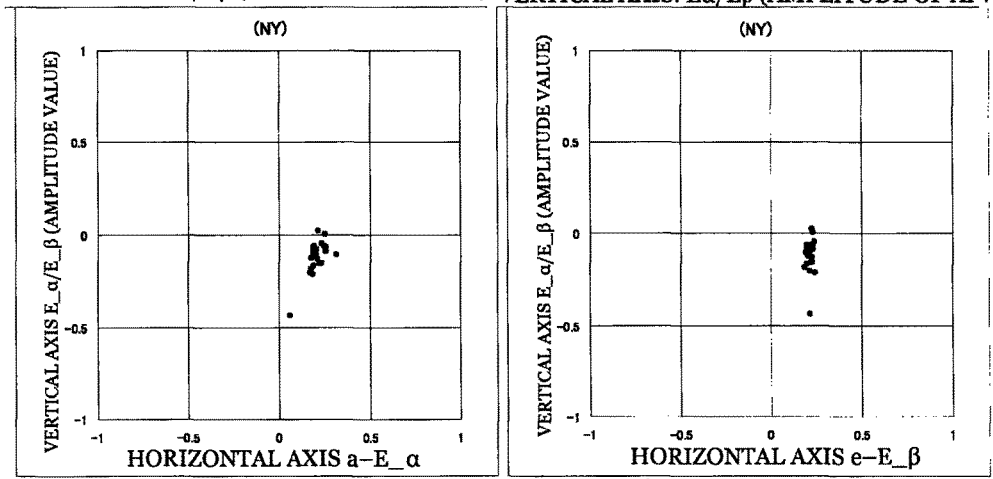
(b) OUTPUT RESULT (4)
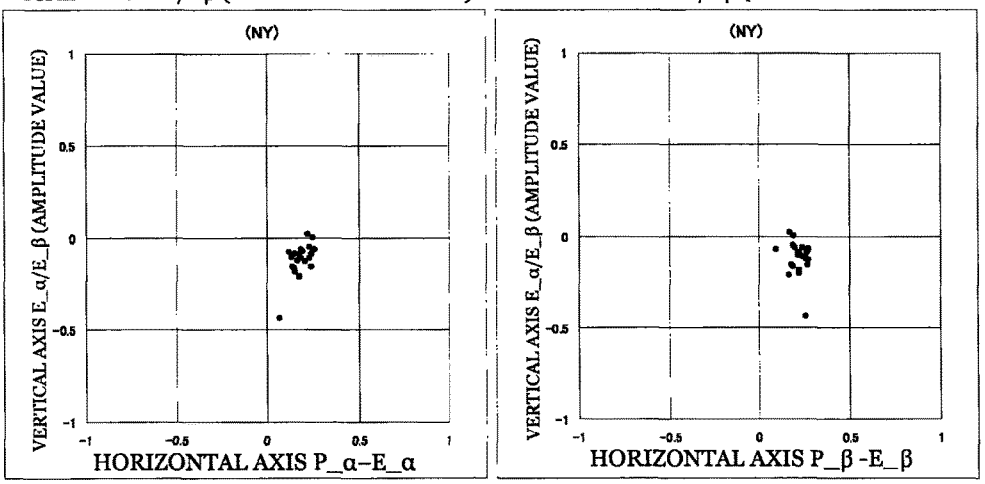

Fig. 48

(a) OUTPUT RESULT (3)

HORIZONTAL AXIS: FINGERTIP (a)
− APW (Eα : ELECTROCARDIOGRAM)
VERTICAL AXIS: Eα/Eβ (AMPLITUDE OF APW)

HORIZONTAL AXIS: FINGERTIP (e)
− APW (Eβ : ELECTROCARDIOGRAM)
VERTICAL AXIS: Eα/Eβ (AMPLITUDE OF APW)

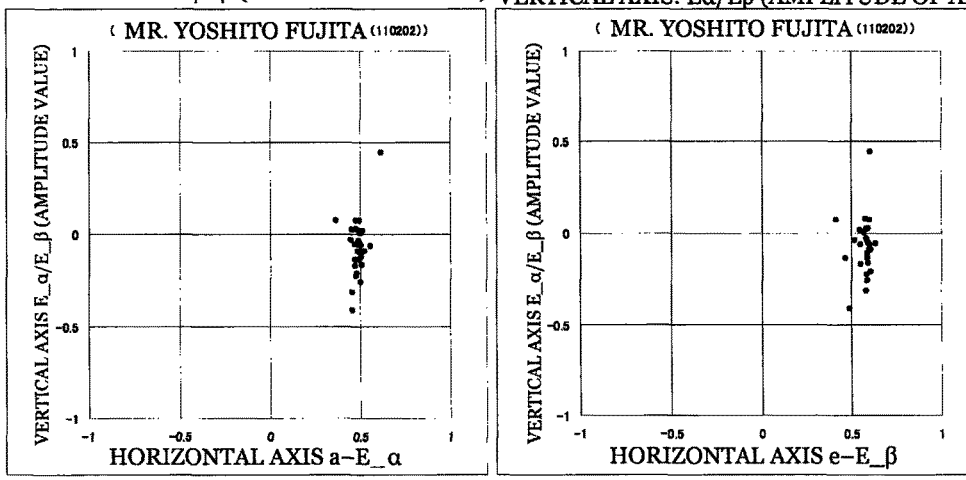

(b) OUTPUT RESULT (4)

HORIZONTAL AXIS: APW (Pα: FINGERTIP)
− APW (Eα : ELECTROCARDIOGRAM)
VERTICAL AXIS: Eα/Eβ (AMPLITUDE OF APW)

HORIZONTAL AXIS: APW (Pβ: FINGERTIP)
− APW (Eβ : ELECTROCARDIOGRAM)
VERTICAL AXIS: Eα/Eβ (AMPLITUDE OF APW)

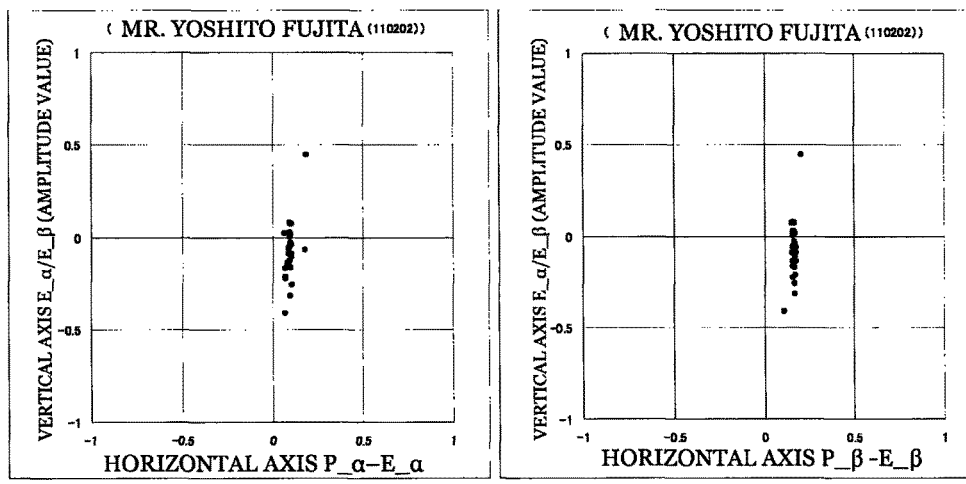

Fig. 50

(a) OUTPUT RESULT (3)

HORIZONTAL AXIS: FINGERTIP (a) − APW (Eα : ELECTROCARDIOGRAM) VERTICAL AXIS: Eα/Eβ (AMPLITUDE OF APW)

HORIZONTAL AXIS: FINGERTIP (e) − APW (Eβ : ELECTROCARDIOGRAM) VERTICAL AXIS: Eα/Eβ (AMPLITUDE OF APW)

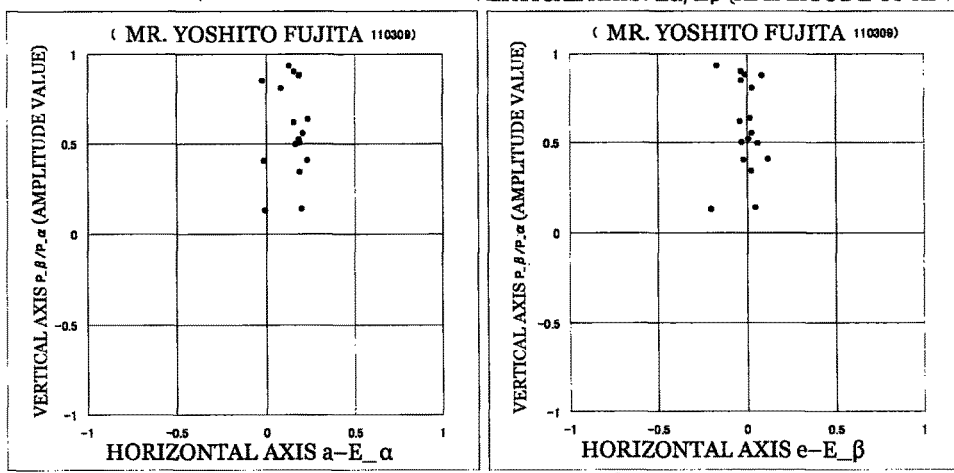

(b) OUTPUT RESULT (4)

HORIZONTAL AXIS: APW (Pα: FINGERTIP) − APW (Eα : ELECTROCARDIOGRAM) VERTICAL AXIS: Eα/Eβ (AMPLITUDE OF APW)

HORIZONTAL AXIS: APW (Pβ: FINGERTIP) − APW (Eβ : ELECTROCARDIOGRAM) VERTICAL AXIS: Eα/Eβ (AMPLITUDE OF APW)

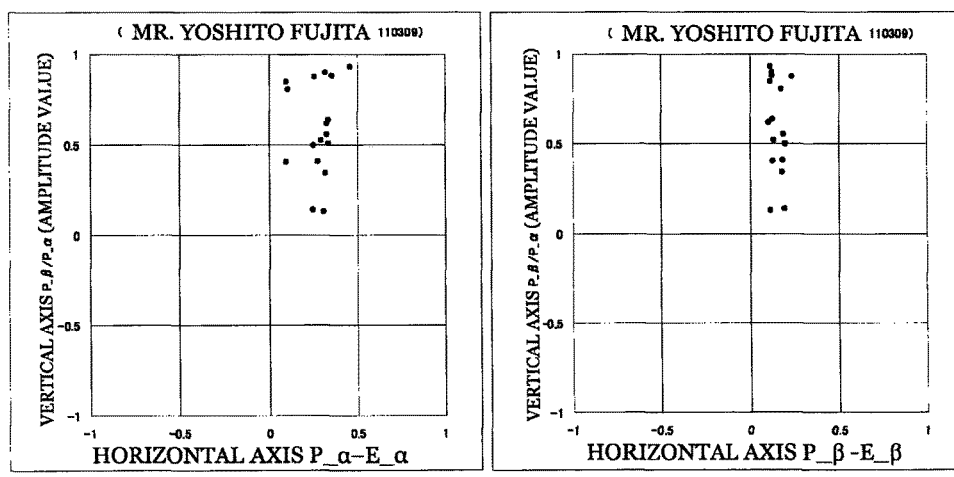

Fig. 51
(a) OUTPUT RESULT (1)
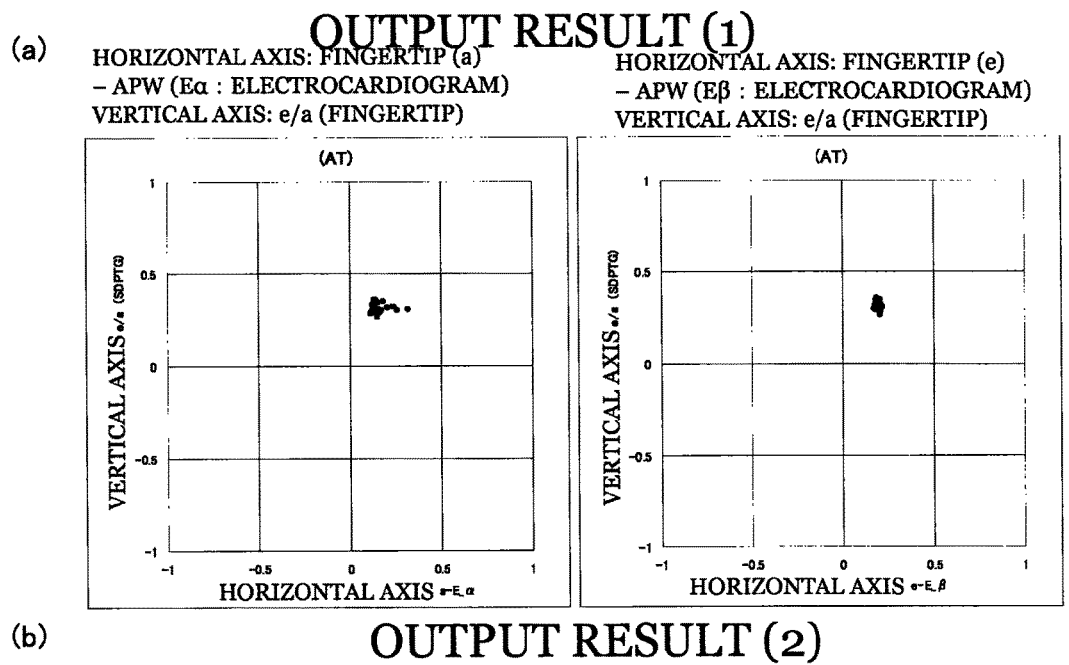
(b) OUTPUT RESULT (2)
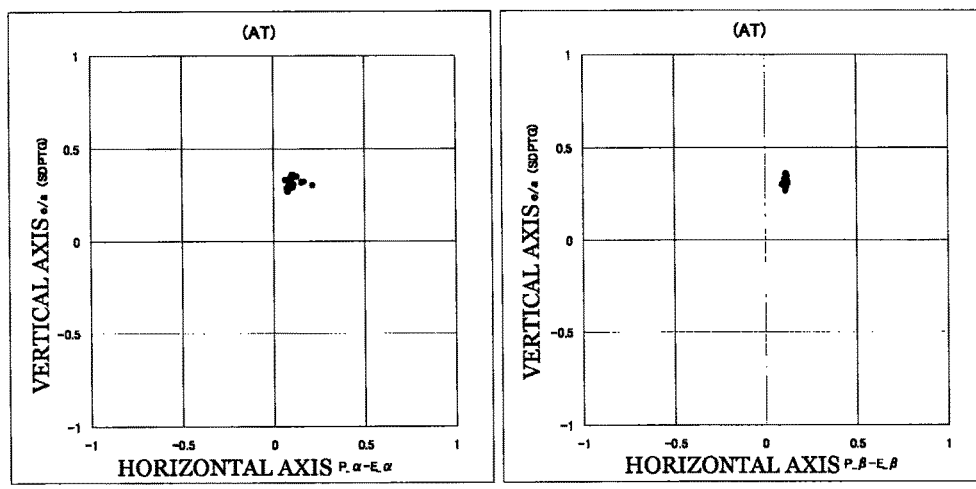

Fig. 54

(a) OUTPUT RESULT (3)

HORIZONTAL AXIS: FINGERTIP (a)
– APW (Eα : ELECTROCARDIOGRAM)
VERTICAL AXIS: Eα/Eβ (AMPLITUDE OF APW)

HORIZONTAL AXIS: FINGERTIP (e)
– APW (Eβ : ELECTROCARDIOGRAM)
VERTICAL AXIS: Eα/Eβ (AMPLITUDE OF APW)

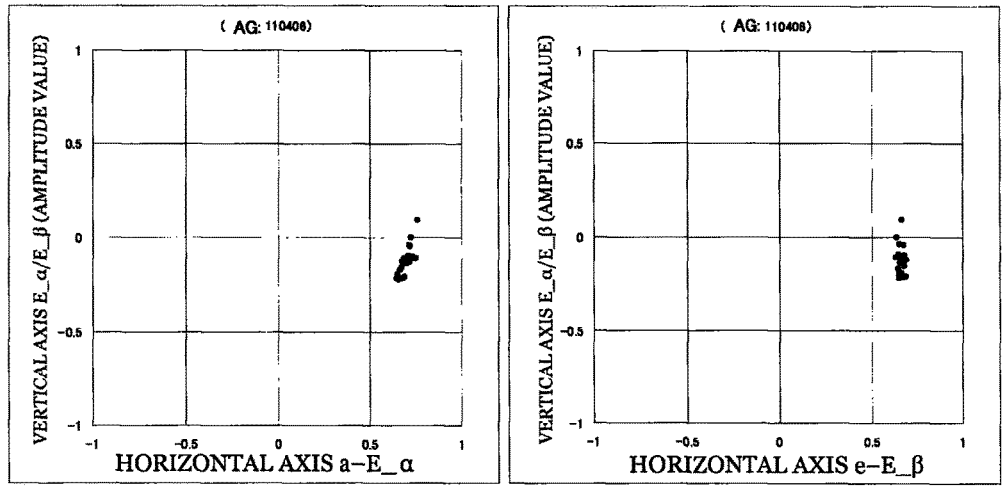

(b) OUTPUT RESULT (4)

HORIZONTAL AXIS: APW (Pα: FINGERTIP)
– APW (Eα : ELECTROCARDIOGRAM)
VERTICAL AXIS: Eα/Eβ (AMPLITUDE OF APW)

HORIZONTAL AXIS: APW (Pβ: FINGERTIP)
– APW (Eβ : ELECTROCARDIOGRAM)
VERTICAL AXIS: Eα/Eβ (AMPLITUDE OF APW)

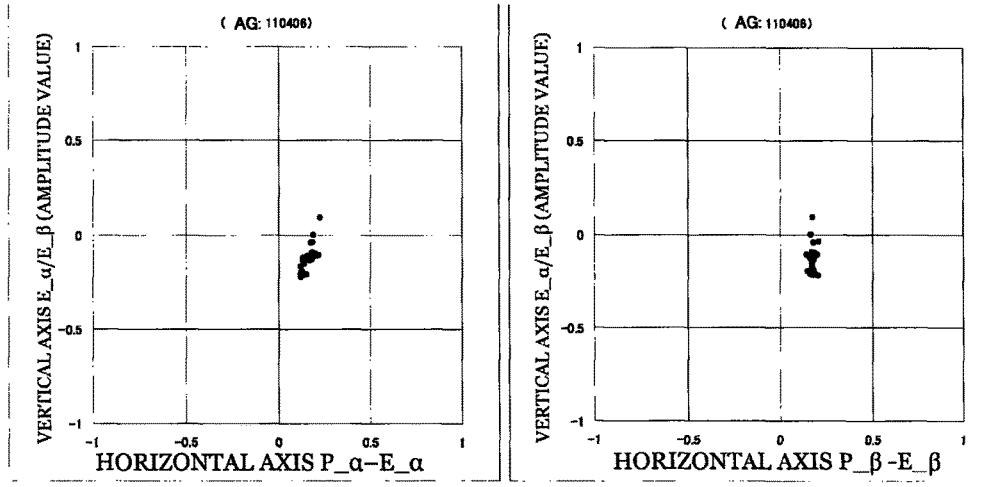

Fig. 55
(a) OUTPUT RESULT (1)
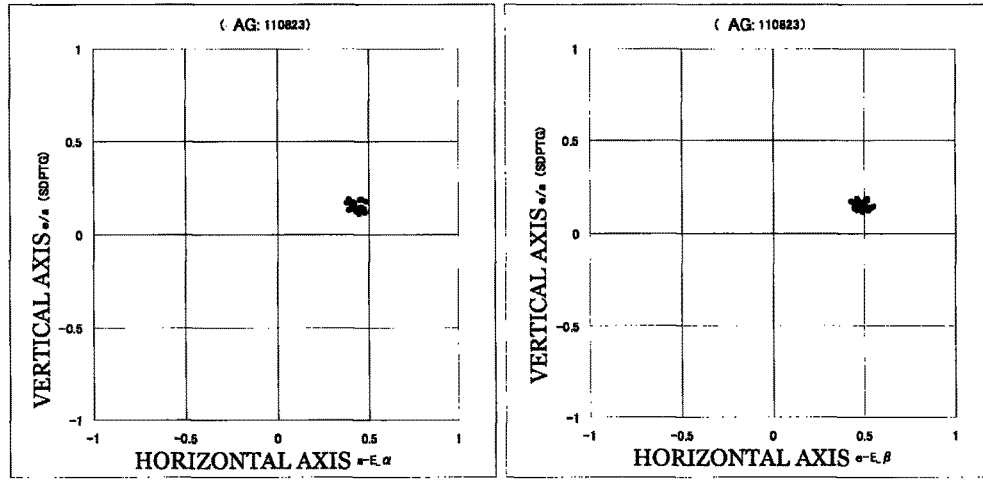
(b) OUTPUT RESULT (2)
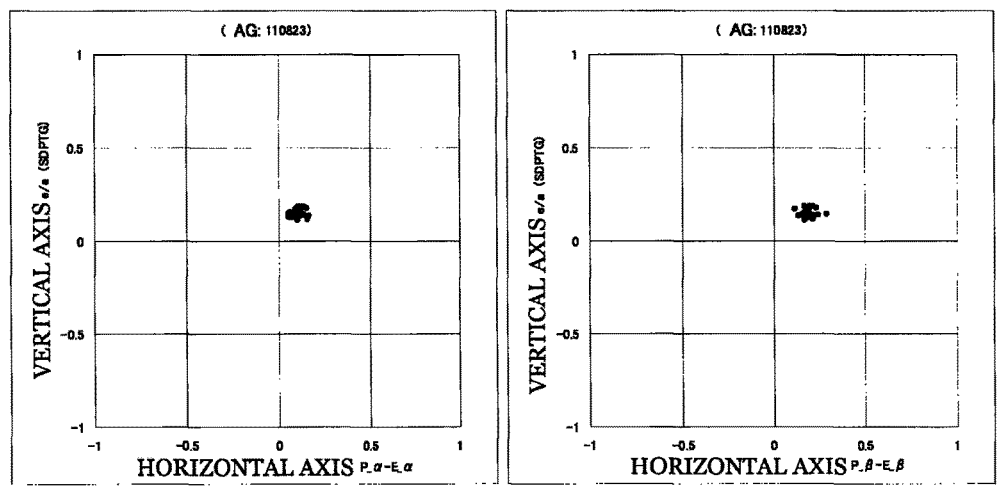

Fig. 56

(a) OUTPUT RESULT (3)

HORIZONTAL AXIS: FINGERTIP (a)  HORIZONTAL AXIS: FINGERTIP (e)
− APW (Eα : ELECTROCARDIOGRAM)  − APW (Eβ : ELECTROCARDIOGRAM)
VERTICAL AXIS: Eα/Eβ (AMPLITUDE OF APW)  VERTICAL AXIS: Eα/Eβ (AMPLITUDE OF APW)

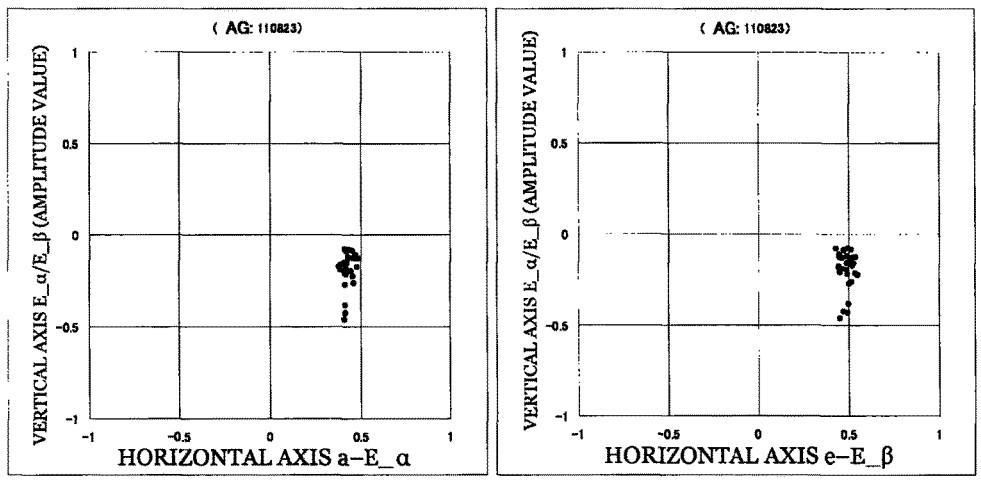

(b) OUTPUT RESULT (4)

HORIZONTAL AXIS: APW (Pα: FINGERTIP)  HORIZONTAL AXIS: APW (Pβ: FINGERTIP)
− APW (Eα : ELECTROCARDIOGRAM)  − APW (Eβ : ELECTROCARDIOGRAM)
VERTICAL AXIS: Eα/Eβ (AMPLITUDE OF APW)  VERTICAL AXIS: Eα/Eβ (AMPLITUDE OF APW)

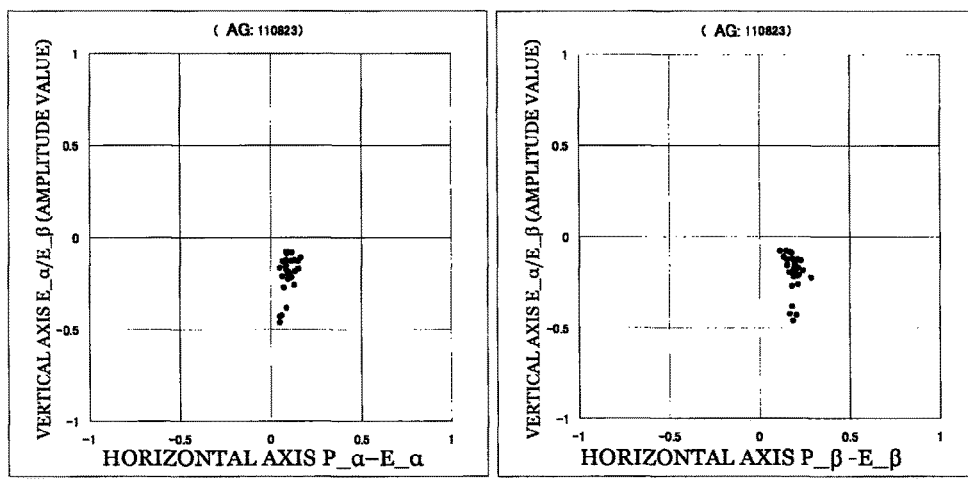

Fig. 57
(a) OUTPUT RESULT (1)
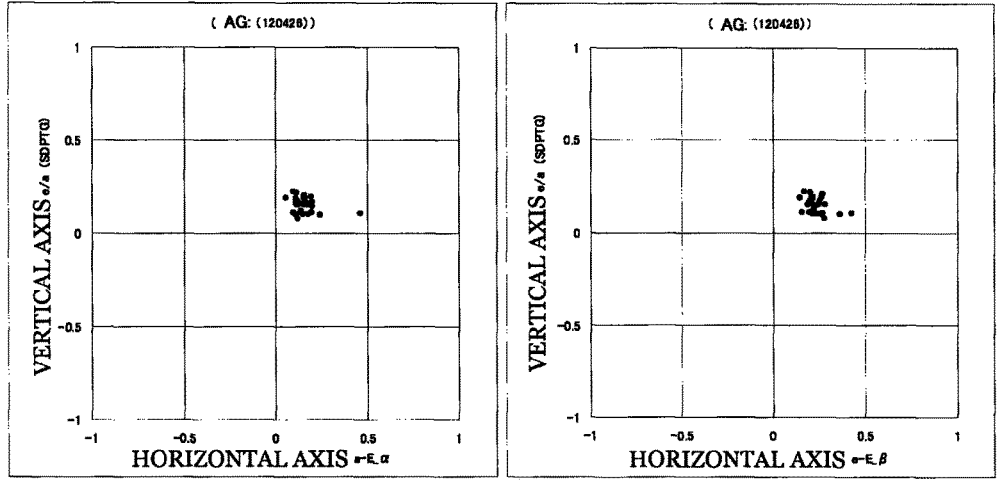
(b) OUTPUT RESULT (2)
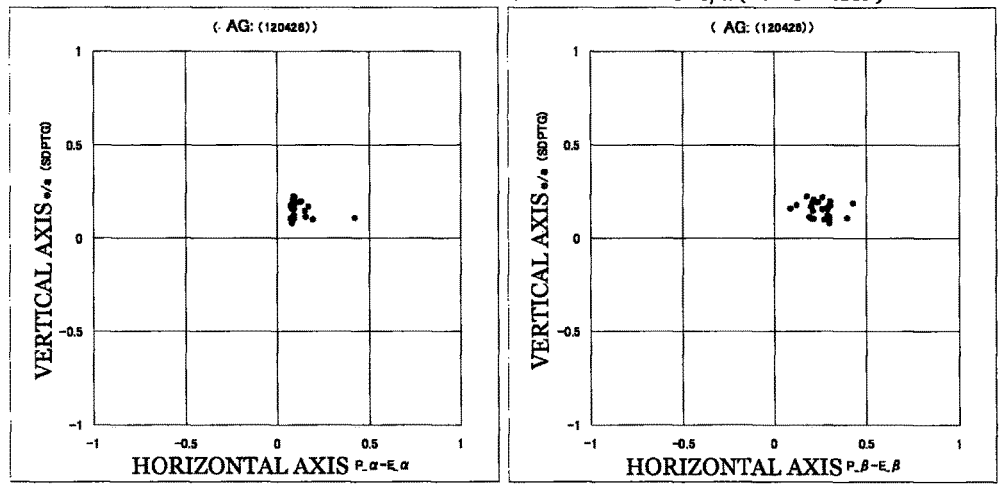

BIOLOGICAL STATE ANALYZER AND COMPUTER PROGRAM

TECHNICAL FIELD

This invention relates to a biological state analyzer and a computer program that analyze the state of a human being using a biological signal extracted from an upper part of a human being.

BACKGROUND ART

A device disclosed in patent literature 1 by the applicant of this application has a procedure of obtaining a time-series waveform of a frequency from a time-series waveform of a biological signal mainly indicating the pulsation of a cardiovascular system, obtaining a time-series waveform of a frequency slope and a time-series waveform of frequency fluctuation, and applying frequency analysis to these waveforms. During the frequency analysis, a power spectrum of a frequency is obtained that corresponds to each of a functional adjustment signal, a fatigue reception signal, and an activity adjustment signal determined in advance is obtained. Then, the state of a human being is determined based on time-series change in each power spectrum. The fatigue reception signal indicates a degree of progress of fatigue in a usual active state. Thus, by comparing this degree with respective degrees of predominance of the functional adjustment signal and the activity adjustment signal as their distribution rates, the state of a human being (such as a relaxed state, a fatigued state, a state where sympathetic nerves are predominant, or a state where parasympathetic nerves are predominant) can be determined more precisely.

According to a technique disclosed in patent literature 2 by the applicant of this application, a biological signal extracted from an air cushion to support the lumbar and its vicinity of a human being is differentiated twice to catch a sleep prediction signal more precisely. According to a technique disclosed in Patent literature 3, a biological signal extracted from an air cushion to support the lumbar and its vicinity is also differentiated twice and an acceleration pulse wave aging index is obtained using a resultant second derivative waveform, thereby determining the presence or absence of alcohol drinking.

CITATION LIST

Patent Literature

Patent Literature 1: Japanese Unexamined Patent Application Publication No. 2011-167362
Patent Literature 2: Japanese Unexamined Patent Application Publication No. 2010-46236
Patent Literature 3: Publication of WO 2010/021228

SUMMARY OF INVENTION

Technical Problems

All the aforementioned techniques are to detect oscillation generated on a surface at the back of a body trunk in an upper part of a human being. A pulse wave (body trunk biological signal) corresponding to this oscillation generated on the surface of the back of the body trunk is pressure oscillation resulting from motion of a heart and an aorta (hereinafter called an "aortic pulse wave (APW)." This aortic pulse wave contains information about the contracting phase and the diastolic phase of a ventricle and elasticity information about a vascular wall functioning as an auxiliary pump for circulation. A signal waveform accompanying heart rate variability contains nervous activity information about a sympathetic nervous system and a parasympathetic nervous system (activity information about a parasympathetic nervous system including the action of compensating for sympathetic nerves). A signal waveform accompanying fluctuation of an aorta contains information about the activity of sympathetic nerves. Thus, by comparing an analysis result about an inspection target obtained in some time period with an analysis result obtained in an earlier time period or with an analysis result obtained in normal times, change in a state such as sleep prediction or alcohol drinking can be grasped.

The present inventor investigated the aforementioned techniques more deeply and found association between a second derivative waveform of a body trunk biological signal (aortic pulse wave) extracted from the back of a body trunk and heart sound (or an electrocardiogram). The present inventor further found new knowledge about association between a second derivative waveform of the aortic pulse wave and a fingertip plethysmogram. It is an object of this invention to provide anew technique for analyzing a biological state based on such new knowledge.

Solution to Problem

In order to solve the aforementioned problem, a biological state analyzer of this invention includes:

body trunk second derivative waveform calculating means that differentiates a time-series waveform of a body trunk biological signal twice extracted from the back of a body trunk by a body trunk biological signal measuring device to obtain a second derivative waveform in a time-series manner;

maximum amplitude waveform component specifying means that specifies a waveform component of a maximum amplitude of a low frequency appearing as a result of switch of an amplitude from attenuation to amplification in transition from a contracting phase to a diastolic phase of a ventricle using the second derivative waveform obtained in a time-series manner by the body trunk second derivative waveform calculating means, the maximum amplitude waveform component being specified in each period of the second derivative waveform;

inflection point specifying means that specifies inflection points appearing before and after the maximum amplitude waveform component specified by the maximum amplitude waveform component specifying means; and state analyzing means that analyzes a biological state using information about each of the inflection points specified by the inflection point specifying means.

Preferably, the inflection point specifying means specifies an inflection point where an amplitude switches from attenuation to amplification as a ventricle initial contracting phase responsive wave (E$\alpha$ wave) and specifies an inflection point where the amplitude switches from amplification to attenuation as a ventricle initial diastolic phase responsive wave (E$\beta$ wave), or the inflection point specifying means specifies an inflection point where an amplitude switches from attenuation to amplification as a fingertip initial contracting phase responsive wave (P$\alpha$ wave) and specifies an inflection point where the amplitude switches from amplification to attenuation as a fingertip initial diastolic phase responsive wave (P$\beta$ wave). The E$\alpha$ and E$\beta$ waves are arranged in this order along a temporal axis with the maximum amplitude waveform component placed in therebetween. The Pα and Pβ waves are arranged in this order along the temporal axis with the maximum amplitude waveform component placed in therebetween.

Preferably, the maximum amplitude waveform component specifying means includes at least one of first maximum amplitude waveform component specifying means and second maximum amplitude waveform component specifying means. The first maximum amplitude waveform component specifying means specifies the maximum amplitude waveform component using a reference form of the second derivative waveform obtained in a time-series manner by the body trunk second derivative waveform calculating means. The second maximum amplitude waveform component specifying means specifies the maximum amplitude waveform component by using an inverted form of the reference form used by the first maximum amplitude waveform component specifying means, the inverted form being generated by inverting the reference form relative to a base line of the reference form.

Preferably, the first maximum amplitude waveform component specifying means is used as the maximum amplitude waveform component specifying means, and the inflection point specifying means specifies the ventricle initial contracting phase responsive wave (Eα wave) and the ventricle initial diastolic phase responsive wave (Eβ wave) that are arranged in this order along the temporal axis with the maximum amplitude waveform component placed in therebetween that is obtained by the first maximum amplitude waveform component specifying means and specified in the reference form of the second derivative waveform.

Preferably, the second maximum amplitude waveform component specifying means is used as the maximum amplitude waveform component specifying means, and the inflection point specifying means specifies the fingertip initial contracting phase responsive wave (Pα wave) and the fingertip initial diastolic phase responsive wave (Pβ wave) that are arranged in this order along the temporal axis with the maximum amplitude waveform component placed in therebetween that is obtained by the second maximum amplitude waveform component specifying means and specified in the inverted form of the second derivative waveform.

Preferably, the biological state analyzer further includes peripheral second derivative waveform calculating means that differentiates a time-series waveform of a peripheral biological signal twice extracted from a periphery by a peripheral biological signal measuring device to obtain a second derivative waveform in a time-series manner, wherein the state analyzing means includes means that analyzes a biological state using an initial contracting phase positive wave (a wave) and an initial diastolic phase positive wave (e wave) of the peripheral biological signal obtained from the second derivative waveform obtained by the peripheral second derivative waveform calculating means and using the ventricle initial contracting phase responsive wave (Eα wave) and the ventricle initial diastolic phase responsive wave (Eβ wave) specified by the inflection point specifying means.

Preferably, the state analyzing means includes means that analyzes a biological state using respective time phases of the initial contracting phase positive wave (a wave) of the peripheral biological signal, the initial diastolic phase positive wave (e wave) of the peripheral biological signal, the ventricle initial contracting phase responsive wave (Eα wave) of the body trunk biological signal, and the ventricle initial diastolic phase responsive wave (Eβ wave) of the body truck biological signal.

Preferably, the state analyzing means includes time phase difference analyzing means that analyzes the state of a sympathetic nervous system using a time phase difference of heart-to-fingertip propagation time (a–Eα) between the initial contracting phase positive wave (a wave) of the peripheral biological signal and the ventricle initial contracting phase responsive wave (Eα wave) of the body trunk biological signal and a using time phase difference of heart-to-fingertip propagation time (e–Eβ) between the initial diastolic phase positive wave (e wave) of the peripheral biological signal and the ventricle initial diastolic phase responsive wave (Eβ wave) of the body trunk biological signal.

Preferably, the time phase difference analyzing means plots coordinate points on a coordinate in association with each period, the coordinate having one axis representing the time phase difference of the heart-to-fingertip propagation time (a–Eα) between the initial contracting phase positive wave (a wave) of the peripheral biological signal and the ventricle initial contracting phase responsive wave (Eα wave) of the body trunk biological signal, and a different axis representing the time phase difference of the heart-to-fingertip propagation time (e–Eβ) between the initial diastolic phase positive wave (e wave) of the peripheral biological signal and the ventricle initial diastolic phase responsive wave (Eβ wave) of the body trunk biological signal.

Preferably, the state analyzing means includes vascular information and time phase difference analyzing means that analyzes a biological state by applying vascular information about a vascular state to at least one of the time phase differences obtained by the time phase difference analyzing means.

Preferably, the vascular information and time phase difference analyzing means of the state analyzing means determines the position of each coordinate point and a degree of dispersion of coordinate points using a wave height ratio (e/a value) as the vascular information between the initial contracting phase positive wave (a wave) and the initial diastolic phase positive wave (e wave) of the peripheral biological signal, thereby estimating the state of stress including the presence or absence of cardiovascular abnormality.

Preferably, the state analyzing means associates the fingertip initial contracting phase responsive wave (Pα wave) and the fingertip initial diastolic phase responsive wave (Pβ wave) obtained by the second maximum amplitude waveform component specifying means with an initial contracting phase positive wave (a wave) and an initial diastolic phase positive wave (e wave) respectively obtained from a second derivative waveform formed by differentiating a time-series waveform of a peripheral biological signal twice extracted from a periphery by a peripheral biological signal measuring device, and the state analyzing means includes means that analyzes a biological state using the fingertip initial contracting phase responsive wave (Pα wave) and the fingertip initial diastolic phase responsive wave (Pβ wave) and the ventricle initial contracting phase responsive wave (Eα wave) and the ventricle initial diastolic phase responsive wave (Eβ wave) specified by the first maximum amplitude waveform component specifying means.

Preferably, the state analyzing means includes means that analyzes a biological state using respective time phases of the fingertip initial contracting phase responsive wave (Pα wave), the fingertip initial diastolic phase responsive wave (Pβ wave), the ventricle initial contracting phase responsive wave (Eα wave), and the ventricle initial diastolic phase responsive wave (Eβ wave).

Preferably, the state analyzing means includes time phase difference analyzing means that analyzes the state of a sympathetic nervous system using a time phase difference of heart-to-fingertip propagation time (Pα–Eα) between the fingertip initial contracting phase responsive wave (Pα wave) and the ventricle initial contracting phase responsive wave (Eα wave) and using a time phase difference of heart-to-fingertip propagation time (Pβ–Eβ) between the fingertip initial diastolic phase responsive wave (Pβ wave) and the ventricle initial diastolic phase responsive wave (Eβ wave).

Preferably, the state analyzing means includes vascular information and time phase difference analyzing means that analyzes a biological state by applying vascular information about a vascular state to at least one of the time phase differences obtained by the time phase difference analyzing means.

Preferably, the vascular information and time phase difference analyzing means of the state analyzing means determines the position of each coordinate point and a degree of dispersion of coordinate points using a ratio as the vascular information between respective amplitudes of inflection points in a pair appearing before and after the maximum amplitude waveform component of the second derivative waveform of the body trunk biological signal specified by the maximum amplitude waveform component specifying means, thereby estimating the state of stress including the presence or absence of cardiovascular abnormality.

Preferably, the state analyzing means includes both of:

vascular information and time phase difference analyzing means that uses a wave height ratio (e/a value) as the vascular information between the initial contracting phase positive wave (a wave) and the initial diastolic phase positive wave (e wave) of the peripheral biological signal; and vascular information and time phase difference analyzing means that uses a ratio as the vascular information between respective amplitudes of inflection points in a pair appearing before and after the maximum amplitude waveform component of the second derivative waveform of the body trunk biological signal specified by the maximum amplitude waveform component specifying means, and the state analyzing means compares two coordinate systems output by the two vascular information and time phase difference analyzing means in terms of the position of each coordinate point and a degree of dispersion of coordinate points, thereby estimating the state of stress including the presence or absence of cardiovascular abnormality.

Preferably, the state analyzing means further includes original waveform comparing and analyzing means that analyzes a biological state by comparing the time-series waveform of the body trunk biological signal received by the body trunk biological signal receiving means and a time-series waveform of a peripheral biological signal extracted from a periphery by a peripheral biological signal measuring device.

Preferably, the original waveform comparing and analyzing means determines the presence or absence of cardiovascular abnormality by comparing the time-series waveform of the body trunk biological signal and the time-series waveform of the peripheral biological signal in frequency and amplitude.

Preferably, a fingertip plethysmogram is used as the peripheral biological signal.

A computer program of this invention makes a computer execute procedures including:

a body trunk second derivative waveform calculating procedure that differentiates a time-series waveform of a body trunk biological signal twice extracted from the back of a body trunk by a body trunk biological signal measuring device to obtain a second derivative waveform in a time-series manner;

a maximum amplitude waveform component specifying procedure that specifies a waveform component of a maximum amplitude of a low frequency appearing as a result of switch of an amplitude from attenuation to amplification in transition from a contracting phase to a diastolic phase of a ventricle using the second derivative waveform obtained in a time-series manner by the body trunk second derivative waveform calculating procedure, the maximum amplitude waveform component being specified in each period of the second derivative waveform;

an inflection point specifying procedure that specifies inflection points appearing before and after the maximum amplitude waveform component specified by the maximum amplitude waveform component specifying procedure; and a state analyzing procedure that analyzes a biological state using information about each of the inflection points specified by the inflection point specifying procedure.

Preferably, the inflection point specifying procedure specifies an inflection point where an amplitude switches from attenuation to amplification as a ventricle initial contracting phase responsive wave (Eα wave) and specifies an inflection point where the amplitude switches from amplification to attenuation as a ventricle initial diastolic phase responsive wave (Eβ wave), or the inflection point specifying procedure specifies an inflection point where an amplitude switches from attenuation to amplification as a fingertip initial contracting phase responsive wave (Pα wave) and specifies an inflection point where the amplitude switches from amplification to attenuation as a fingertip initial diastolic phase responsive wave (Pβ wave). The Eα and Eβ waves are arranged in this order along a temporal axis with the maximum amplitude waveform component placed in therebetween. The Pα and Pβ waves are arranged in this order along the temporal axis with the maximum amplitude waveform component placed in therebetween.

Preferably, the maximum amplitude waveform component specifying procedure includes at least one of a first maximum amplitude waveform component specifying procedure and a second maximum amplitude waveform component specifying procedure. The first maximum amplitude waveform component specifying procedure specifies the maximum amplitude waveform component using a reference form of the second derivative waveform obtained in a time-series manner by the body trunk second derivative waveform calculating procedure. The second maximum amplitude waveform component specifying procedure specifies the maximum amplitude waveform component using an inverted form of the reference form used by the first maximum amplitude waveform component specifying procedure, the inverted form being generated by inverting the reference form relative to a base line of the reference form.

Preferably, the first maximum amplitude waveform component specifying procedure is used as the maximum amplitude waveform component specifying procedure, and the inflection point specifying procedure specifies the ventricle initial contracting phase responsive wave (Eα wave) and the ventricle initial diastolic phase responsive wave (Eβ wave) that are arranged in this order along the temporal axis with the maximum amplitude waveform component placed in therebetween that is obtained by the first maximum amplitude waveform component specifying procedure and specified in the reference form of the second derivative waveform.

Preferably, the second maximum amplitude waveform component specifying procedure is used as the maximum amplitude waveform component specifying procedure, and the inflection point specifying procedure specifies the fingertip initial contracting phase responsive wave (Pα wave) and the fingertip initial diastolic phase responsive wave (Pβ wave) that are arranged in this order along the temporal axis with the maximum amplitude waveform component placed in therebetween that is obtained by the second maximum amplitude waveform component specifying procedure and specified in the inverted form of the second derivative waveform.

Preferably, the computer program further includes a peripheral second derivative waveform calculating procedure that differentiates a time-series waveform of a peripheral biological signal twice extracted from a periphery by a peripheral biological signal measuring device to obtain a second derivative waveform in a time-series manner, wherein the state analyzing procedure includes a procedure that analyzes a biological state by using an initial contracting phase positive wave (a wave) and an initial diastolic phase positive wave (e wave) of the peripheral biological signal obtained from the second derivative waveform obtained by the peripheral second derivative waveform calculating procedure and using the ventricle initial contracting phase responsive wave (Eα wave) and the ventricle initial diastolic phase responsive wave (Eβ wave) specified by the inflection point specifying procedure.

Preferably, the state analyzing procedure includes a procedure that analyzes a biological state using respective time phases of the initial contracting phase positive wave (a wave) of the peripheral biological signal, the initial diastolic phase positive wave (e wave) of the peripheral biological signal, the ventricle initial contracting phase responsive wave (Eα wave) of the body trunk biological signal, and the ventricle initial diastolic phase responsive wave (Eβ wave) of the body truck biological signal.

Preferably, the state analyzing procedure includes a time phase difference analyzing procedure that analyzes the state of a sympathetic nervous system using a time phase difference of heart-to-fingertip propagation time (a–Eα) between the initial contracting phase positive wave (a wave) of the peripheral biological signal and the ventricle initial contracting phase responsive wave (Eα wave) of the body trunk biological signal and using a time phase difference of heart-to-fingertip propagation time (e–Eβ) between the initial diastolic phase positive wave (e wave) of the peripheral biological signal and the ventricle initial diastolic phase responsive wave (Eβ wave) of the body trunk biological signal.

Preferably, the time phase difference analyzing procedure plots coordinate points on a coordinate in association with each period, the coordinate having one axis representing the time phase difference of the heart-to-fingertip propagation time (a–Eα) between the initial contracting phase positive wave (a wave) of the peripheral biological signal and the ventricle initial contracting phase responsive wave (Eα wave) of the body trunk biological signal, and a different axis representing the time phase difference of the heart-to-fingertip propagation time (e–Eβ) between the initial diastolic phase positive wave (e wave) of the peripheral biological signal and the ventricle initial diastolic phase responsive wave (Eβ wave) of the body trunk biological signal.

Preferably, the state analyzing procedure includes a vascular information and time phase difference analyzing procedure that analyzes a biological state by applying vascular information about a vascular state to at least one of the time phase differences obtained by the time phase difference analyzing procedure.

Preferably, the vascular information and time phase difference analyzing procedure of the state analyzing procedure determines the position of each coordinate point and a degree of dispersion of coordinate points using a wave height ratio (e/a value) as the vascular information between the initial contracting phase positive wave (a wave) and the initial diastolic phase positive wave (e wave) of the peripheral biological signal, thereby estimating the state of stress including the presence or absence of cardiovascular abnormality.

Preferably, the state analyzing procedure associates the fingertip initial contracting phase responsive wave (Pα wave) and the fingertip initial diastolic phase responsive wave (Pβ wave) obtained by the second maximum amplitude waveform component specifying procedure with an initial contracting phase positive wave (a wave) and an initial diastolic phase positive wave (e wave) respectively obtained from a second derivative waveform formed by differentiating a time-series waveform of a peripheral biological signal twice extracted from a periphery by a peripheral biological signal measuring device, and the state analyzing procedure includes a procedure that analyzes a biological state using the fingertip initial contracting phase responsive wave (Pα wave) and the fingertip initial diastolic phase responsive wave (Pβ wave) and using the ventricle initial contracting phase responsive wave (Eα wave) and the ventricle initial diastolic phase responsive wave (Eβ wave) specified by the first maximum amplitude waveform component specifying procedure.

Preferably, the state analyzing procedure includes a procedure that analyzes a biological state using respective time phases of the fingertip initial contracting phase responsive wave (Pα wave), the fingertip initial diastolic phase responsive wave (Pβ wave), the ventricle initial contracting phase responsive wave (Eα wave), and the ventricle initial diastolic phase responsive wave (Eβ wave).

Preferably, the state analyzing procedure includes a time phase difference analyzing procedure that analyzes the state of a sympathetic nervous system using a time phase difference of heart-to-fingertip propagation time (Pα–Eα) between the fingertip initial contracting phase responsive wave (Pα wave) and the ventricle initial contracting phase responsive wave (Eα wave) and using a time phase difference of heart-to-fingertip propagation time (Pβ–Eβ) between the fingertip initial diastolic phase responsive wave (Pβ wave) and the ventricle initial diastolic phase responsive wave (Eβ wave).

Preferably, the state analyzing procedure includes a vascular information and time phase difference analyzing procedure that analyzes a biological state by applying vascular information about a vascular state to at least one of the time phase differences obtained by the time phase difference analyzing procedure.

Preferably, the vascular information and time phase difference analyzing procedure of the state analyzing procedure determines the position of each coordinate point and a degree of dispersion of coordinate points using a ratio as the vascular information between respective amplitudes of inflection points in a pair appearing before and after the maximum amplitude waveform component of the second derivative waveform of the body trunk biological signal specified by the maximum amplitude waveform component specifying procedure, thereby estimating the state of stress including the presence or absence of cardiovascular abnormality.

Preferably, the state analyzing procedure includes both of:
a vascular information and time phase difference analyzing procedure that uses a wave height ratio (e/a value) as the vascular information between the initial contracting phase positive wave (a wave) and the initial diastolic phase positive wave (e wave) of the peripheral biological signal; and
a vascular information and time phase difference analyzing procedure that uses a ratio as the vascular information between respective amplitudes of inflection points in a pair appearing before and after the maximum amplitude waveform component of the second derivative waveform of the body trunk biological signal specified by the maximum amplitude waveform component specifying procedure, and
the state analyzing procedure compares two coordinate systems output by the two vascular information and time phase difference analyzing procedures in terms of the position of each coordinate point and a degree of dispersion of coordinate points, thereby estimating the state of stress including the presence or absence of cardiovascular abnormality.

Preferably, the state analyzing procedure further includes an original waveform comparing and analyzing procedure that analyzes a biological state by comparing the time-series waveform of the body trunk biological signal received by the body trunk biological signal receiving procedure and a time-series waveform of a peripheral biological signal extracted from a periphery by a peripheral biological signal measuring device.

Preferably, the original waveform comparing and analyzing procedure determines the presence or absence of cardiovascular abnormality by comparing the time-series waveform of the body trunk biological signal and the time-series waveform of the peripheral biological signal in frequency and amplitude.

Preferably, a fingertip plethysmogram is used as the peripheral biological signal.

Advantageous Effects of Invention

In this invention, a body trunk biological signal (aortic pulse wave) extracted from the back of a body trunk is differentiated twice. By using a resultant second derivative waveform, a waveform component of a maximum amplitude of a low frequency appearing as a result of switch of an amplitude from attenuation to amplification in transition from a contracting phase to a diastolic phase of a ventricle is specified in each period of the second derivative waveform. Inflection points are specified that appear before and after the maximum amplitude waveform component. A biological state is analyzed using information about each of the inflection points. The present inventor found that two inflection points obtained from a reference form of the second derivative waveform of the aortic pulse wave substantially agree in time phase with first heart sound and second heart sound (or an R wave and a T wave in an electrocardiogram) indicating the dynamic state of a cardiovascular system. Thus, according to this invention, only by holding a posture that makes the back of a body trunk contact a medical chair, a seat for a vehicle, a bed or the like on which a body trunk biological signal measuring device is installed, the dynamic state of a cardiovascular system can be known without the presence of a stethoscope or a measuring instrument intended for measurement of heart sound or an electrocardiogram. The aforementioned two inflection points (hereinafter called "ventricle initial contracting phase responsive wave (Eα wave)" and "ventricle initial diastolic phase responsive wave (Eβ wave)") are specified by calculating the time-series waveform of the extracted aortic pulse wave. Thus, compared to stethoscopic determination made by a human being, resultant data can be more objective and precise.

As a result of comparison of the aforementioned ventricle initial phase responsive wave and ventricle initial diastolic phase responsive wave in time phase with an initial contracting phase positive wave (a wave) and an initial diastolic phase positive wave (e wave) respectively obtained from an acceleration pulse wave formed by differentiating a fingertip plethysmogram twice, the present inventor found that there are constant shifts therebetween. The present inventor also found that these shifts in time phase change according to the state of a human being (in this invention, this state means various biological states including the state of a sympathetic nervous system, change in a physical state, and the presence or absence or a disease). Thus, by configuring this invention such that the ventricle initial contracting phase responsive wave and the ventricle initial diastolic phase responsive wave are examined in association with the initial contracting phase positive wave (a wave) and the initial diastolic phase positive wave (e wave) of a fingertip plethysmogram, the state of a human being can be determined more precisely.

The present inventor further found that inflection points appearing before and after a waveform component of a maximum amplitude in each period obtained from a form (inverted form) of a second derivative waveform correspond to the initial contracting phase positive wave (a wave) and the initial diastolic phase positive wave (e wave) of a fingertip plethysmogram. The inverted form is generated by inverting the reference form of the second derivative waveform of the aortic pulse wave relative to a base line of the reference form. These inflection points are specified as a fingertip initial contracting phase responsive wave (Pα wave) and a fingertip initial diastolic phase responsive wave (Pβ wave) arranged in this order along a temporal axis. Then, this information is used as an a wave and an e wave of a fingertip plethysmogram. As a result, the state of a human being can be determined only by measuring an aortic pulse wave without measuring a fingertip plethysmogram. Specifically, the aortic pulse wave is information containing both information about a part near the center obtained from heart sound or in an electrocardiogram and information about an output wave reflecting effect caused by the elasticity of a peripheral system superimposed on an input wave starting from a heart (specifically, information to change in frequency properties in response to information about a periphery obtained from a fingertip plethysmogram that is to have the same period and the same fluctuation inherently). Thus, by analyzing a second derivative waveform of an aortic pulse wave in terms of its reference form and its inverted form, two pieces of information including information about a part near the center such as heart sound or an electrocardiogram and information about a fingertip plethysmogram relating to a periphery can be obtained only from information about the aortic pulse wave.

BRIEF DESCRIPTION OF DRAWINGS

FIGS. 9(a) and (b) show a time-series waveform of an aortic pulse wave (APW) as a body trunk biological signal obtained from the body trunk biological signal measuring device and a result of frequency analysis on this time-series waveform respectively.

FIGS. 24(a) to (g) show measurement results obtained in the experiment of FIG. 3 by using various different indexes of sympathetic nerves.

FIGS. 25(a) to (d) show analysis results obtained by using a difference between the time phase of a fingertip plethysmogram and a time phase obtained from a second derivative waveform of a reference form of an APW.

FIG. 26(a) shows an output result by vascular information and time phase difference analyzing means and FIG. 26(b) shows an output result by time phase difference analyzing means that correspond to data (15 to 40 seconds) about a subject C in Example 4.

FIG. 27(a) shows an output result by the vascular information and time phase difference analyzing means and FIG. 27(b) shows an output result by the time phase difference analyzing means that correspond to data (1280 to 1305 seconds) about the subject C in Example 4.

FIG. 28(a) shows an output result by the vascular information and time phase difference analyzing means and FIG. 28(b) shows an output result by the time phase difference analyzing means that correspond to data (2610 to 2635 seconds) about the subject C in Example 4.

FIG. 29(a) shows an output result by the vascular information and time phase difference analyzing means and FIG. 29(b) shows an output result by the time phase difference analyzing means that correspond to data (3450 to 3475 seconds) about the subject C in Example 4.

FIG. 30(a) shows an output result by the vascular information and time phase difference analyzing means and FIG. 30(b) shows an output result by the time phase difference analyzing means that correspond to data (2010, Sep. 30, 15 to 40 seconds) about a subject Y in Example 4.

FIG. 31(a) shows an output result by the vascular information and time phase difference analyzing means and FIG. 31(b) shows an output result by the time phase difference analyzing means that correspond to data (2011, Jan. 21, 15 to 40 seconds) about the subject Y in Example 4.

FIG. 32(a) shows an output result by the vascular information and time phase difference analyzing means and FIG. 32(b) shows an output result by the time phase difference analyzing means that correspond to data (2011, Jul. 17, 15 to 40 seconds) about the subject Y in Example 4.

FIG. 33(a) shows an output result by the vascular information and time phase difference analyzing means and FIG. 33(b) shows an output result by the time phase difference analyzing means that correspond to data (2011, Feb. 2, 15 to 40 seconds) about a subject, Mr. Yoshito Fujita in Example 4.

FIG. 34(a) shows an output result by the vascular information and time phase difference analyzing means and FIG. 34(b) shows an output result by the time phase difference analyzing means that correspond to data (2011, Mar. 9, 15 to 40 seconds) about the subject, Mr. Yoshito Fujita in Example 4.

FIG. 35(a) shows an output result by the vascular information and time phase difference analyzing means and FIG. 35(b) shows an output result by the time phase difference analyzing means that correspond to data (2011, Mar. 21, 15 to 40 seconds) about the subject, Mr. Yoshito Fujita in Example 4.

FIG. 43 shows output results (1) and (2) obtained by the vascular information and time phase difference analyzing means using data about a subject YK.

FIG. 46 shows output results (3) and (4) obtained by the vascular information and time phase difference analyzing means using the data about the subject NY.

FIG. 48 shows output results (3) and (4) obtained by the vascular information and time phase difference analyzing means using the data on 2011, Feb. 2 about the subject, Mr. Yoshito Fujita.

FIG. 50 shows output results (3) and (4) obtained by the vascular information and time phase difference analyzing means using the data on 2011, Mar. 9 about the subject, Mr. Yoshito Fujita.

FIG. 51 shows output results (1) and (2) obtained by the vascular information and time phase difference analyzing means using data about a subject AT.

FIG. 52 shows output results (3) and (4) obtained by the vascular information and time phase difference analyzing means using the data about the subject AT.

FIG. 54 shows output results (3) and (4) obtained by the vascular information and time phase difference analyzing means using the data on 2011, Apr. 6 about the subject AG.

FIG. 55 shows output results (1) and (2) obtained by the vascular information and time phase difference analyzing means using data on 2011, Aug. 23 about the subject AG.

FIG. 56 shows output results (3) and (4) obtained by the vascular information and time phase difference analyzing means using the data on 2011, Aug. 23 about the subject AG.

FIG. 57 shows output results (1) and (2) obtained by the vascular information and time phase difference analyzing means using data on 2012, Apr. 26 about the subject AG.

DESCRIPTION OF EMBODIMENTS

Figure 1:
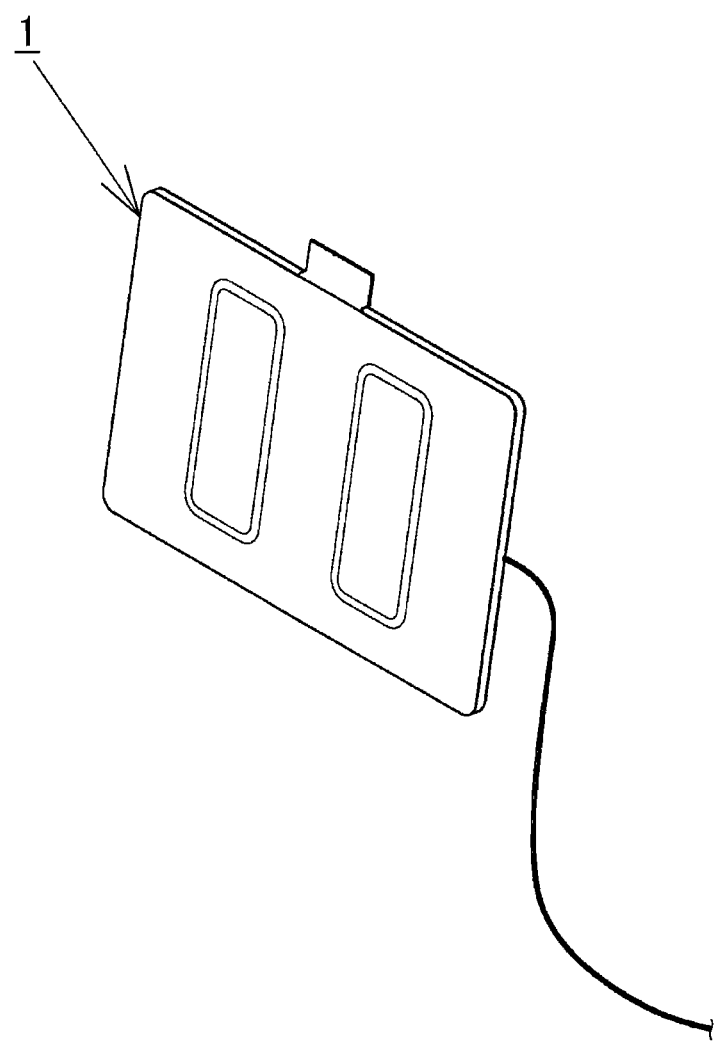
FIG. 1 is a perspective view showing an example of a body trunk biological signal measuring device used in an embodiment of this invention.
Figure 2:
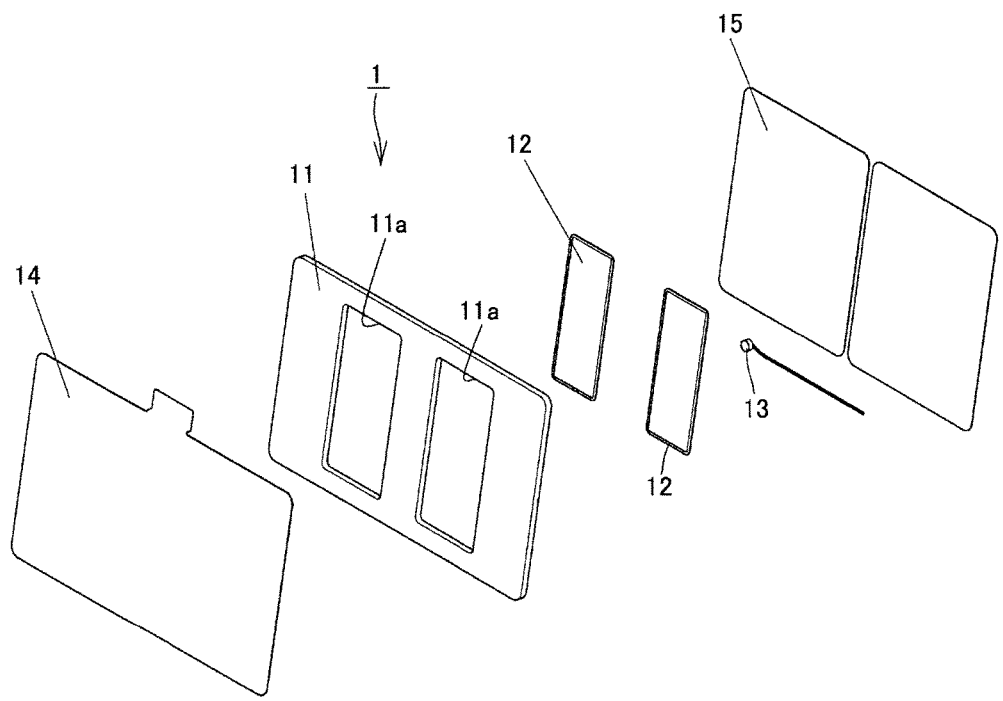
FIG. 2 is an exploded perspective view of the body trunk biological signal measuring device shown in FIG. 1.
Figure 3:
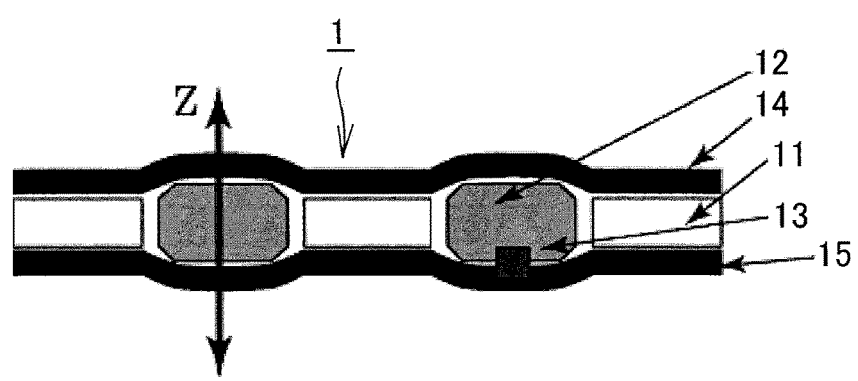
FIG. 3 is a sectional view of a principal part of the body trunk biological signal measuring device shown in FIG. 1.

This invention is described in more detail below based on embodiments of this invention shown in the drawings. FIGS. 1 to 3 show a body trunk biological signal measuring device 1 that extracts a body trunk biological signal from the back of a body trunk, specifically an aortic pulse wave (APW) to be analyzed by a biological state analyzer 60 of an embodiment of this invention. An aortic pulse wave is pressure oscillation resulting from motion of a heart and an aorta detected from the back of the upper part of a human being. The aortic pulse wave contains information about the contracting phase and the diastolic phase of a ventricle and elasticity information about a vessel wall functioning as an auxiliary pump for circulation and by blood pressure. A signal waveform accompanying heart rate variability contains nervous activity information about a sympathetic nervous system and a parasympathetic nervous system (activity information about the parasympathetic nervous system including the action of compensating for sympathetic nerves). A signal waveform accompanying fluctuation of an aorta contains information about the activity of sympathetic nerves.

As shown in FIGS. 2 and 3, the body trunk biological signal measuring device 1 used in this embodiment includes a core pad 11, spacer pads 12, a sensor 13, a front film 14, and a rear film 15.

The core pad 11 is formed into a plate shape, for example. The core pad 11 has two vertically-long through holes 11*a* formed at symmetric positions relative to a part corresponding to a backbone. It is preferable that the core pad 11 be formed of polypropylene bead foam formed into a plate shape. If the core pad 11 is formed of bead foam, it is preferable that a foaming ratio be in a range from 25 to 50 times and the thickness thereof do not exceed an average diameter of beads. If the average diameter of beads of a 30 times foaming ratio has an average diameter from about 4 to about 6 mm, for example, the core pad 11 is sliced into a thickness from about 3 to about 5 mm.

The spacer pads 12 fill in the through holes 11a of the core pad 11. It is preferable that the spacer pads 12 be formed of a three-dimensional knitted material. As disclosed in Japanese Unexamined Patent Application Publication No. 2002-331603 or 2003-182427, for example, the three-dimensional knitted material is a knitted fabric of a three-dimensional structure with ground knitted fabrics in a pair spaced from each other, and a large number of connecting fibers that go back and forth between the ground fabrics in a pair to connect these ground fabrics. Pressing the three-dimensional knitted material with the back of a human being compresses the connecting fibers of the three-dimensional knitted material to apply tensile force on the connecting fibers. Vibration on a surface of a body accompanying a biological signal is transmitted through the muscle of a human being. It is preferable that the spacer pads 12 formed of the three-dimensional knitted material be thicker than the core pad 11. The reason therefor is that affixing the peripheries of the front and rear films 14 and 15 to the peripheries of the through holes 11a presses the spacer pads 12 formed of the three-dimensional knitted material in the direction of the thickness thereof. This generates tensile force resulting from reactive force from the front and rear films 14 and 15, so that solid vibration (membrane vibration) will be generated easily on the front and rear films 14 and 15. This further preliminarily compresses the spacer pads 12 formed of the three-dimensional knitted material to generate tensile force resulting from a reactive force on the connecting fibers that hold the shape of the three-dimensional knitted material in the direction of the thickness thereof, so that string vibration may be generated easily.

The sensor 13 is fixedly attached to one of the spacer pads 12 before the front and rear films 14 and 15 are stacked. As described above, the three-dimensional knitted material forming the spacer pads 12 includes the ground knitted fabrics in a pair and the connecting fibers. String vibration of each connecting fiber is transmitted through a node point with the ground fabric to the front and rear films 14 and 15. Thus, it is preferable that the sensor 13 be fixedly attached to a surface of the spacer pad 12 (surface of the ground fabric). It is preferable that the sensor 13 be a microphone sensor, more preferably, a capacitor microphone sensor.

The structure of the biological state analyzer 60 of this embodiment is described next based on FIG. 4. The biological state analyzer 60 includes body trunk second derivative waveform calculating means 61, maximum amplitude waveform component specifying means 62, inflection point specifying means 63, and state analyzing means 64. The biological state analyzer 60 is formed of a computer. The body trunk second derivative waveform calculating means 61 configured as a computer program executes a body trunk second derivative waveform calculating procedure. The maximum amplitude waveform component specifying means 62 configured as the computer program executes a maximum amplitude waveform component specifying procedure. The inflection point specifying means 63 configured as the computer program executes an inflection point specifying procedure. The state analyzing means 64 configured as the computer program executes a state analyzing procedure. The computer program may be provided as a program stored in a recording medium such as a flexible disk, a hard disk, a CD-ROM, an MO (magnetooptical disk), a DVD-ROM, or a memory card. Alternatively, the computer program can be transferred through a communication line.

The body trunk second derivative waveform calculating means 61 receives a time-series waveform of a body trunk biological signal extracted from the back of a body trunk by the body trunk biological signal measuring device 1, specifically output data transmitted from the sensor 13 (preferably, data in a given frequency domain subjected to filtering (filtering of removing a frequency component resulting from body motion, for example)) and differentiates the received time-series waveform twice, thereby obtaining a second derivative waveform in a time-series manner.

The maximum amplitude waveform component specifying means 62 set in this embodiment is first maximum amplitude waveform component specifying means 621. The first maximum amplitude waveform component specifying means 621 specifies a maximum amplitude waveform component (corresponding to a waveform component of a substantially U shape of a maximum amplitude of a low frequency not containing a high-frequency component superimposed on a waveform in one period) appearing as a result of switch of an amplitude from attenuation to amplification in transition from the contracting phase to the diastolic phase of a ventricle. The maximum amplitude waveform component is specified in each period of a reference form of the second derivative waveform obtained in a time-series manner by the body trunk second derivative waveform calculating means 61. The reference form of the second derivative waveform mentioned herein includes a case where the form of the time-series second derivative waveform at the time of its output from the body trunk second derivative waveform calculating means 61 is used as it is as the reference form, and a case where the form of a waveform generated by vertically inverting the second derivative waveform at the time of its output relative to the base line thereof (line at a scale 0 on a graph) is used as the reference form. Which of these reference forms is to be used is determined according to a condition for calculation employed for processing an original waveform of a biological signal and obtaining a second derivative waveform. Meanwhile, according to test results mentioned later, the form of a second derivative waveform to be used as the reference form is one that associates inflection points in a pair to be specified by the inflection point specifying means 63 after specification of the maximum amplitude waveform component with first heart sound and second heart sound (corresponding to an R wave and a T wave in an electrocardiogram respectively). The first maximum amplitude waveform component specifying means 621 of this embodiment uses a waveform generated by inverting the time-series second derivative waveform at the time of its output from the body trunk second derivative waveform calculating means 61 as the reference form.

The inflection point specifying means 63 specifies inflection points in a pair appearing before and after the maximum amplitude waveform component specified by the first maximum amplitude waveform component specifying means 621 (points where a slope changes by given degrees or more (45 degrees or more, for example) relative to a tangent to the maximum amplitude waveform component). More specifically, an inflection point where an amplitude switches from attenuation to amplification is called a ventricle initial contracting phase responsive wave (E$\alpha$ wave), and an inflection point where the amplitude switches from amplification to attenuation is called a ventricle initial diastolic phase responsive wave (E$\beta$ wave). The E$\alpha$ and E$\beta$ waves are arranged in this order along a temporal axis with the maximum amplitude waveform component placed in therebetween.

The state analyzing means 64 analyzes a biological state using information about inflection points including a particular position of each inflection point (each of the ventricle initial contracting phase responsive wave (Eα wave) and the ventricle initial diastolic phase responsive wave (Eβ wave)) specified from the reference form of the second derivative waveform specified by the first maximum amplitude waveform component specifying means 621 and the inflection point specifying means 63. The particular position of each inflection point means a position on a temporal axis. In addition to this particular position, information such as the amplitude or period of an inflection point may be used for the analysis.

Figure 4:
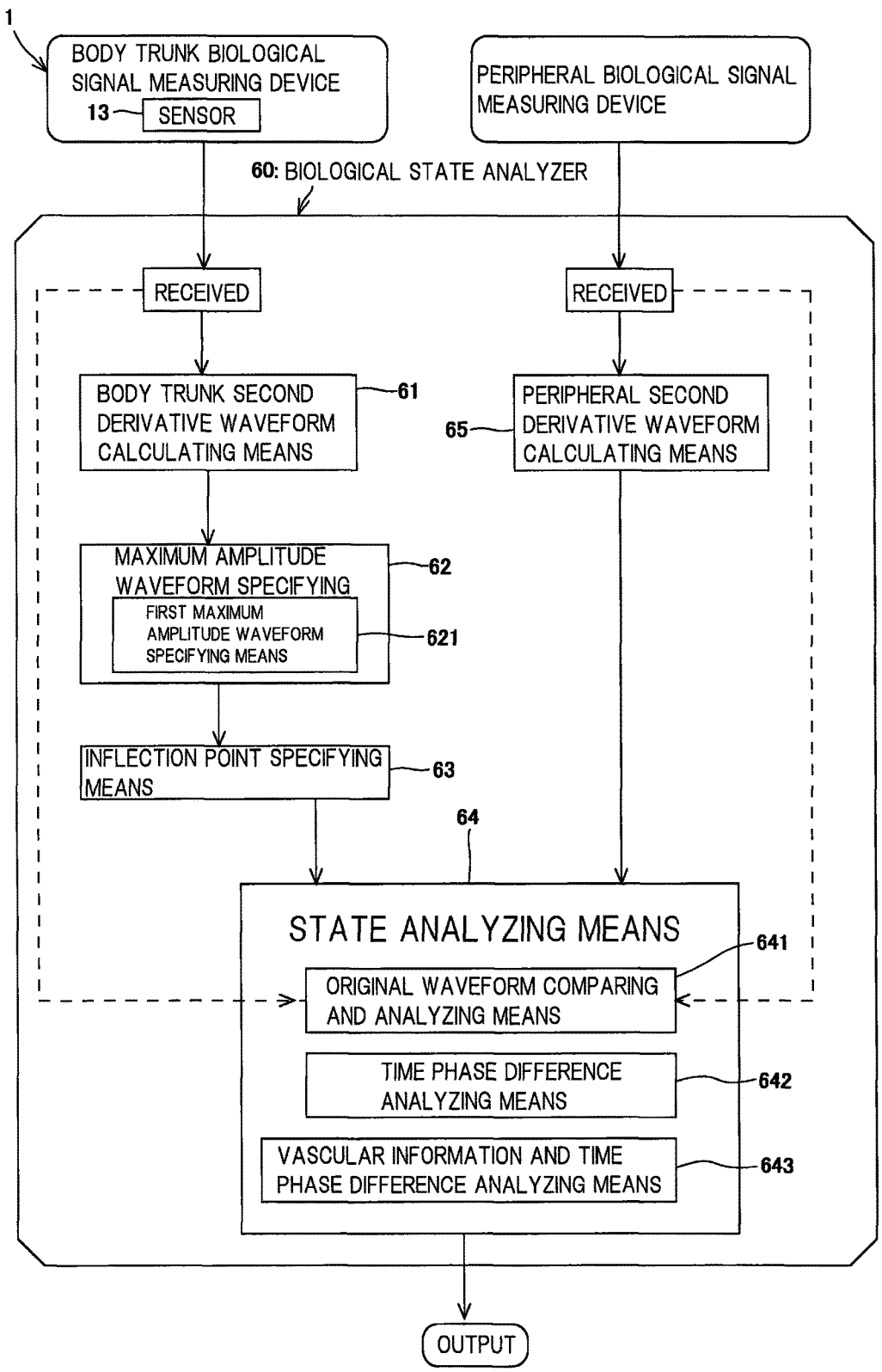
FIG. 4 schematically shows the structure of a biological state analyzer of the embodiment of this invention.

As shown in FIG. 4, the biological signal analyzer 1 of this embodiment further includes the following means as the state analyzing means 64. This means receives a time-series waveform of a peripheral biological signal extracted from a periphery by a peripheral biological signal measuring device (preferably, data in a given frequency domain subjected to filtering (filtering of removing a frequency component resulting from body motion, for example)) and makes analysis using the received peripheral biological signal.

More specifically, as shown in FIG. 4, the biological signal analyzer 1 of this embodiment further includes peripheral second derivative waveform calculating means 65 that executes a peripheral second derivative waveform calculating procedure. The peripheral second derivative waveform calculating means 65 is formed of a computer program that differentiates a time-series waveform of a peripheral biological signal twice transmitted from the peripheral biological signal measuring device and obtains a second derivative waveform in a time-series manner. Typically, a device for measuring a fingertip plethysmogram is used as the peripheral biological signal measuring device.

The state analyzing means 64 further includes means that analyzes a biological state using an initial contracting phase positive wave (a wave) and an initial diastolic phase positive wave (e wave) obtained from a second derivative waveform of a fingertip plethysmogram as a peripheral biological signal obtained by the peripheral second derivative waveform calculating means 65, and using the ventricle initial contracting phase responsive wave (Eα wave) and the ventricle initial diastolic phase responsive wave (Eβ wave). The Eα wave is an anterior inflection point where an amplitude switches from attenuation to amplification. The Eβ wave is a posterior inflection point where the amplitude switches from amplification to attenuation. The Eα and Eβ waves are arranged with the maximum amplitude waveform component placed in therebetween that appears as a substantially U shaped waveform of a low frequency in the second derivative waveform of the reference form specified by the first maximum amplitude waveform component specifying means 621 and the inflection point specifying means 63. More specifically, each means is configured as a computer program and makes determination in consideration of time phases. As one means that makes determination in consideration of a time phase, this embodiment includes time phase difference analyzing means 642 that executes a time phase difference analyzing procedure, and vascular information and time phase difference analyzing means 643 that executes a vascular information and time phase difference analyzing procedure.

The time phase difference analyzing means 642 obtains a time phase difference of heart-to-fingertip propagation time between the initial contracting phase positive wave (a wave) obtained by the peripheral second derivative waveform calculating means 65 and the anterior ventricle initial contracting phase responsive wave (Eα wave) next to the maximum amplitude waveform component obtained by the first maximum amplitude waveform component specifying means 621 and the inflection point specifying means 63 for each pertinent period. The time phase difference analyzing means 642 further obtains a time phase difference of heart-to-fingertip propagation time between the initial diastolic phase positive wave (e wave) obtained by the peripheral second derivative waveform calculating means 65 and the posterior ventricle initial diastolic phase responsive wave (Eβ wave) next to the maximum amplitude waveform component obtained by the first maximum amplitude waveform component specifying means 621 and the inflection point specifying means 63 for each pertinent period. Based on these time phase differences, the time phase difference analyzing means 642 analyzes the state of a sympathetic nervous system. As understood from Example 1 described later, the initial contracting phase positive wave (a wave) of a fingertip plethysmogram relates to the ventricle initial contracting phase responsive wave (Eα wave) of an APW, and the initial diastolic phase positive wave (e wave) of the fingertip plethysmogram relates to the ventricle initial diastolic phase responsive wave (Eβ wave) of the APW. The fingertip plethysmogram as peripheral information and the APW as information about a part near a central system are both generated as a result of heart rate fluctuation and variation in a heart rate governed by sympathetic nerves. This generates a certain time phase difference therebetween and this time phase difference indicates a difference between the degrees of control by sympathetic nerves.

As shown in FIG. 25 referred to later, to understand the activity of a sympathetic nervous system more clearly, it is preferable that the time phase difference analyzing means 642 include means that plots coordinate points on a coordinate in association with each period. This coordinate has one axis representing a time phase difference of heart-to-fingertip propagation time (a–Eα) between the initial contracting phase positive wave (a wave) of a fingertip plethysmogram and the ventricle initial contracting phase responsive wave (Eα wave) of an APW, and a different axis representing a time phase difference of heart-to-fingertip propagation time (e–Eβ) between the initial diastolic phase positive wave (e wave) of the fingertip plethysmogram and the ventricle initial diastolic phase responsive wave (Eβ wave) of the APW. The activity of a sympathetic nervous system can be determined by determining whether the plotted coordinate points are in a dispersed or converging state on each coordinate. As shown in FIG. 25(*a*) referred to later, if coordinate points are collected together comparatively and tend to converge gently while a time phase difference is observed, for example, it is determined that parasympathetic nerves and sympathetic nerves appear to the substantially same degree. If coordinate points are plotted in substantially one place and there is substantially no time phase difference as shown in FIG. 25(*c*) or (*d*), it is determined that the parasympathetic nervous system is predominant. If there is a large time phase difference and coordinate points are dispersed as shown in FIG. 25(*b*), it is determined that the function of sympathetic nerves is stimulated. A degree of dispersion or convergence used to distinguish between a state where parasympathetic nerves and sympathetic nerves are well balanced, a state where the parasympathetic nerves are predominant, and a state where the function of the sympathetic nerves is stimulated can be determined based on whether plotted coordinate points are within a certain range using an algorithm indicating the range of the coordinate points.

The vascular information and time phase difference analyzing means 643 is means that plots a coordinate having one axis representing at least one of the time phase difference of heart-to-fingertip propagation time (a–Eα) between the initial contracting phase positive wave (a wave) of a fingertip plethysmogram and the ventricle initial contracting phase responsive wave (Eα wave) of an APW and the time phase difference of heart-to-fingertip propagation time (e–Eβ) between the initial diastolic phase positive wave (e wave) of the fingertip plethysmogram and the ventricle initial diastolic phase responsive wave (Eβ wave) of the APW obtained by the time phase difference analyzing means 642, and a different axis representing a wave height ratio (e/a value) between the initial contacting phase positive wave (a wave) and the initial diastolic phase positive wave (e wave). The a and e waves are some indexes that change significantly in response to the presence or absence of arteriosclerosis or represent the state of a peripheral blood flow. By placing this wave height ratio on one axis, information such as the age of a vessel can be obtained. Vascular information means information of various types indicating the states of a vessel including a hemodynamic status, and the stiffness and the elasticity of the vessel. The wave height ratio (e/a value) is an example of this information. The e/a value is affected mainly by the stiffness and the elasticity of the vessel and is used to estimate the age of the vessel.

Considering this information together with the time phase difference (a–Eα) or the time phase difference (e–Eβ) representing information about a sympathetic nervous system makes it possible to understand the physical or mental state of a human being more precisely who behaves like a low-dimensional chaos due to the presence or absence of a cardiovascular disease or other diseases, change in a physical state caused by alcohol drinking, or drug taking or aging, for example.

The vascular information and time phase difference analyzing means 643 determines the state of a human being including the presence or absence of stress caused by an external factor such as a disease based on the position of each coordinate point and a degree of dispersion of coordinate points plotted on a coordinate. Like in the aforementioned way, the degree of dispersion can be determined using a certain algorithm. As an example, an appropriate threshold may be set by comparing the position of a coordinate point, a degree of dispersion of coordinate points and the like with data about a person without any disability, or by comparing data about a person himself or herself obtained when the person is in good health, thereby determining change in a state. This determination is described in more detail later.

As shown in FIG. 4, the state analyzing means 64 of the biological state analyzer 60 of this embodiment further includes original waveform comparing and analyzing means 641. The original waveform comparing and analyzing means 641 compares the frequency and the amplitude of a time-series waveform of a body trunk biological signal and those of a time-series waveform of a peripheral biological signal to determine the presence or absence of a probability of a cardiovascular disease. Specifically, as described above, an aortic pulse wave as a body trunk biological signal contains information about the contracting phase and the diastolic phase of a ventricle and elasticity information about a vascular wall functioning as an auxiliary pump for circulation. Thus, if a time-series waveform (original waveform) of an aortic pulse wave (APW) as a body trunk biological signal and a time-series waveform (original waveform) of a fingertip plethysmogram as a peripheral biological signal are compared and a large difference is found between the appearances of these waveforms (in frequency or amplitude), the existence of some abnormality occurring between the center and a periphery can also be estimated from these original waveforms.

As clearly understood from a result of Example 2 described later, it is preferable that the original waveform comparing and analyzing means 641 be configured so as to determine that there might be cardiovascular abnormality if differences in frequency between a time-series waveform of a body trunk biological signal and a time-series waveform of a peripheral biological signal are substantially the same and if the time-series waveform of the body trunk biological signal is smaller in amplitude than the time-series waveform of the peripheral biological signal. Regarding a criterion for determining that the body trunk biological signal tends to be smaller in amplitude than the peripheral biological signal, the time-series waveforms are compared in a given measuring time. If the amplitude of the time-series waveform of the body trunk biological signal is two thirds or less, more typically, half or less of the amplitude of the time-series waveform of the peripheral biological signal in a time period of half or more of the measuring time for the comparison, for example, a blood flow is considered not to be normal. In this case, the presence of some cardiovascular abnormality such as mitral regurgitation can be estimated.

In this embodiment, the state analyzing means 64 includes all the original waveform comparing and analyzing means 641, the time phase difference analyzing means 642, and the vascular information and time phase difference analyzing means 643. Alternatively, the state analyzing means 64 may include at least one of these means.

EXAMPLES

As described below, an aortic pulse wave (APW) as a body trunk biological signal was measured by the body trunk biological signal measuring device 1 of the aforementioned embodiment and a biological state was analyzed by the biological state analyzer 60 of the aforementioned embodiment using resultant measurement data.

The body trunk biological signal measuring device 1 used in Examples has the structure of FIGS. 1 to 3. The body trunk biological signal measuring device 1 has the following physical properties.

(Properties of Body Trunk Biological Signal Measuring Device 1)

Figure 5:
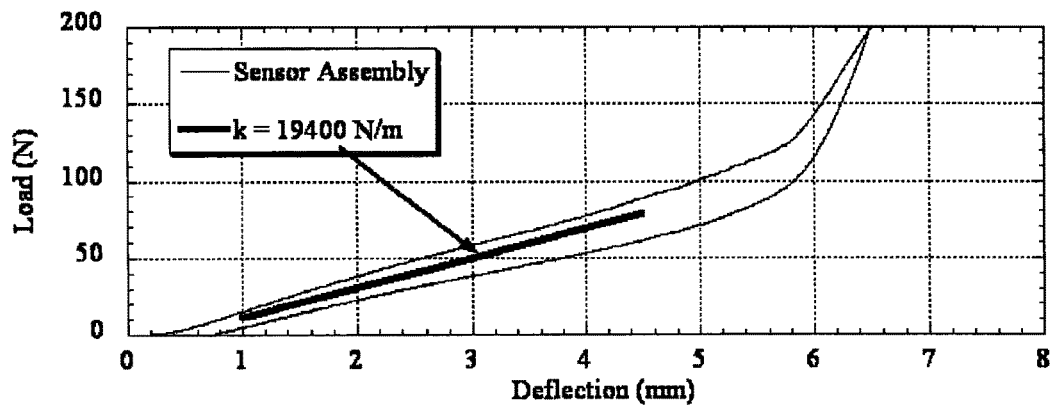
FIG. 5 shows load-deflection properties of the body trunk biological signal measuring device shown in FIG. 1.
Figure 6:
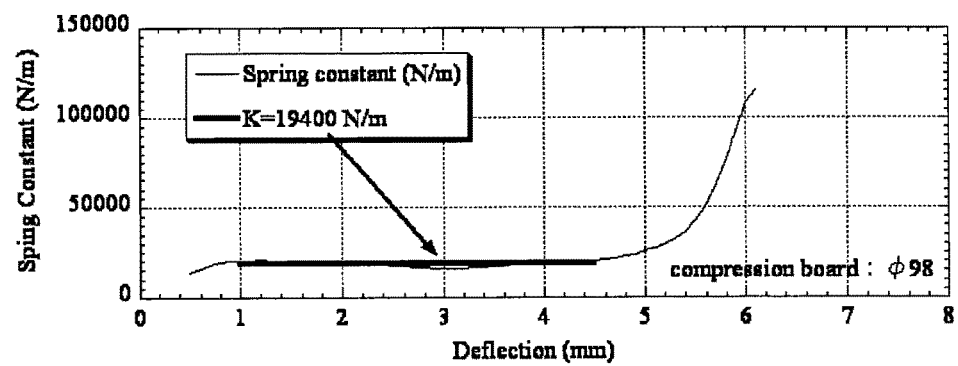
FIG. 6 is a view resulting from conversion of the vertical axis of the graph in FIG. 5 to a spring constant.

A wooden disk of a diameter of 98 mm was attached to AUTOGRAPH available from Shimadzu Corporation and a load up to 200 N was applied in a Z direction of FIG. 3 at a moving velocity of 50 mm/min. FIG. 5 shows resultant load-deflection properties. FIG. 6 is a view resulting from conversion of the vertical axis of FIG. 5 to a spring constant. As understood from these drawings, within a compression allowance from 1 to 4.5 mm, the body trunk biological signal measuring device 1 exhibits a spring constant of a constant value k of 19400 N/m.

Figure 7:
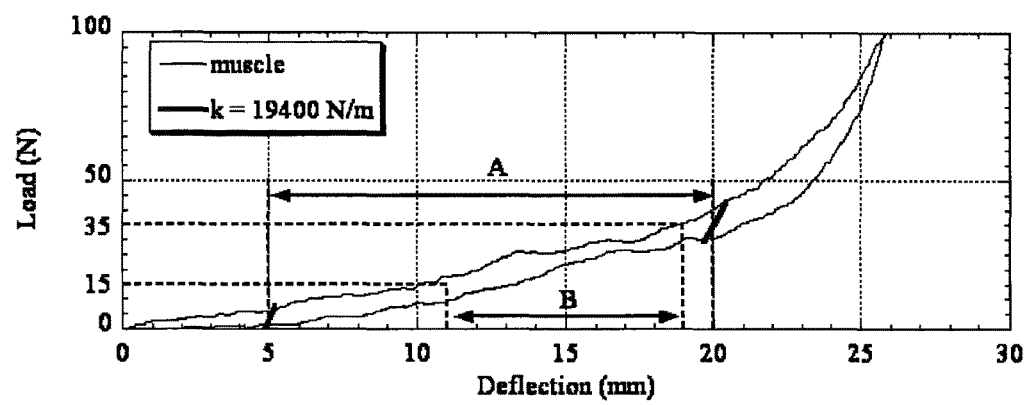
FIG. 7 shows exemplary load-deflection properties of the lumber of a human being.
Figure 8:
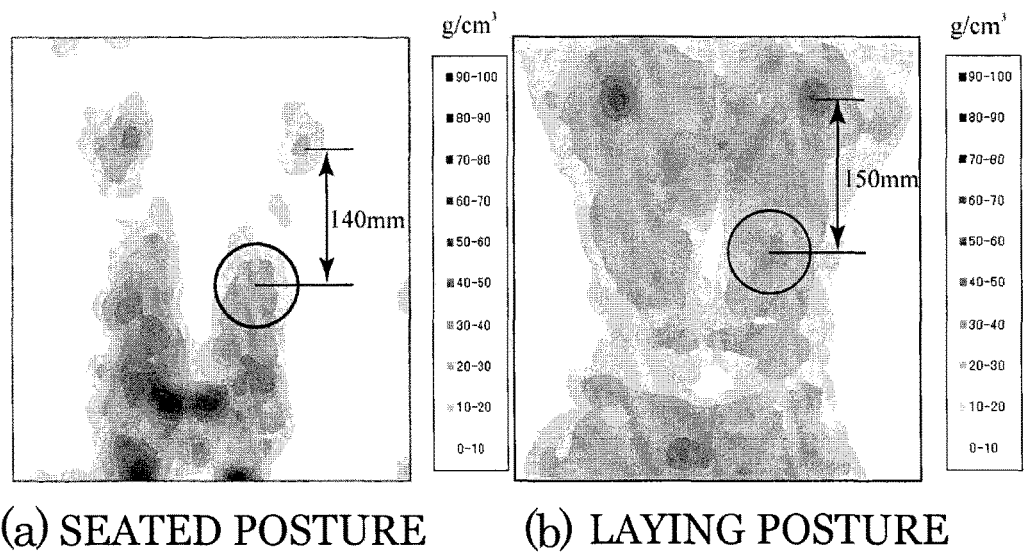
FIG. 8(a) shows a body pressure distribution at the back of a body trunk obtained while a subject is seated on an automobile seat.
FIG. 8(b) shows a body pressure distribution at the back of a body trunk obtained while a different subject lies on a mattress.

Next, to examine static properties of the lumbar of a human being as a part of the back of a body trunk to form abutting contact with the body trunk biological signal measuring device 1, static load experiment and experiment to measure a body pressure distribution in a lying posture and a seated posture were conducted. Like FIG. 5, FIG. 7 shows load-deflection properties obtained by attaching a wooden disk of a diameter of 98 mm to AUTOGRAPH and applying a load up to 100 N at a moving velocity of 50 mm/min. FIG. 8 shows body pressure distributions at the respective backs of body trunks of two subjects of different physical constitutions in a seated posture on a general automobile seat and in a lying posture on a mattress. The subject of FIG. 8(a) had a physical constitution with a height of 172 cm and a weight of 52 kg. The subject of FIG. 8(b) had a physical constitution with a height of 178 cm and a weight of 76 kg. Positions indicated by circles in FIG. 8 indicate the apex of a heart and correspond to a range of 140 to 150 mm as measured from a shoulder blade. In FIGS. 8(a) and 8(b), reactive forces from both the seat and the mattress exhibited a load value from 15 to 35 N in an area of a diameter of 98 mm. This value corresponds to reactive force determined with a deflection allowance in a range B of FIG. 7. A force comparable to this reactive force was applied to the body trunk biological signal measuring device 1 and a resultant spring constant was within a range of deflection from 1 to 2 mm with an allowance of 2.5 mm, as seen from FIG. 5. Thus, the body trunk biological signal measuring device 1 is found to have an ability to withstand load fluctuation up to 3 G.

The spring constant k of 19400 N/m of the body trunk biological signal measuring device 1 is approximate to a dynamic spring constant determined with the muscle of a lumbar compressed from about 5 to about 20 mm (range A of FIG. 7) in terms of load-deflection properties of the lumber. As an example, this spring constant corresponds to a dynamic spring constant determined under a vibration condition of a half amplitude of 0.2 mm while the muscle is compressed 5 mm, or a dynamic spring constant determined under a vibration condition of a half amplitude of 0.4 mm while the muscle is compressed 20 mm. Thus, by absorbing amplitude fluctuation with hysteresis loss of the body trunk biological signal measuring device 1 itself and abutting on the back of a body trunk including the lumber, the body trunk biological signal measuring device 1 can grasp pressure fluctuation from the back of the body trunk including the lumber according to a tonometry method.

FIGS. 9(a) and (b) show a time-series waveform of an aortic pulse wave (APW) as a body trunk biological signal obtained from a subject seated on an automobile seat including a seat back in which the body trunk biological signal measuring device 1 is incorporated, and a result of analysis of this time-series waveform respectively. Each of FIGS. 9(a) and (b) further includes a time-series waveform of a fingertip plethysmogram measured at the same time and a result of analysis of this time-series waveform. The fingertip plethysmogram was measured by attaching an optical fingertip plethysmogram meter to the left index finger of the subject. The results of the frequency analysis show that the frequency components agree at 1.14 Hz and the time-series waveform of the APW extracted by the body trunk biological signal measuring device 1 includes heart rate variability.

Example 1

Experiment to Examine Relationship Among Aortic Pulse Wave (APW) as Body Trunk Biological Signal, Fingertip Plethysmogram as Peripheral Biological Signal, and Heart Sound Method of Experiment The body trunk biological signal measuring device 1 was placed on a bed. Two healthy men including a subject A in his twenties and a subject B in his thirties were made to lie on the bed in a face-up posture. The body trunk biological signal measuring device 1 was set so as to form abutting contacts with the backs of the subjects. Output signals from the sensor 13 were received by the biological state analyzer 60 and aortic pulse waves (APWs) as body trunk biological signals were extracted. At the same time, fingertip plethysmograms were measured by optical fingertip plethysmogram sensors to their left index fingers and heart sounds were measured by acceleration sensors attached to their apexes of hearts. Respiration sensors were attached to their chests to measure respirations. The subjects A and B were placed in a face-up lying posture and were in a resting state with their eyes opened during the measurement. One measuring time was 15 seconds and all the devices were synchronized for the measurement.

Result of Experiment

Figure 10:
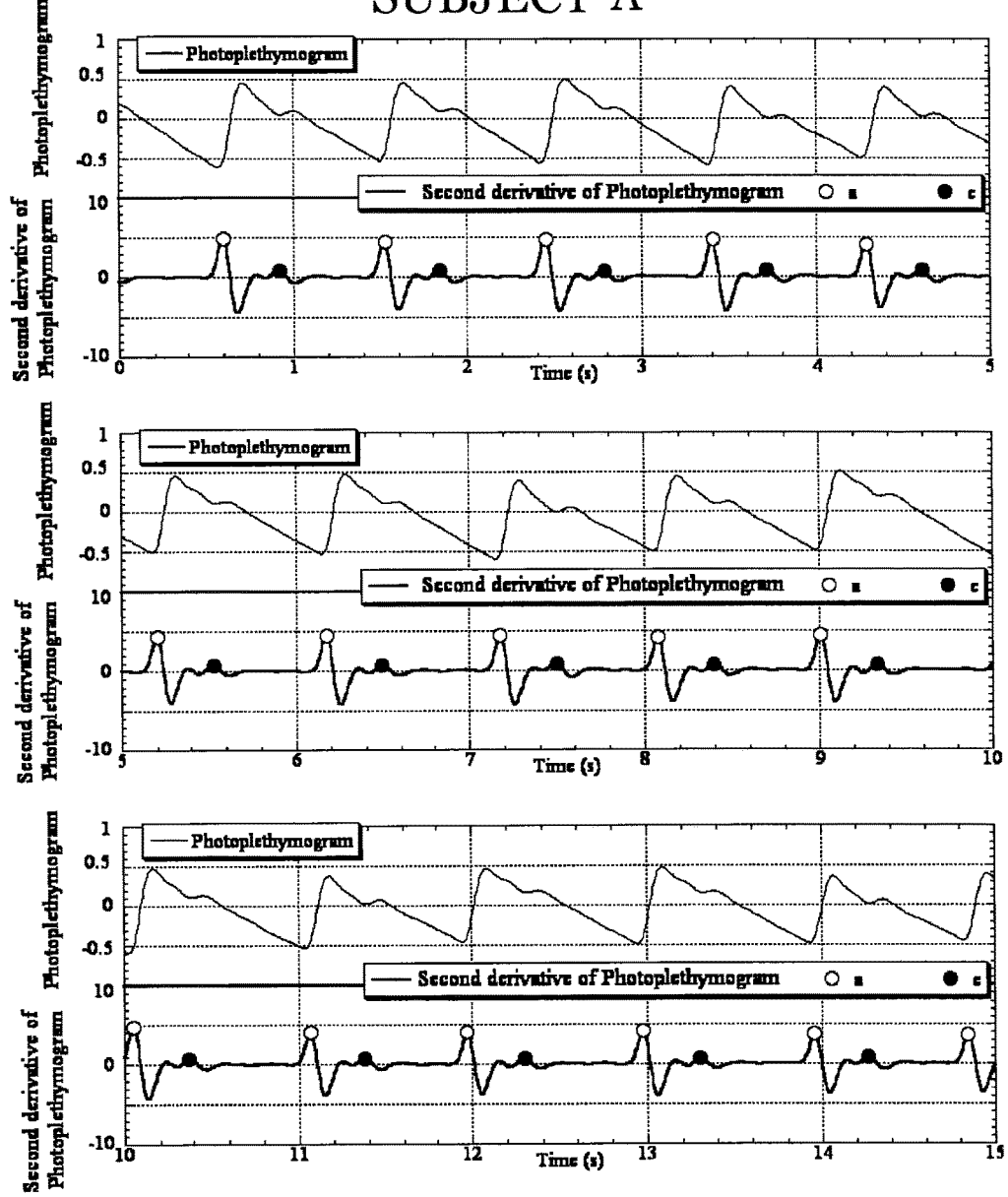
FIG. 10 shows a time-series waveform of a fingertip plethysmogram obtained from a subject A and a second derivative waveform thereof.
Figure 11:
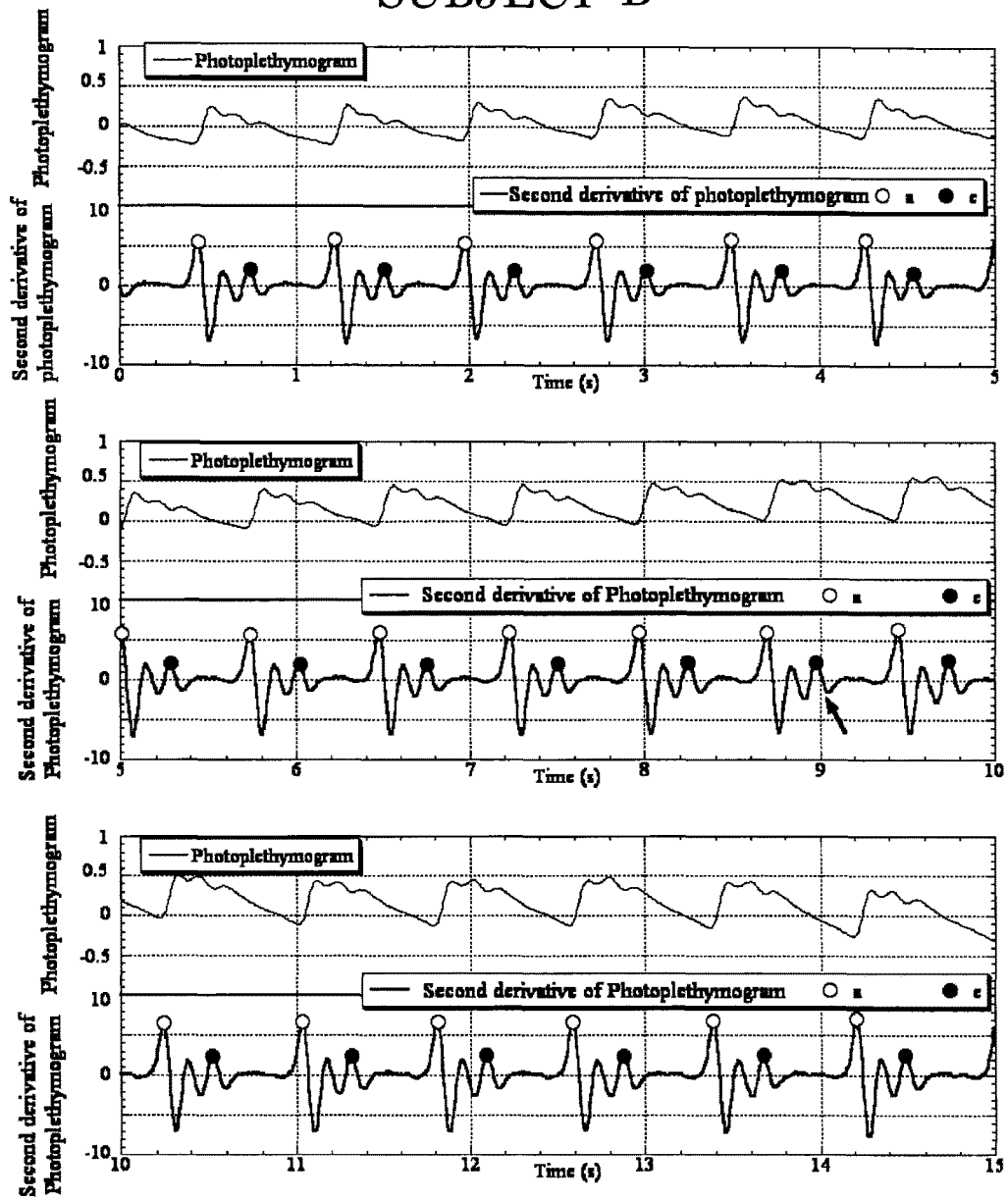
FIG. 11 shows a time-series waveform of a fingertip plethysmogram obtained from a subject B and a second derivative waveform thereof.
Figure 12:
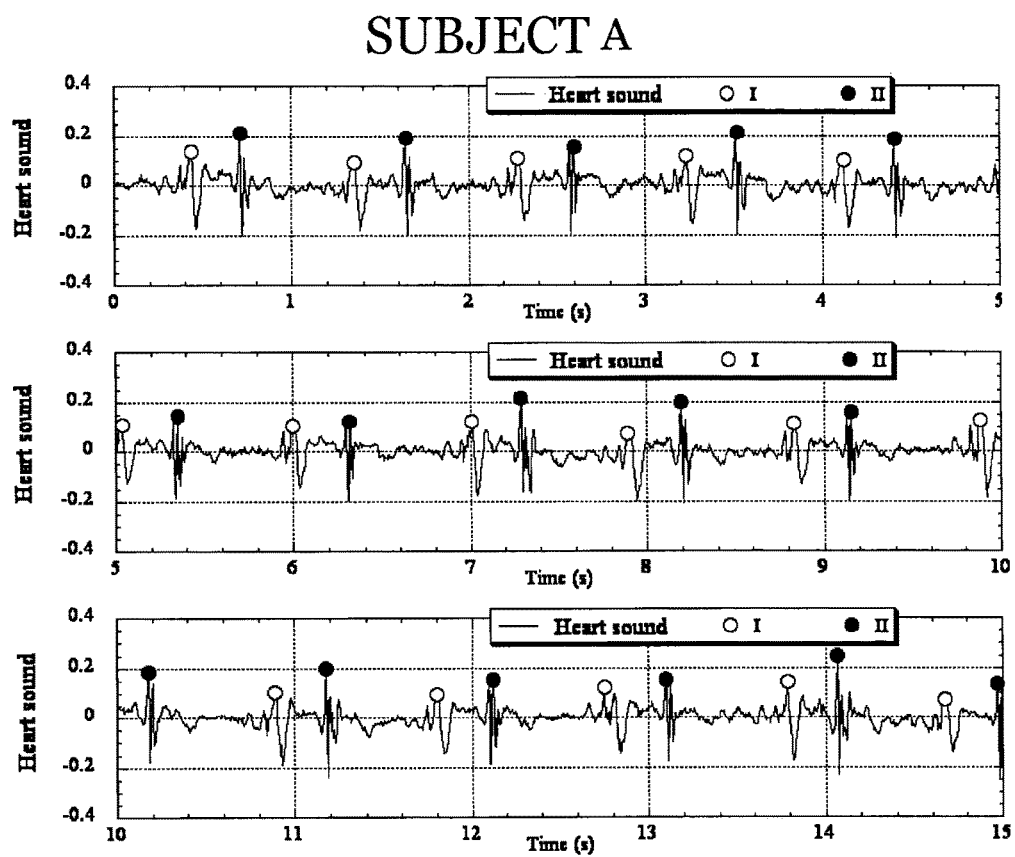
FIG. 12 shows heart sound measured from the subject A.
Figure 13:
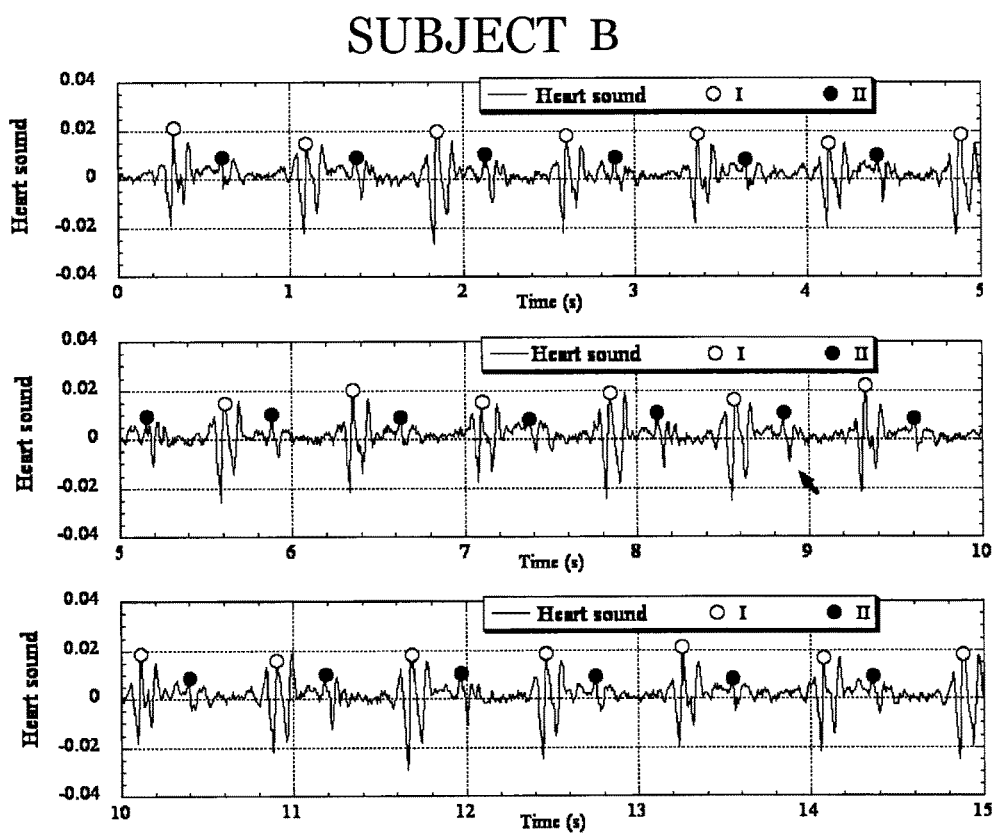
FIG. 13 shows heart sound measured from the subject B.

FIGS. 10 and 11 show time-series waveforms of fingertip plethysmograms measured from the subjects A and B respectively, and the initial contracting phase positive wave (a wave) and the initial diastolic phase positive wave (e wave) of the second derivative waveform of each of the fingertip plethysmograms. FIGS. 12 and 13 show heart sounds measured from the subjects A and B respectively. In terms of a time phase of heart sound and that of a fingertip plethysmogram, the initial contracting phase positive wave (a wave) of the fingertip plethysmogram corresponds to first heart sound heard at an initial stage of a contracting phase, and the initial diastolic phase positive wave (e wave) of the fingertip plethysmogram corresponds to second heart sound heard at an end stage of the contracting phase. Both a time phase difference between the first heart sound and the initial contracting phase positive wave (a wave) of the fingertip plethysmogram and a time phase difference between the second heart sound and the initial diastolic phase positive wave (e wave) of the fingertip plethysmogram were found to be in a range from 0.10 to 0.18 seconds. The time phase difference obtained from a propagation speed of a pulse wave was 0.16 seconds that is approximate to the time phase differences shown in the experiment result.

Figure 14:
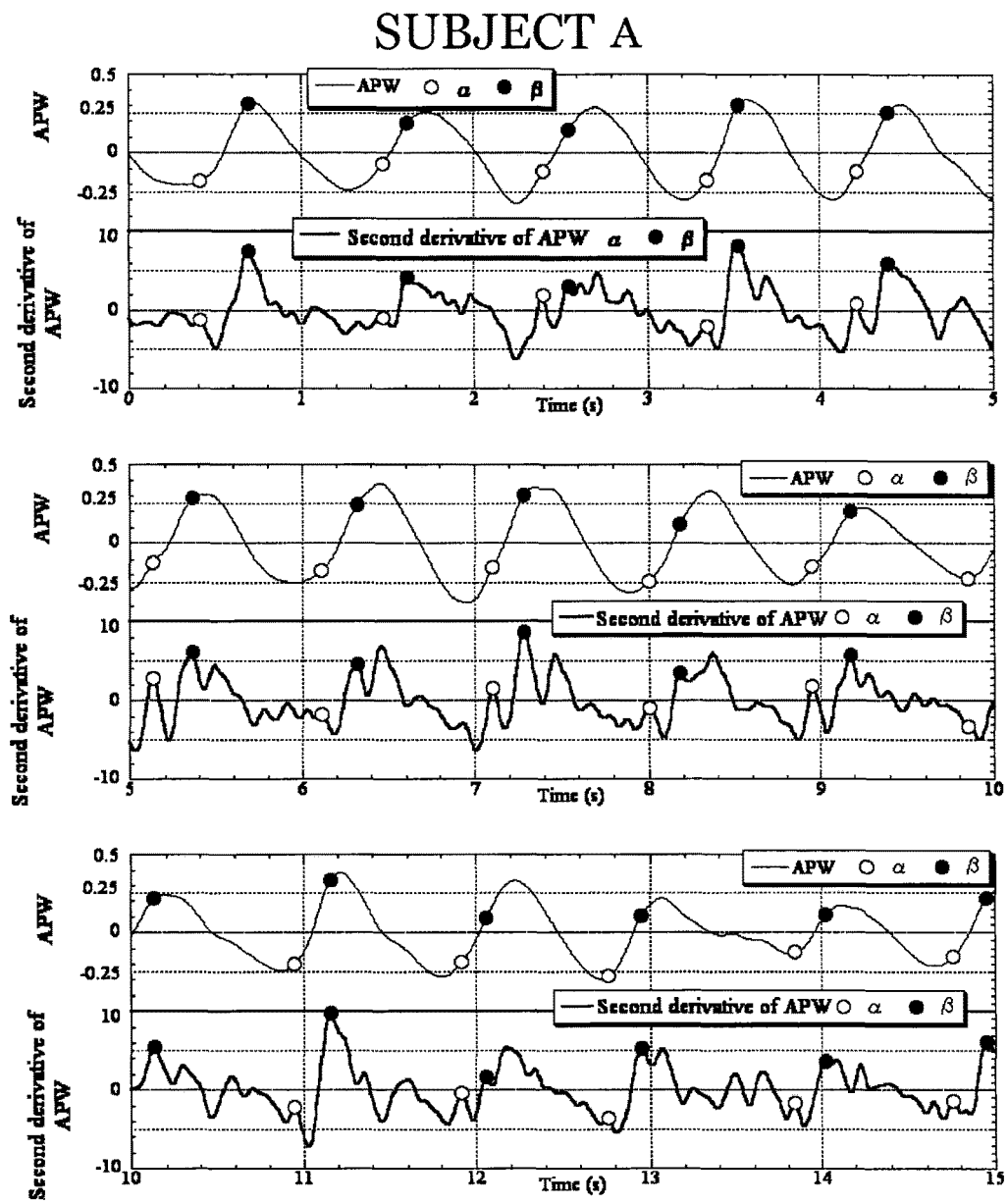
FIG. 14 shows an original waveform of an aortic pulse wave (APW) measured from the subject A and a second derivative waveform thereof.
Figure 15:
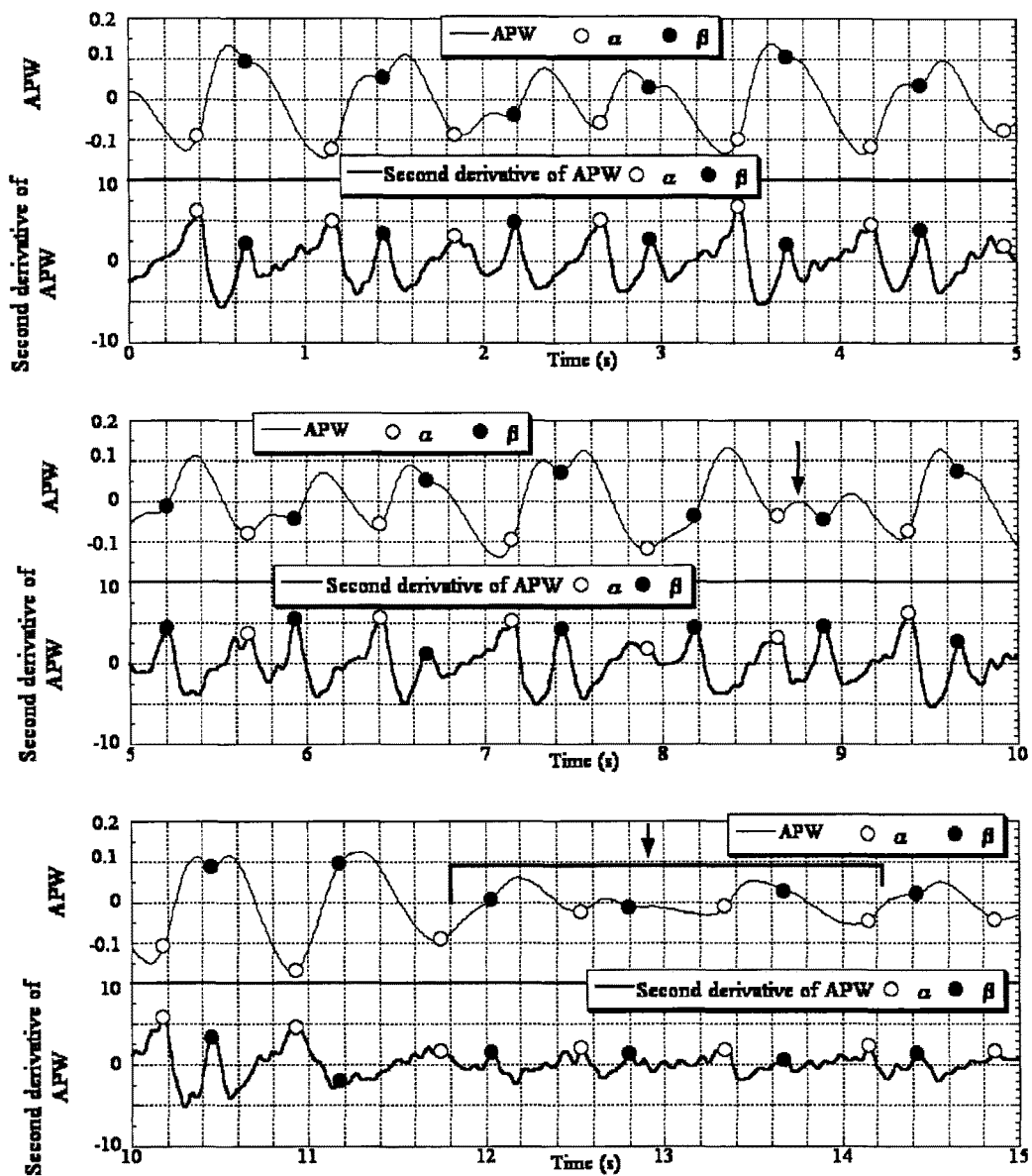
FIG. 15 shows an original waveform of an aortic pulse wave (APW) measured from the subject B and a second derivative waveform thereof.
Figure 16:
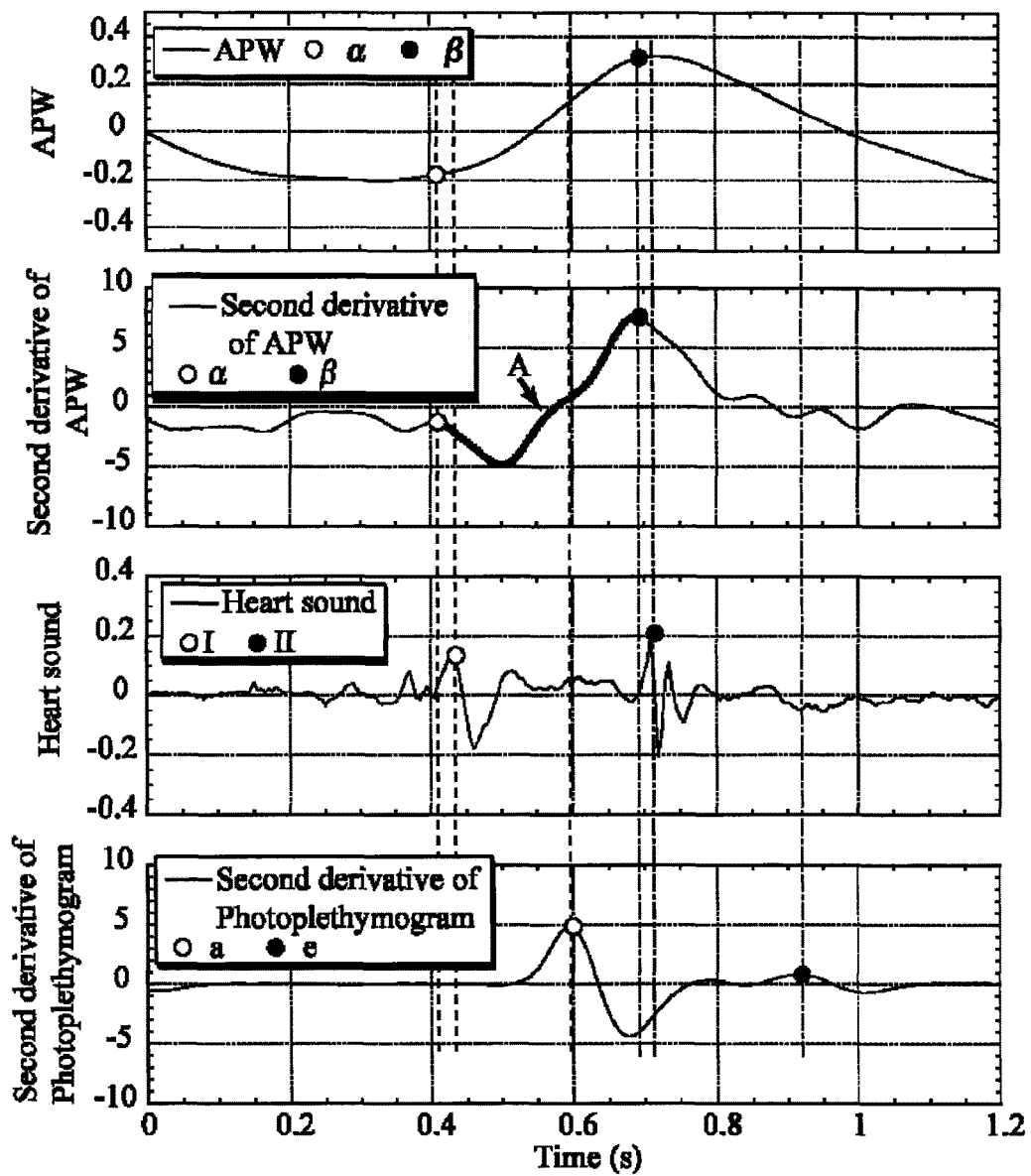
FIG. 16 shows a relationship among heart sound, an aortic pulse wave (APW), and a fingertip plethysmogram in an enlarged manner.

FIGS. 14 and 15 show original waveforms of aortic pulse waves (APWs) measured from the subjects A and B respectively, and waveforms generated by inverting second derivative waveforms of these APWs at the time of their outputs (in this example, these inverted waveforms are called "waveforms of a reference form"). Vibration generated by opening and closing of a valve or change in a blood flow state resulting from heart beat occurs as first heart sound and second heart sound and is audible sound at 20 Hz. Thus, the first and second heart sounds correspond to parts of an APW where vibration energy becomes high. These parts where vibration energy becomes high were determined in a time-series waveform of the reference form of the second derivative waveform of the APW and found that in each second derivative waveform (waveform of one period), and they were found to correspond to inflection points (ventricle initial contracting phase responsive wave (Eα wave) and ventricle initial diastolic phase responsive wave (Eβ wave)) appearing before and after a negative wave in a contracting phase appearing as a waveform component of a maximum amplitude of a low frequency excluding a high-frequency component superimposed on a waveform (waveform component indicated by an arrow A of FIG. 16). Thus, the inflection point (ventricle initial contracting phase responsive wave (Eα wave)) appearing before the maximum amplitude waveform component of the second derivative waveform of the APW in the aforementioned reference form corresponds to the first heart sound and an a wave of the fingertip plethysmogram. Further, the inflection point (ventricle initial diastolic phase responsive wave (Eβ wave)) appearing after the second derivative waveform of the APW of the aforementioned reference form corresponds to the second heart sound and an e wave of the fingertip plethysmogram. It is concluded accordingly that the anterior inflection point (ventricle initial contracting phase responsive wave (Eα wave)) reflects vibration resulting from closure of an atrioventricular valve, opening of an aortic valve or a vortex flow system of an artery, and that the posterior inflection point (ventricle initial diastolic phase responsive wave (Eβ wave)) reflects vibration resulting from closure of an aortic valve, opening of an atrioventricular valve, vibration on an artery wall, or deformation of a heart caused by heart beat, for example.

Figure 17:
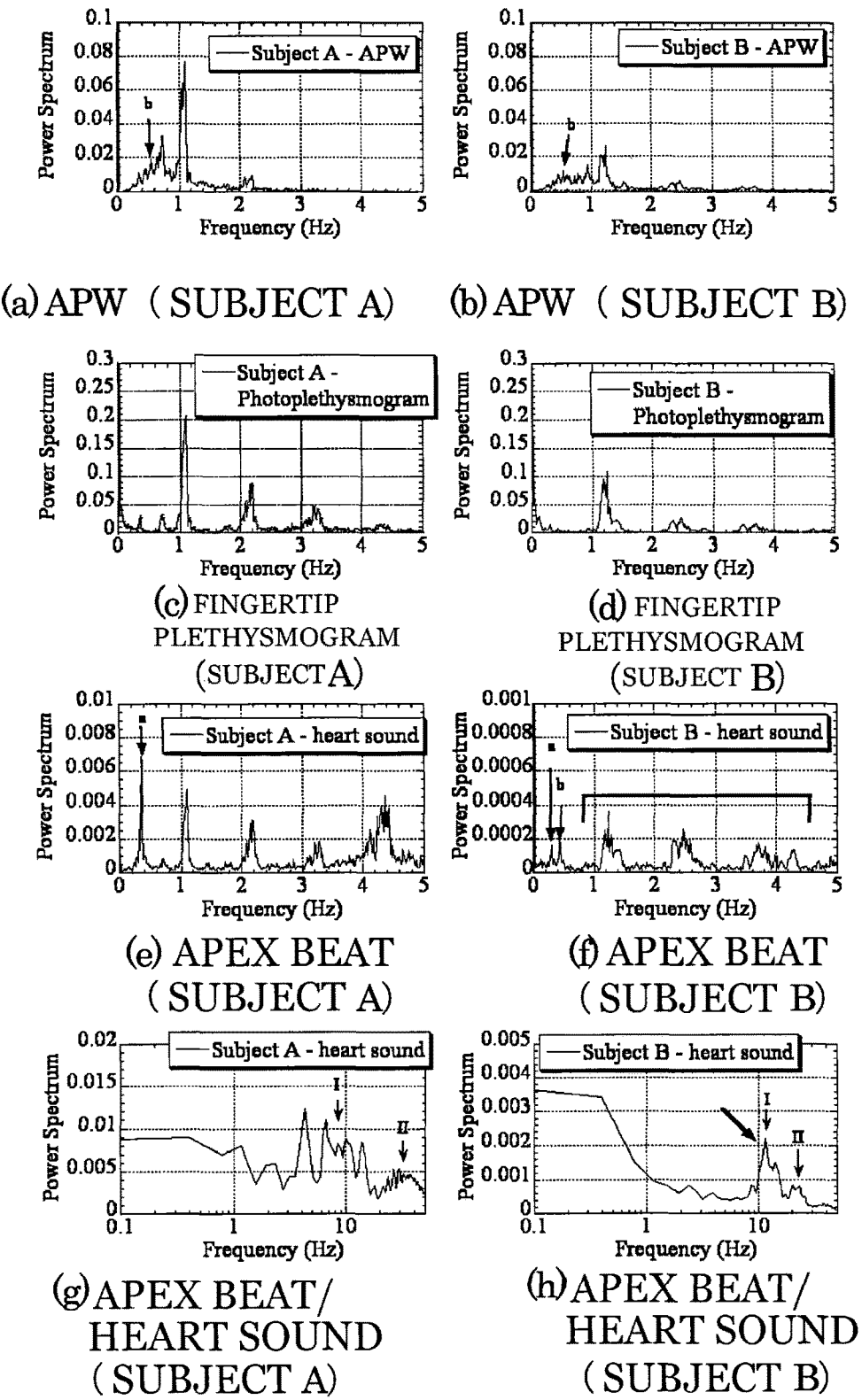
FIGS. 17(a) to (h) show frequency analysis results of the APW, fingertip plethysmogram, apex beat, and heart sound of the subject A, and those of the subject B.

FIGS. 17(*a*) to (*h*) show frequency analysis results of the APW, fingertip plethysmogram, apex beat, and heart sound of the subject A, and those of the subject B. To show the respective bands of first heart sound and second heart sound, analysis results are logarithmically shown with frequencies of apex beat and heart sound up to 50 Hz in FIGS. 17(*g*), (*h*). FIGS. 17(*a*), (*c*), and (*e*) show that the power spectrum of the subject A increases at 1.10 Hz, 2.19 Hz, and 3.22 Hz components. FIGS. 17(*b*), (*d*), and (*f*) show that the power spectrum of the subject B increases at 1.23 Hz, 2.47 Hz, and 3.52 Hz components. This shows that the APW grasps heart rate variability. Meanwhile, the APW contains information about 0.5 Hz and its vicinity indicated by an arrow b not included in the fingertip plethysmogram. This information about 0.5 Hz and its vicinity appears in the data about the subject B of FIG. 17(*f*) showing the frequency analysis result of heart sound, whereas it does not appear in the data about the subject A shown in FIG. 17(*e*). Grasping this information may be difficult only from information about heart sound. Heart sound to be measured is sound transmitted from the front of a body to a chest. Thus, vibration at 0.5 Hz and its vicinity is considered to occur resulting for example from deformation of a heart attenuates and is hard to grasp accordingly. Meanwhile, the APW to be grasped from the back of a body is vibration transmitted to bones through musculus iliocostalis lumborum, making it possible to grasp vibration occurring at 0.5 Hz and its vicinity. Arrows a shown in the frequency analysis results of apex beat and heart sound indicate respiratory components that were confirmed by analyzing the frequency of a biological signal obtained simultaneously by the respiration sensor.

Figure 18:
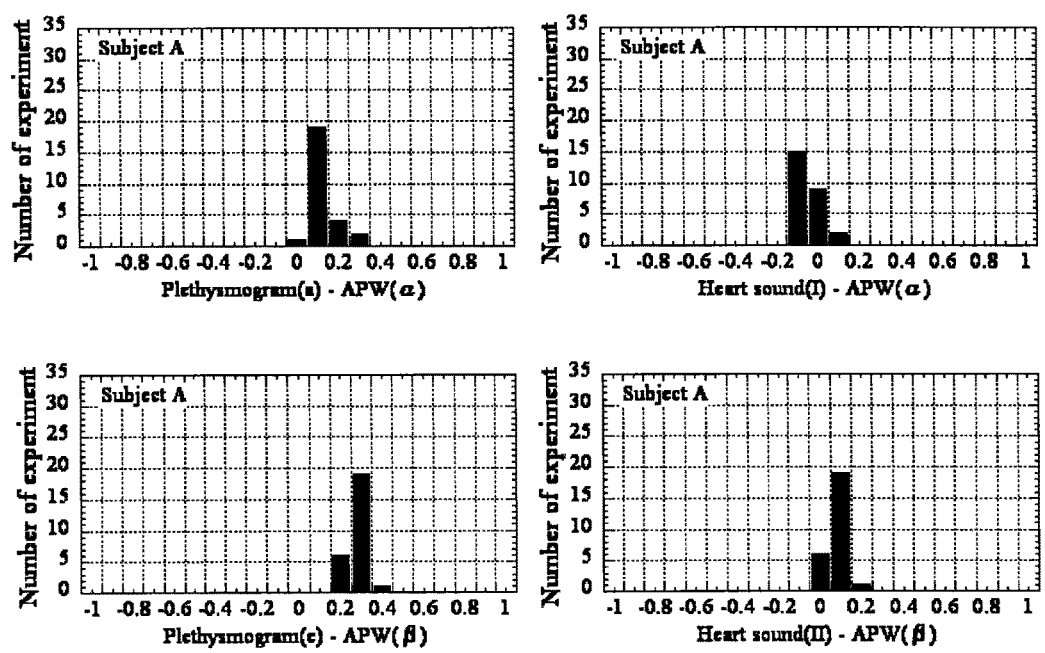
FIG. 18 explains a time phase shift observed in an a wave and an e wave of the fingertip plethysmogram, first heart sound, second heart sound, and the second derivative waveform of the APW of a reference form regarding the subject A.
Figure 19:
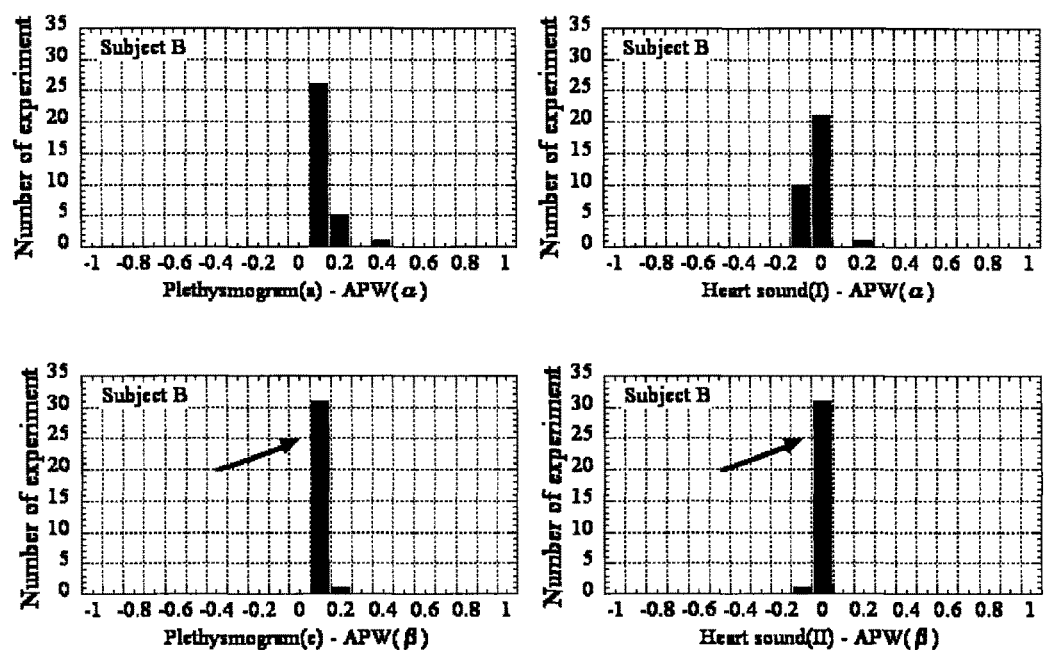
FIG. 19 explains a time phase shift observed in an a wave and an e wave of the fingertip plethysmogram, first heart sound, second heart sound, and the second derivative waveform of the APW of the reference form regarding the subject B.

Referring to each of FIGS. 18 and 19, regarding the a and e waves of the fingertip plethysmogram, first heart sound, second heart sound, and the anterior inflection point (ventricle initial contracting phase responsive wave (Eα wave)) and the posterior inflection point (ventricle initial diastolic phase responsive wave (Eβ wave)) in the second derivative waveform of the reference form of the APW shown in FIGS. 10 to 15, a horizontal axis represents a shift between time phases of corresponding components, and a vertical axis represents the number of measurements. The anterior inflection point (ventricle initial contracting phase responsive wave (Eα wave)) in the second derivative waveform of the reference form of the APW agreed with an a wave as the initial contracting phase positive wave of the fingertip plethysmogram within a time phase difference of 0.2 seconds to a precision of 92.3% about the subject A and 96.9% about the subject B. The anterior inflection point (ventricle initial contracting phase responsive wave (Eα wave)) in the second derivative waveform of the reference form of the APW agreed with the first heart sound within a time phase difference of 0.2 seconds to a precision of 100.0% about both the subjects A and B. The posterior inflection point (ventricle initial diastolic phase responsive wave (Eβ wave)) in the second derivative waveform of the reference form of the APW agreed with an e wave as the initial diastolic phase positive wave of the fingertip plethysmogram within a time phase difference of 0.2 seconds to a precision of 23.1% about the subject A and 100.0% about the subject B. The posterior inflection point (ventricle initial diastolic phase responsive wave (Eβ wave)) in the second derivative waveform of the reference form of the APW agreed with the second heart sound within a time phase difference of 0.2 seconds to a precision of 100.0% about both the subjects A and B. If a threshold for the time phase difference for the subject A is changed from 0.2 seconds to 0.3 seconds, the posterior inflection point (ventricle initial diastolic phase responsive wave (Eβ wave)) in the second derivative waveform of the reference form of the APW agrees with the e wave as the initial diastolic phase positive wave of the fingertip plethysmogram to a precision increased from 23.1% to 96.2%. This is considered to result from the fact that the subject A is younger than the subject B, so that a pulse wave propagation speed tends to be lower in the subject A than in the subject B.

As described above, the anterior inflection point (ventricle initial contracting phase responsive wave (Eα wave)) in the second derivative waveform of the reference form of the APW and the posterior inflection point (ventricle initial diastolic phase responsive wave (Eβ wave)) in the second derivative waveform of the reference form of the APW correspond to first heart sound and second heart sound respectively. It can therefore be understood that making the first maximum amplitude waveform component specifying means 631 set in the biological state analyzer 60 specify the ventricle initial contracting phase responsive wave (Eα wave) and the ventricle initial diastolic phase responsive wave (Eβ wave) in each inverted waveform of the second derivative waveform (inverted second derivative waveform) obtained in a time-series manner by the body trunk second derivative waveform calculating means 61 allows the state analyzing means 63 to analyze a biological state using information about the ventricle initial contracting phase responsive wave (Eα wave) and the ventricle initial diastolic phase responsive wave (Eβ wave) including the particular positions thereof on a temporal axis (information such as amplitudes or frequencies as well as the particular positions on the temporal axis).

Under the condition of a time phase difference of 0.2 seconds or less, attention is given to a time phase difference between the e wave of the fingertip plethysmogram and the posterior inflection point (ventricle initial diastolic phase responsive wave (Eβ wave)) in the second derivative waveform of the reference form of the APW that varies widely regarding the subject A and does not vary widely regarding the subject B. The occurrence of this difference in variation shows that grasping a time phase difference between a fingertip plethysmogram as information about a peripheral system and an APW as information about a part near a central system both resulting from heart rate fluctuation and heart rate variability governed by sympathetic nerves effectively functions as a measuring system to understand a degree of control by sympathetic nerves. To understand the dynamic state of control of a contracting phase and a diastolic phase relatively, it is preferable that the dynamic state be evaluated by comparing two points including the anterior inflection point (ventricle initial contracting phase responsive wave (Eα wave)) in the second derivative waveform of the reference form of the APW and the posterior inflection point (ventricle initial diastolic phase responsive wave (Eβ wave)) in the second derivative waveform of the reference form of the APW and comparing two points including the a and e waves of the fingertip plethysmogram.

As described above, the time phase difference (time phase shift) in FIGS. 18 and 19 was evaluated (degree of variation was evaluated) using the threshold of 0.2 seconds. This threshold was set by assuming an average heart rate as 75 per minute (0.8 seconds for one beat) and determining 0.2 seconds as a boundary condition corresponding to a quarter period of one beat. As described above, regarding the subject A, the center of variation of the time phase of the e wave of the fingertip plethysmogram slightly shifts from that of the posterior inflection point (ventricle initial diastolic phase responsive wave (Eβ wave)) in the second derivative waveform of the reference form of the APW. During the experiment, the subject A was in a relaxed state where sympathetic nerves and parasympathetic nerves appeared in a well-balanced manner. This is considered to show that the appearance of sympathetic nerves and parasympathetic nerves in a well-balanced manner acts to affect the dynamic state of the fingertip plethysmogram relating to a peripheral system. The aforementioned time phase shift between the e wave of the fingertip plethysmogram and the posterior inflection point (ventricle initial diastolic phase responsive wave (Eβ wave)) in the second derivative waveform of the reference form of the APW shows a normal dynamic state.

As shown in FIG. 17(f), regarding the subject B, the power spectrum of heart beat is lower than that of the subject A. The subject B was in a state during the experiment where the subject B was relaxed more deeply than the subject A. As shown in FIG. 19, regarding the subject B, both a time phase shift between the posterior inflection point (ventricle initial diastolic phase responsive wave (Eβ wave)) in the second derivative waveform of the reference form of the APW and second heart sound and a time phase shift between the posterior inflection point (ventricle initial diastolic phase responsive wave (Eβ wave)) in the second derivative waveform of the reference form of the APW and the e wave of the fingertip plethysmogram are smaller. Specifically, first heart sound did not vary widely as shown in FIG. 17(h) and second heart sound was low entirely as shown in FIG. 13. As shown by an arrow of FIG. 15, at the same frequency, the amplitude of the APW is smaller in part than that of the subject A.

Thus, a difference in a state of a sympathetic nervous system between the subjects A and B during the experiment is considered to cause the aforementioned variations in time phase difference. It is thus understood that the time phase difference analyzing means 642 set in the state analyzing means 64 can be used to set a relationship of a time phase difference between a fingertip plethysmogram and an APW for determining a state.

Example 2

Example 1 clearly shows that a time phase difference between a fingertip plethysmogram and an APW indicates a difference in the state of a sympathetic nervous system. Example 2 is to examine how this difference in the state of a sympathetic nervous system is reflected in an original waveform of an APW from the body trunk biological signal measuring device 1 and an original waveform of a fingertip plethysmogram.

Figure 20:
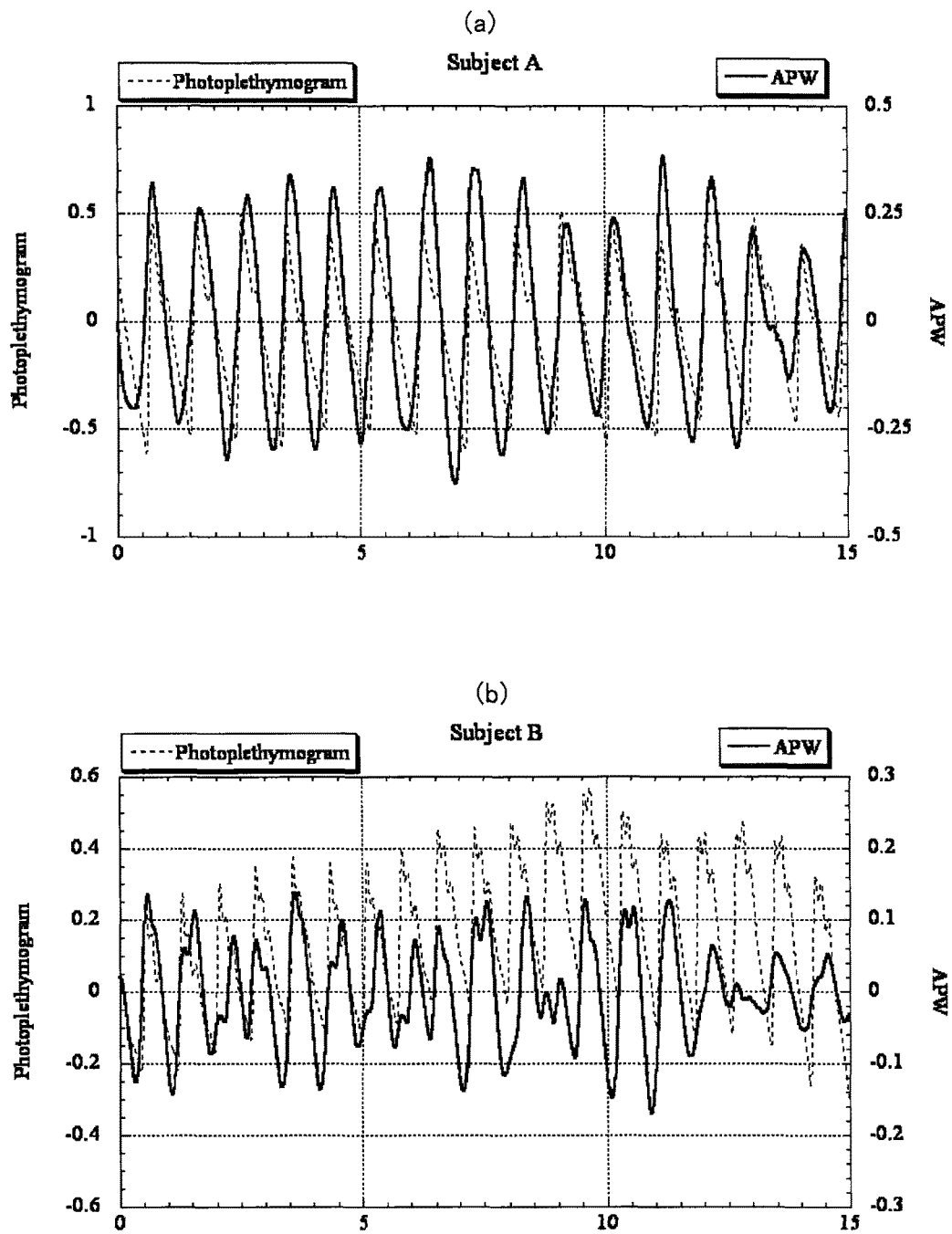
FIGS. 20(a) and (b) show original waveforms of a fingertip plethysmogram and an APW about the subject A and those of a fingertip plethysmogram and an APW about the subject B respectively that are obtained in 15 seconds in an experiment.

FIGS. 20(a) and (b) show original waveforms of the subjects A and B respectively obtained during 15 seconds in an experiment. As clearly seen from these drawings, regarding the subject A, a fingertip plethysmogram and an APW are substantially the same in frequency and amplitude. In contrast, regarding the subject B, a fingertip plethysmogram and an APW are substantially the same in frequency whereas the amplitude of the APW is shown to be smaller than that of the fingertip plethysmogram. As described above, the APW contains information about the contracting phase and the diastolic phase of a ventricle and elasticity information about a vascular wall functioning as an auxiliary pump for circulation. Thus, such a large difference of the amplitude of the APW from that of the fingertip plethysmogram as a peripheral biological signal is considered to indicate a probability of cardiovascular abnormality. Actually, the subject B suffers from a mild cardiovascular disease. Giving attention to a time phase difference as in Example 1 can only estimate a state of a sympathetic nervous system showing that the subject B was in a deeply relaxed state. Meanwhile, this addition of a difference in an original waveform to criteria for determination allows estimation of cardiovascular abnormality. Thus, by providing the original waveform comparing and analyzing means 641 shown in FIG. 4 and setting a certain threshold for a difference in amplitude as described above, the presence or absence of cardiovascular abnormality can be determined automatically.

Example 3

Relationship of Time Phase Difference Between Fingertip Plethysmogram and APW with Different Index of Sympathetic Nerve As shown in Example 1, a time phase difference between a fingertip plethysmogram and an APW indicates a difference in the state of a sympathetic nervous system. To show this issues more explicitly, in Example 3, experiment was conducted to verify correlation with publicly-known different indexes of sympathetic nerves functioning as an evaluation index.

Method of Experiment

Figure 21:
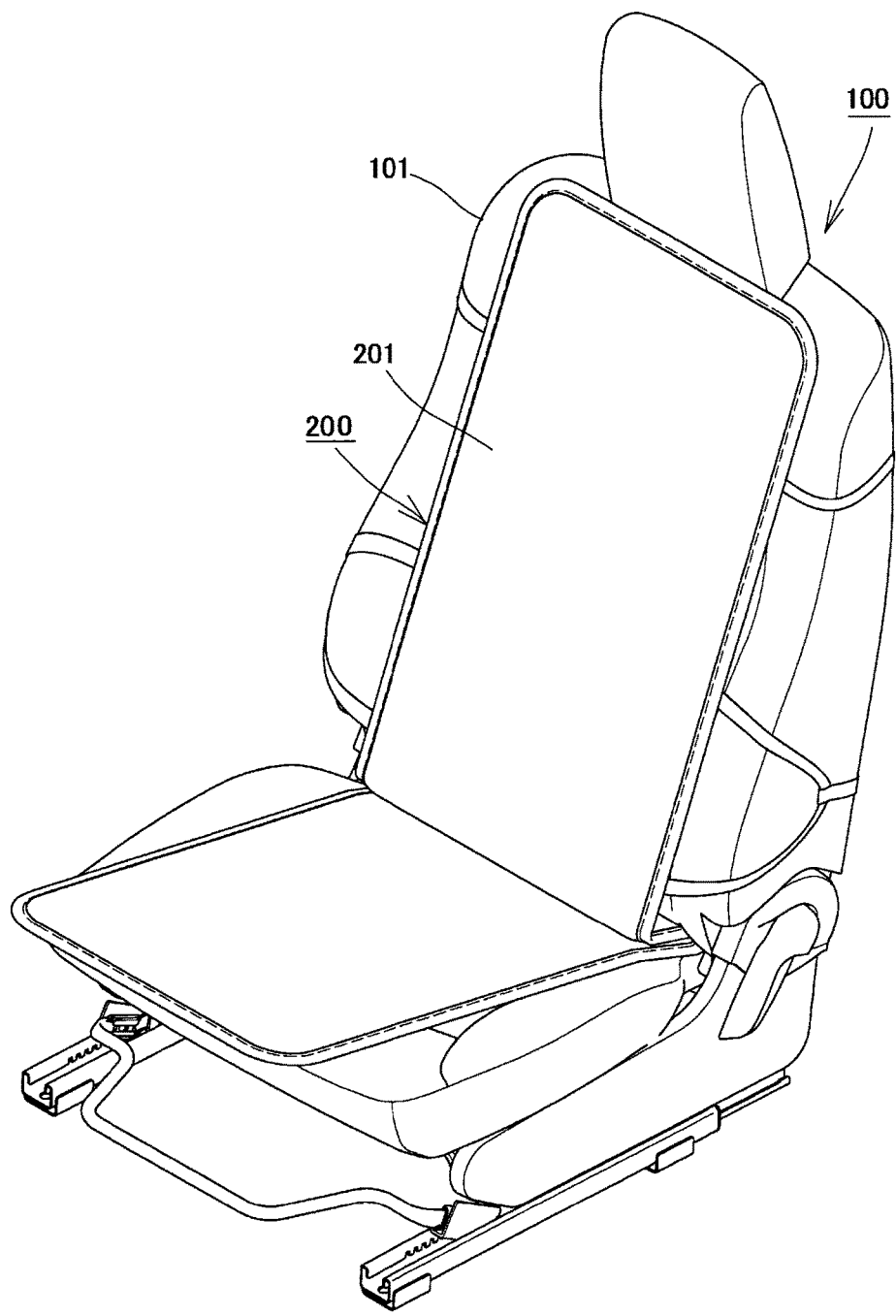
FIG. 21 is a perspective view showing a state where a seat cushion used in an experiment of Example 3 having a back support cushion member in which the body trunk biological signal measuring device is incorporated is attached to an automobile seat.
Figure 22:
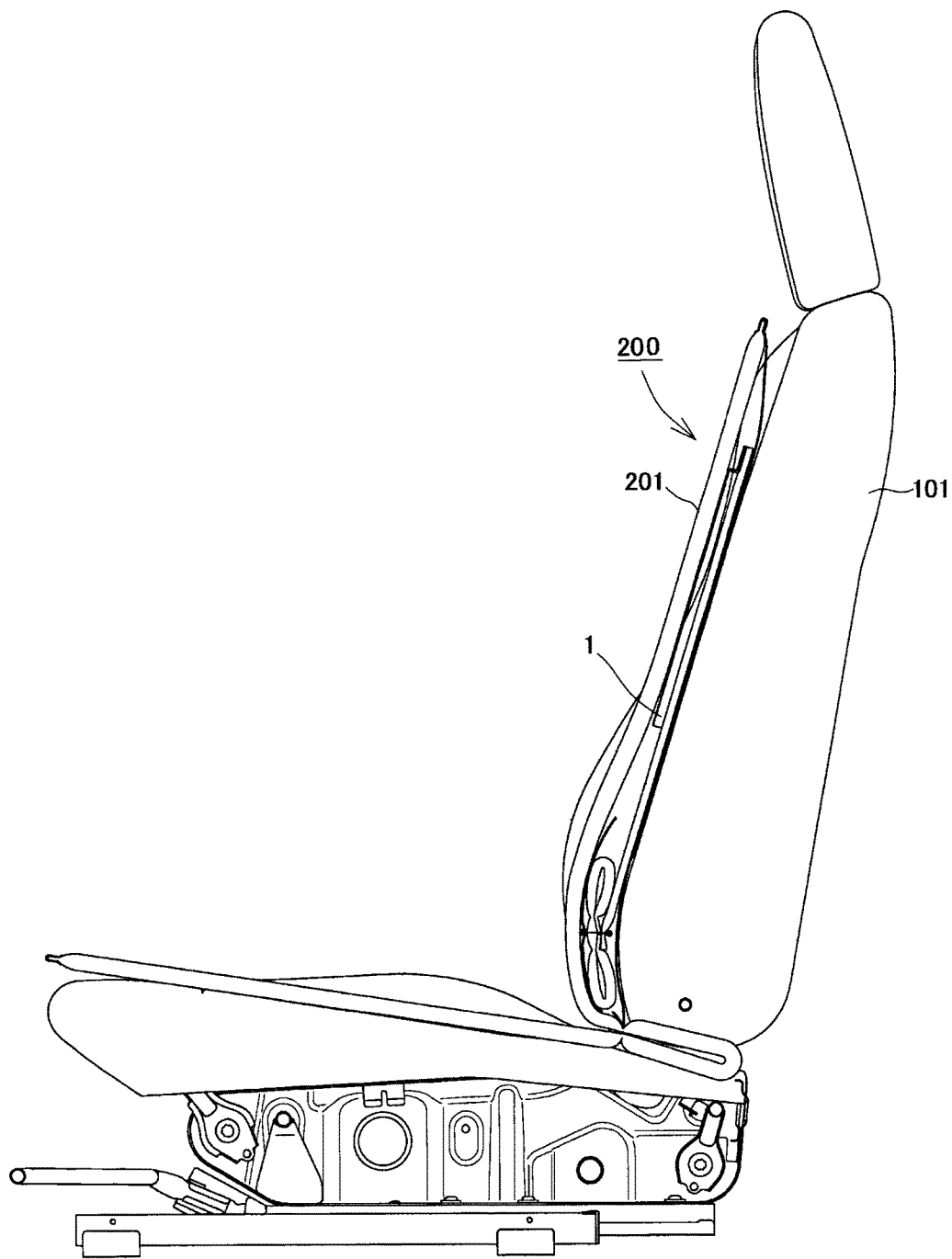
FIG. 22 is a side view of FIG. 21.
Figure 23:
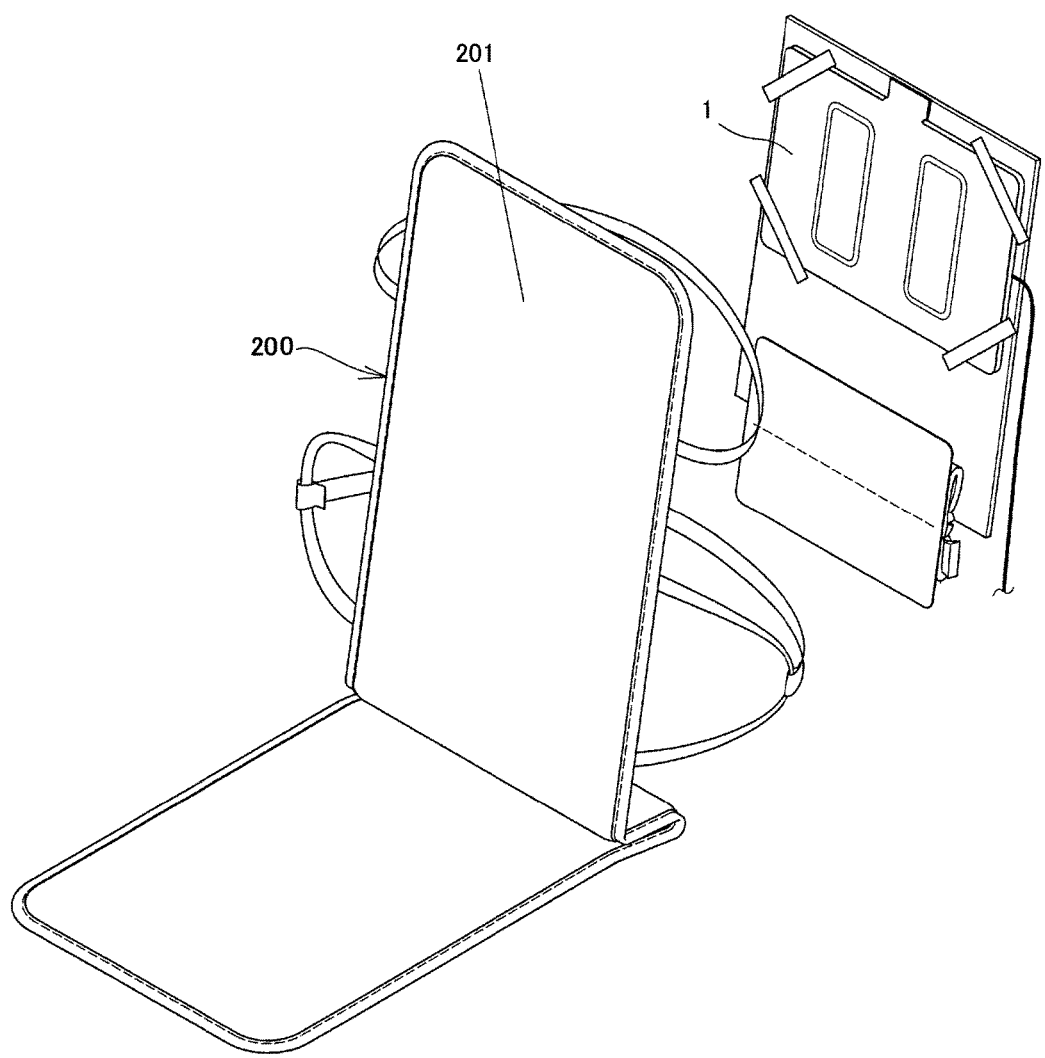
FIG. 23 shows the arrangement of the body trunk biological signal measuring device and that of the seat cushion relative to each other.

A subject was seated on an automobile seat 100 in a laboratory. To see change in the state of the subject from awaking to sleeping, an experiment was conducted on condition that the subject was obliged to continue wakefulness in the first 30 seconds with his or her eyes open and the subject was allowed to shift to a sleeping state in the last 30 minutes. As shown in FIGS. 21 to 23, the automobile seat 100 includes a seat cushion 200 attached to a surface of a seat back 101. The seat cushion 200 has a back support cushion member 201 in which the body trunk biological signal measuring device 1 of FIG. 1 is incorporated. A precision electroencephalograph and a fingertip plethysmogram meter were attached to the subject to measure an APW, a brain wave, and a fingertip plethysmograms synchronously. Six men in an age range from 25 to 47 were subjected to the experiment.

Result of Experiment

The following shows a result of the experiment conducted on a subject C in his thirties who maintained wakefulness while counteracting sleepiness in the first half of the experiment, could not sleep in the cold in the last half of the experiment, and fell asleep thereafter just before the end of the experiment. Information about the state of the subject was confirmed based on a brain wave, view by a person in charge of the experiment, and thought given by the subject.

FIGS. 24(a) to (g) show measurement results obtained by using the aforementioned different indexes of sympathetic nerves. FIG. 24(a) shows a waveform indicating a sleep stage of the subject obtained from the precision electroencephalograph. FIG. 24(b) shows the state of change in an index of a sympathetic nervous system obtained as a result of wavelet analysis on a fingertip plethysmogram. FIG.

24(c) shows a slope time-series waveform of a maximum Lyapunov index determined by obtaining a time-series waveform of a power value from a time-series waveform of a fingertip plethysmogram, then obtaining a slope of the power value by a least square method, obtaining a time-series waveform of the power value by movement calculation made in a predetermined time window, conducting chaos analysis on the slope time-series waveform of the power value and the time-series waveform of the fingertip plethysmogram, and then making movement calculation in a predetermined time window (the slope time-series waveform of the power value of the fingertip plethysmogram and the slope time-series waveform of the maximum Lyapunov index are collectively called a "slope time-series waveform of the fingertip plethysmogram"). FIGS. 24(d) and (e) show time-series changes of distributions of three low-frequency fluctuation signals (about 0.0017 Hz, about 0.0035 Hz, and about 0.0053 Hz) determined by obtaining frequency slope time-series waveforms from a zero-cross time interval and a peak time interval of a time-series waveform of an APW respectively, and then conducting frequency analysis on these frequency slope time-series waveforms. These three fluctuation signals are in a typical VLF or ULF band contributing to the maintenance of homeostasis of a human being suggested by the applicant of this application for example in Japanese Patent Application No. 2011-43428. FIGS. 24(f) and 24(g) show results of frequency analysis conducted on a time-zone basis on the slope time-series waveform of the power value and the slope time-series waveform of the maximum Lyapunov index respectively shown in FIG. 24(c).

The measurement result from the precision electroencephalograph in FIG. 24(a) shows that the subject C in his thirties maintained wakefulness during 1800 seconds in the first half of the experiment, repeated sleep stages 1 and 2 and interrupted sleep for 25 minutes before elapse of 3300 seconds, and fell asleep in a period after 3300 seconds.

The wavelet analysis result of the fingertip plethysmogram in FIG. 24(b) shows that burst waves indicating stimulation of a sympathetic nervous system appeared frequently during 1600 seconds in the first half of the experiment indicated as "I" in the drawing, the function of the sympathetic nervous system reduced while a parasympathetic nervous system became predominant in a period indicated as "II" in the drawing after 1800 seconds, and the function of the parasympathetic nervous system was stimulated further in a period indicated as "III" in the drawing after 3300 seconds.

The slope time-series analysis result of the fingertip plethysmogram in FIG. 24(c) shows that the subject C resisted falling asleep in a time zone after 1000 seconds and before 1400 seconds, the subject C was in a relaxed state in a period from 1400 to 2400 seconds, a sleep prediction phenomenon appeared in a period after 2400 seconds and before 3000 seconds, and the subject C shifted to a sleeping state after 3300 seconds.

The distribution time-series waveforms of APWs in FIGS. 24(d) and (e) show that an impending sleeping phenomenon appeared before or after elapse of 2600 seconds and there was falling asleep confirmed before or after 3400 seconds.

The frequency analysis results about the slope time-series waveform of the fingertip plethysmogram in FIGS. 24(f) and (g) show that a peak was generated in the power peak value in the ULF band of 0.0033 Hz or less in a period from 1800 to 3000 seconds, and a peak was generated in each of the power value and the maximum Lyapunov index in the VLF band from 0.0033 to 0.0055 Hz, indicating the appearance of a sleep prediction phenomenon. Further, in a period from 3000 to 3600 seconds, the amplitude of the power value became a quarter or less of the amplitude of the time-series waveform in the first half in a period from 900 to 1800 seconds, indicating entry into a sleeping state. The subject C was in a wakeful state in a period from 0 to 900 seconds. Meanwhile, the presence of the peak in the VLF band observed in the frequency analysis result about the power value suggests that the subject C was relaxed. Regarding this period from 900 to 1800 seconds, the power value had a peak in a band with respect to 0.0055 Hz, and the maximum Lyapunov index had two peaks in a power spectrum at 0.0033 Hz and 0.0055 Hz. As a result, the subject C was estimated to be in a state where the subject C was resisting falling asleep.

As understood from above, the indexes of FIGS. 24(a) to (g) all show that the subject C maintained wakefulness in the first half of the experiment in a period before 1800 seconds, that a sleep prediction phenomenon appeared while the subject C counteracting sleepiness gradually, and that the subject C fell asleep before or after 3300 seconds.

FIGS. 25(a) to (d) show analysis results obtained by the time phase difference analyzing means 642 of one embodiment of this invention using a difference between the time phase of a fingertip plethysmogram and a time phase obtained from a second derivative waveform of the reference form of an APW. The horizontal axis represents a time phase difference (a–Eα) and the vertical axis represents a time phase difference (e–Eβ).

As seen from the results of the different indexes of sympathetic nerves in FIG. 24, a period from 15 to 40 seconds shown in FIG. 25(a) is a time zone where a sympathetic nervous system and a parasympathetic nervous system are determined to appear to the substantially same degree so that the subject C is determined to be in a state not feeling exhausted. As seen from the results about the different indexes of sympathetic nerves in FIG. 24, a period from 1280 to 1305 seconds shown in FIG. 25(b) is a time zone where the function of the sympathetic nervous system is determined to be stimulated. As seen from the results about the different indexes of sympathetic nerves in FIG. 24, a period from 2610 to 2635 seconds shown in FIG. 25(c) is a time zone where the function of the sympathetic nervous system is determined to be reduced. As seen from the results of the different indexes of sympathetic nerves in FIG. 24, a period from 3450 to 3475 seconds shown in FIG. 25(d) is a time zone where the function of sympathetic nerves is determined to be reduced while the parasympathetic nervous system is predominant.

Comparing FIGS. 25(a) to 25(b) shows that a degree of dispersion (degree of convergence) of coordinate points differs among these drawings. Specifically, in FIG. 25(a), coordinate points gather in a certain range and a time phase difference is dispersed gently. In contrast, FIG. 25(b) shows relatively high tendency toward dispersion, indicating a large time phase difference. In each of FIGS. 25(c) and (d), a time phase difference is small, so that coordinate points are dispersed to an extremely low degree and the coordinates points seem to converge on substantially one place. Thus, by making the time phase difference analyzing means 642 determine the aforementioned degree of dispersion of coordinate points using an area as a reference area where the coordinate points are dispersed, for example, the following determinations can be made automatically: if coordinate points are in an area smaller than a certain area, the function of sympathetic nerves is determined to be reduced as shown in FIGS. 25(c) and (d); if coordinate points are in a certain area larger than this area, a sympathetic nervous system and a parasympathetic nervous system are determined to be relatively well balanced as shown in FIG. 25(a); and if coordinate points are in a still larger area, the function of the sympathetic nervous system is determined to be stimulated as shown in FIG. 25(b). Certainly, these are merely examples. A state can be classified in more detail, or a different algorithm may be used to determine a degree of dispersion.

Table 1 shows a result obtained by summarizing correlation between the aforementioned result of determination by the time phase difference analyzing means 642 and the index of sympathetic nerves determined by the wavelet analysis in FIG. 24(b) about each of the six subjects.

More specifically, in the analysis result of FIG. 24(b) about each subject, four points were extracted indicating a state where the function of sympathetic nerves is stimulated or a state where the function of sympathetic nerves is reduced. A time phase difference between a fingertip plethysmogram and an APW in each time zone where such a state was extracted was obtained as shown in FIG. 25. Results are shown in a 2 by 2 cross table.

TABLE 1

| | | FINGERTIP-APW TIME PHASE | |
|---|---|---|---|
| | | DISPERSION | CONVERGENCE |
| SYMPATHETIC NERVE (FINGERTIP PLETHYSMOGRAM) | STIMULATED | 7 | 2 |
| | REDUCED FUNCTION | 2 | 13 |

Referring to Table 1, "DISPERSION" indicates a case where coordinate points are dispersed in an area substantially the same as the area shown in FIG. 25(a), "CONVERGENCE" means a case where coordinate points are dispersed in an area substantially the same as or smaller than the area shown in FIG. 25(c) or (d), "STIMULATED" corresponds to the state of I shown in FIG. 25(b), and "REDUCED FUNCTION" corresponds to the states of II and III shown in FIG. 24(b).

The results of Table 1 were subjected to a chi-square test. A resultant P value was 0.0016 considerably lower than 0.05. Thus, significant correlation was confirmed between a way of dispersion of coordinate points based on a time phase difference between a fingertip plethysmogram and an APW and the publicly-known different indexes of sympathetic nerves.

The foregoing discussion makes it clear that in a steady state where sympathetic nerves and parasympathetic nerves are active to the substantially same degree in a wakeful state, coordinate points based on a time phase difference between a fingertip plethysmogram and an APW tend to be dispersed gently (see FIG. 25(a)), stimulation of the activity of the sympathetic nerves resulting from counteracting sleepiness increases this time phase difference to disperse coordinate points more widely (see FIG. 25(b)), and if the activity of the sympathetic nerves is reduced and a shift to a sleeping state is made, the parasympathetic nerves become predominant and the time phase difference becomes substantially zero, thereby dispersing coordinate points to an extremely low degree (see FIGS. 25(c) and (d)). Thus, setting a value to become a threshold for a degree of dispersion of coordinate points based on this time phase difference as described above allows the time phase difference analyzing means 642 shown in FIG. 4 to determine the state of a human being in more detail.

Example 4

It is preferable that the state analyzing means 64 include the vascular information and time phase difference analyzing means 643. As described above, the vascular information and time phase difference analyzing means 643 is to make a plot by placing the time phase difference (a–Eα) or the time phase difference (e–Eβ) grasping information about a sympathetic nervous system on one axis and the wave height ratio (e/a value) on a different axis, thereby obtaining state information about a human being containing peripheral information. This example is intended to verify this issue.

The verification was conducted using data about the healthy male subject C in his thirties obtained in Example 3, and data about Mr. Y who was 62 years old and data about Mr. Yoshito Fujita who was 86 years old at the time of data measurement to extract an APW (from 2010 to 2011). Like in Example 1, a face-up laying posture was adopted as an experimental condition.

FIGS. 26 to 29 show the data about the subject C. Respective views (b) of FIGS. 26 to 29 show output results by the time phase difference analyzing means 642 that correspond to the same data as that of FIGS. 25(a) to (d). As described above, FIG. 26(b) shows a time zone where a sympathetic nervous system and a parasympathetic nervous system are determined to appear to the substantially same degree. FIG. 27(b) shows a time zone where the function of the sympathetic nervous system is determined to be stimulated. FIG. 28(b) is a time zone where the function of the sympathetic nervous system is determined to be reduced. FIG. 29(b) is a time zone where the function of sympathetic nerves is determined to be reduced while the parasympathetic nervous system is predominant.

The view (a) of each drawing shows an output result by the vascular information and time phase difference analyzing means 643. Referring to FIG. 27(a), while the function of the sympathetic nervous system is stimulated, dispersion to the maximum degree in the direction of the horizontal axis (axis of time phase difference (a–Eα) or time phase difference (e–Eβ)) is observed. Referring to FIGS. 28(b) and 29(b), while the function of the sympathetic nervous system is reduced, dispersion to the minimum degree in the horizontal axis direction is observed. Referring to FIG. 26(b), while the sympathetic nervous system and the parasympathetic nervous system appear to the substantially same degree, dispersion in the horizontal axis direction to an intermediate degree is observed. Meanwhile, in either case, wide dispersion in the direction of the vertical axis (axis of wave height ratio (e/a value) of fingertip plethysmogram) is not observed but a degree of dispersion in the vertical axis direction falls within a half of a range of the wave height ratio value e/a (corresponding to one scale shown in the view (a) of each drawing).

FIGS. 30 to 32 show the data about Mr. Y as a subject who was 62 years old at the time of the measurement. Mr. Y had undergone surgery for thyroid cancer at the time of 2010, Sep. 30 when measurement was made for the first time. A metastasis to a lung was also recognized at that time. FIG. 30(b) indicating an output result by the time phase difference analyzing means 642 shows that coordinate points are dispersed widely, meaning stimulation of the function of a sympathetic nervous system. FIG. 31(b) shows that function of the sympathetic nervous system was stimulated comparatively on a later date, 2011, Jan. 21. In a state on 2011, Jul. 17 shown in FIG. 32(b), the sympathetic nervous system and parasympathetic nerves appeared to be substantially same degree. Meanwhile, as seen from comparison of the vascular information and time phase difference analyzing means 643 shown in the respective views (a) of FIGS. 30 to 32, a degree of dispersion in the direction of the vertical axis (wave height ratio) is wider in each view than a degree of dispersion in the data about the healthy male subject C. This is considered to indicate poor balance between a part near a periphery and a part near the center due to stress caused by the disease. It can be understood accordingly that taking the wave height ratio (e/a value) into consideration makes it possible to determine the presence or absence of an external factor due to a disease or the like as well as the state of a sympathetic nervous system. Regarding Mr. Y as a subject, fluctuation in the vertical axis direction tends to reduce with time, so that it can be estimated that Mr. Y tended to get better.

FIGS. 33 to 35 show the data about Mr. Yoshito Fujita as a subject who was 86 years old at the time of the measurement. This subject also suffered from cancer. Data on 2011, Feb. 2 was obtained while Mr. Yoshito Fujita, who had undergone surgery for removing part of bowel cancer, recovered to a level that allowed Mr. Yoshito Fujita to walk in a house and eat in a seated posture during the measurement. A result of FIG. 33(b) obtained by the time phase difference analyzing means 642 shows dispersion to a low degree, meaning a state where a parasympathetic nervous system was predominant. This results from the fact that Mr. Yoshito Fujita was in a gentle resting state. Meanwhile, a result of FIG. 33(a) obtained by the vascular information and time phase difference analyzing means 643 shows wide dispersion in the direction of the vertical axis (axis of wave height ratio e/a). This shows that even in a resting state, Mr. Yoshito Fujita was physically imbalanced due to external stress caused by the disease.

Data on 2011, Mar. 9 shown in FIG. 34 was obtained after Mr. Yoshito Fujita was rehospitalized and underwent treatment for removing accumulated ascites and pleural effusion. The data in FIG. 34(a) shows that dispersion does not become wider in the vertical axis direction. It can be estimated therefrom that Mr. Yoshito Fujita relaxed physically to show temporal tendency toward recovery of his physical state as a result of the treatment for removing ascites and pleural effusion.

Data on 2011, Mar. 21 shown in FIG. 35 was obtained when Mr. Yoshito Fujita did not have much time to live. FIG. 35(b) shows a state where the parasympathetic nervous system was predominant. Meanwhile, FIG. 35(a) shows wide dispersion in the vertical axis direction. This data shows that at this point in time, Mr. Yoshito Fujita was in a state that did not allow any treatment for recovery, meaning that he was physically imbalanced seriously.

As understood from above, by using the time phase difference (a–Eα) or the time phase difference (e–Eβ) between an APW and a fingertip plethysmogram and the wave height ratio (e/a value) of the fingertip plethysmogram, the vascular information and time phase difference analyzing means 643 is allowed to determine the presence or absence of external stress such as a disease leading to physical imbalance as well as the state of a sympathetic nervous system. Regarding the coordinate showing the output result by the vascular information and time phase difference analyzing means 643 in the view (a) of each of FIGS. 26 to 35, the "presence" of an external stress factor such as a disease is determined based on a degree of dispersion in the direction of the axis of the wave height ratio (e/a value). This degree can be set arbitrarily by processing data statistically, for example. In consideration of an individual difference, this degree can certainly be set for each individual. Setting such a threshold allows the vascular information and time phase difference analyzing means 643 to automatically determine the state of a sympathetic nervous system and the presence or absence of stress due to an external factor (such as a disease, alcohol drinking, or drug taking).

Figure 36:
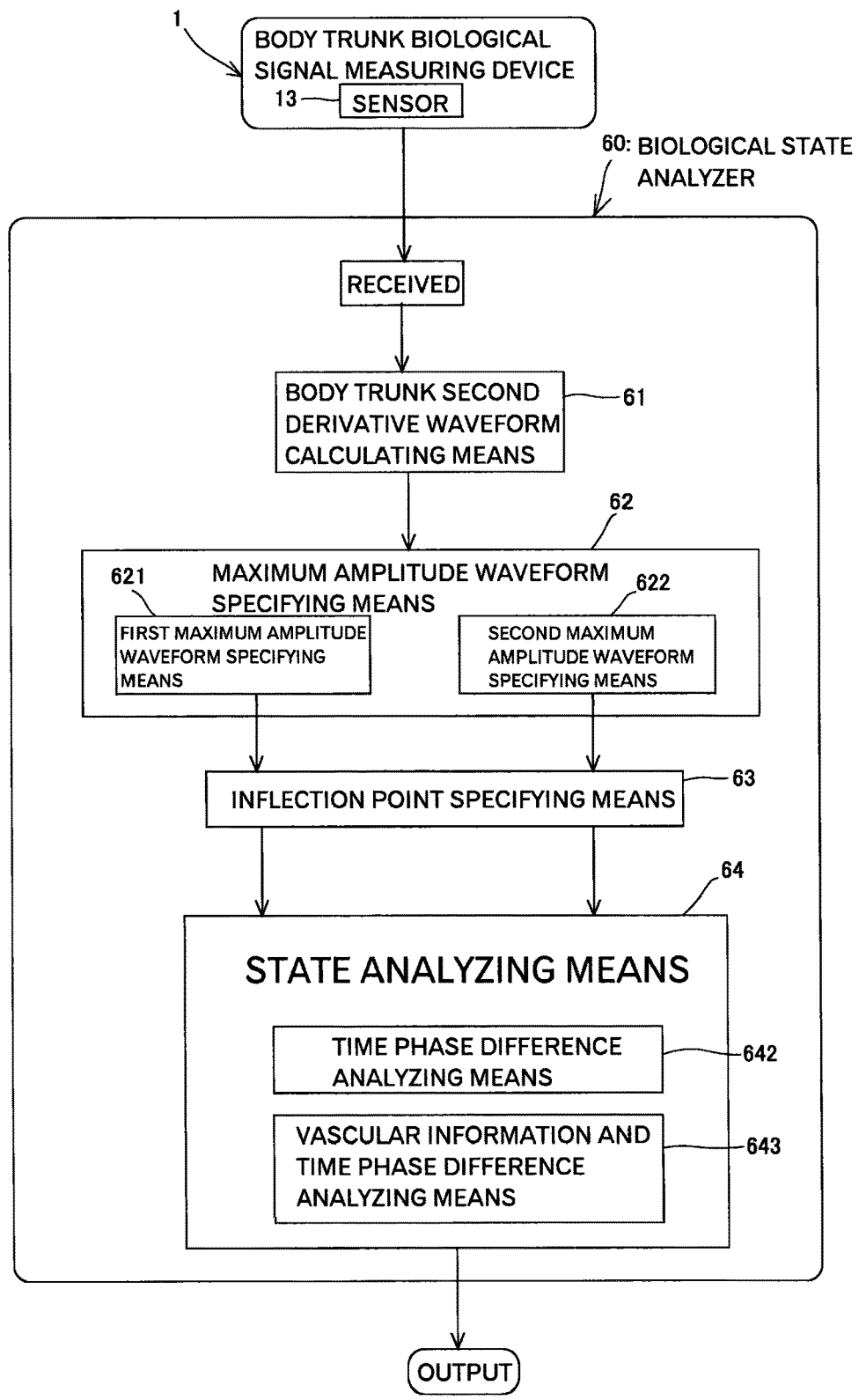
FIG. 36 schematically shows the structure of a biological state analyzer of a different embodiment of this invention.

In the aforementioned embodiment, the first maximum amplitude waveform component specifying means 621 functioning as the maximum amplitude waveform component specifying means 62 inverts a second derivative waveform from the body trunk second derivative waveform calculating means 61, and specifies a maximum amplitude waveform component using the inverted second derivative waveform as a reference waveform. The inflection point specifying means 63 specifies inflection points (ventricle initial contracting phase responsive wave (Eα wave) and ventricle initial diastolic phase responsive wave (Eβ wave)) appearing before and after the maximum amplitude waveform component. As shown in FIG. 36, in this embodiment, second maximum amplitude waveform component specifying means 622 functioning as the maximum amplitude waveform component specifying means 62 is further provided.

The second maximum amplitude waveform component specifying means 622 specifies a waveform component of a maximum frequency of a low frequency a high-frequency component superimposed on a waveform in each period of a second derivative waveform of an inverted form generated by inverting the reference form of the second derivative waveform used by the first maximum amplitude waveform component specifying means 621 to 180 degrees relative to abase line of the reference form (line at a scale 0). In this embodiment, the reference form of a second derivative waveform used by the first maximum amplitude waveform component specifying means 621 corresponds to the state of a second derivative waveform at the time of its output obtained in a time-series manner by the body trunk second derivative waveform calculating means 61. A second derivative waveform used by the second maximum amplitude waveform component specifying means 622 is one generated by inverting a second derivative waveform of the reference form. Specifically, the second derivative waveform used by the second maximum amplitude waveform component specifying means 622 is eventually a second derivative waveform at the time of its output obtained in a time-series manner by the body trunk second derivative waveform calculating means 61.

The inflection point specifying means 63 specifies inflection points in a pair appearing in this order along a temporal axis before and after the maximum amplitude waveform component specified by the second maximum amplitude waveform component specifying means 622. Specifically, the inflection point specifying means 63 specifies the anterior inflection point where an amplitude switches from attenuation to amplification as a fingertip initial contracting phase responsive wave (Pα wave), the posterior inflection point where the amplitude switches from amplification to attenuation as a fingertip initial diastolic phase responsive wave (Pβ wave).

Figure 37:
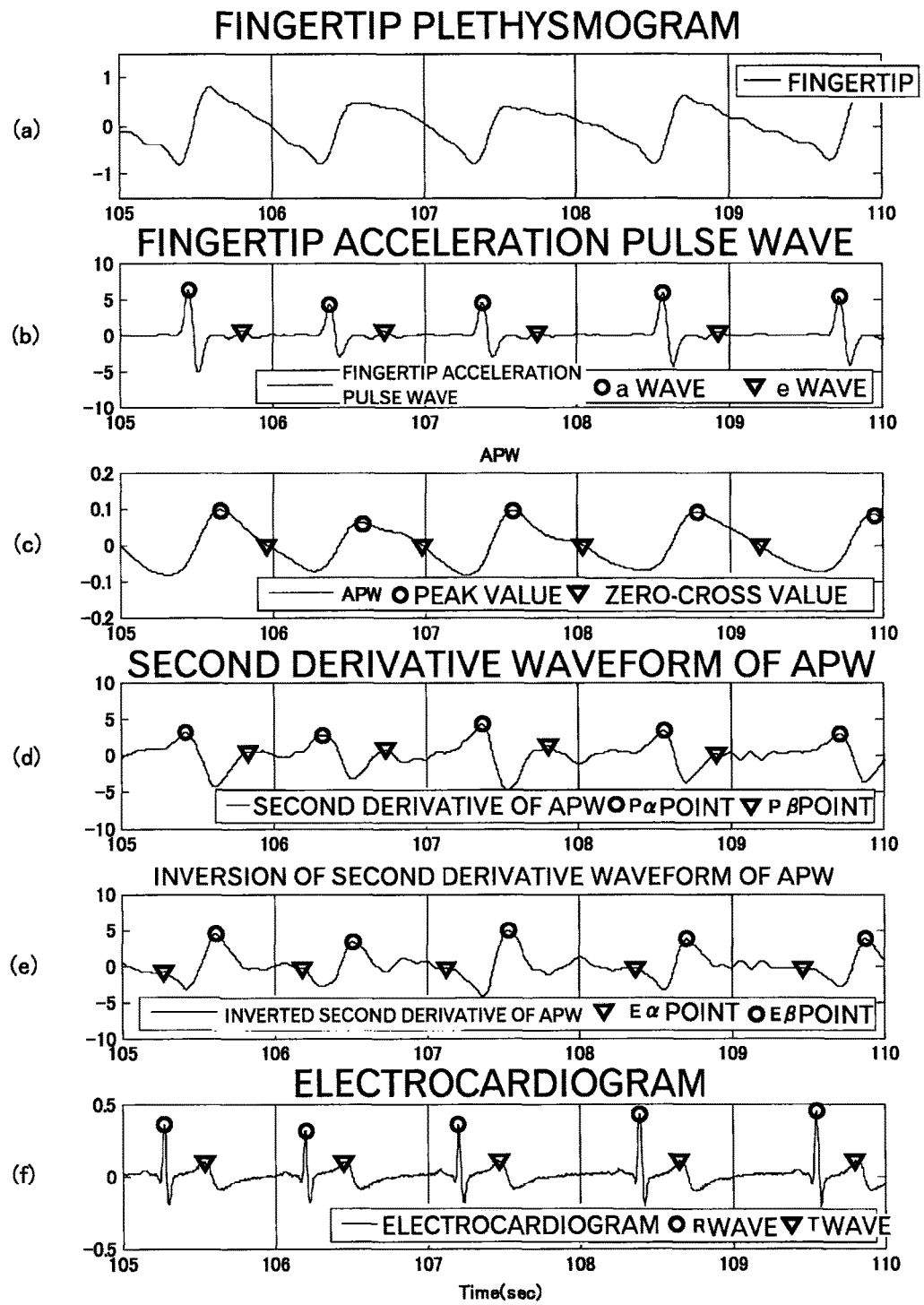
FIGS. 37(*a*) to (*f*) show examples to explain a relationship among a fingertip initial contracting phase responsive wave (Pα wave), a fingertip initial diastolic phase responsive wave (Pβ wave), an a wave and an e wave of a second derivative waveform of a fingertip plethysmogram, a ventricle initial contracting phase responsive wave (Eα wave), a ventricle initial diastolic phase responsive wave (Eβ wave), an R wave in an electrocardiogram (corresponding to first heart sound heard at an initial stage of a contracting phase), and an end stage of a T wave in the electrocardiogram (corresponding to the second heart sound heard at an end stage of the contracting phase).
Figure 38:
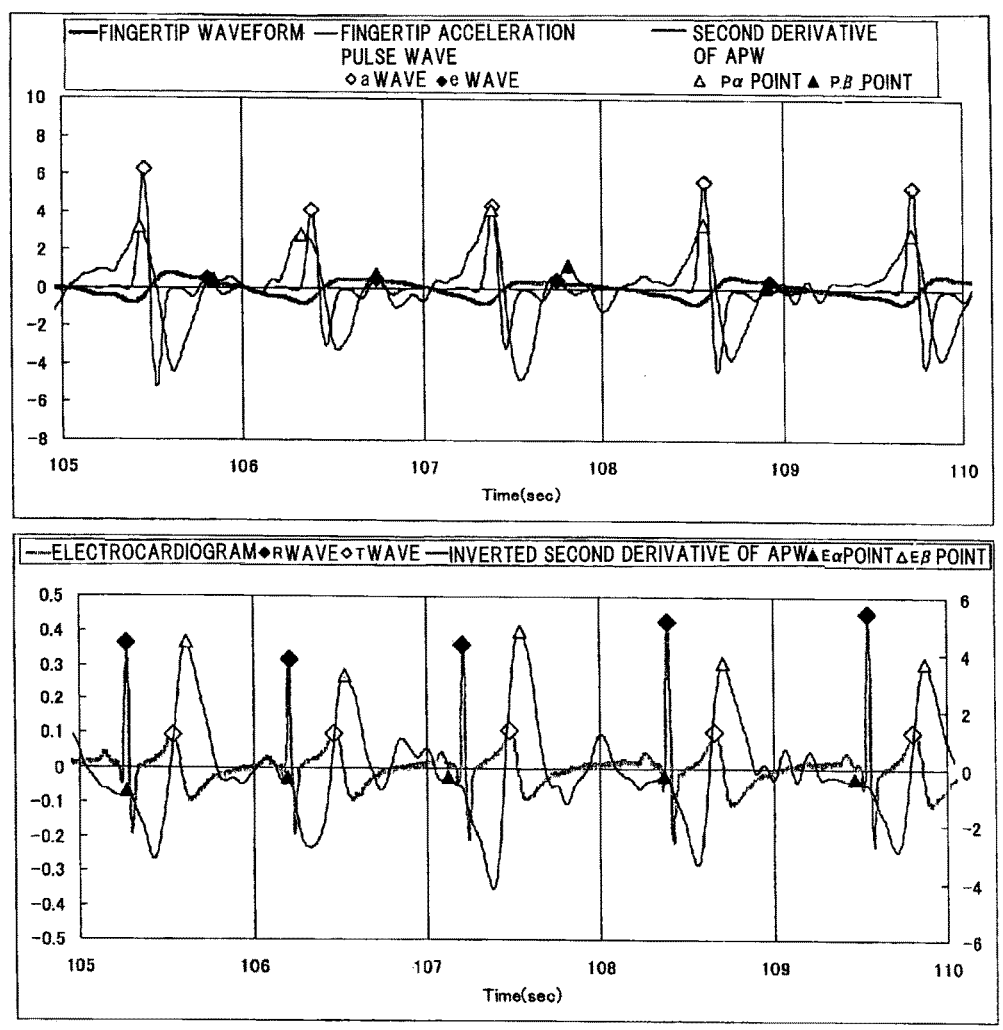
FIG. 38 shows substantially the same substance as in FIG. 37.

The fingertip initial contracting phase responsive wave (Pα wave) and the fingertip initial diastolic phase responsive wave (Pβ wave) as inflection points specified by the second maximum amplitude waveform component specifying means 622 and the inflection point specifying means 63 and appearing before and after the maximum amplitude waveform component correspond to an a wave and an e wave respectively of a second derivative waveform of a fingertip plethysmogram. FIGS. 37 and 38 show examples of these waves. A subject is a female subject NY in her twenties. The fingertip initial contracting phase responsive wave (Pα wave) and the fingertip initial diastolic phase responsive wave (Pβ wave) of FIG. 37(d) obtained by the second maximum amplitude waveform component specifying means 622 and the inflection point specifying means 63 are found to agree with an a wave and an e wave respectively of a fingertip plethysmogram of FIG. 37(b). The ventricle initial contracting phase responsive wave (Eα wave) and the ventricle initial diastolic phase responsive wave (Eβ wave) of FIG. 37(e) described in the aforementioned embodiment obtained by the first maximum amplitude waveform component specifying means 621 are found to agree with an R wave in an electrocardiogram of FIG. 37(f) (corresponding to first heart sound heard at an initial stage of a contracting phase) and an end stage of a T wave in the electrocardiogram of FIG. 37(f) (corresponding to second heart sound heard at an end stage of the contracting phase) respectively.

Figure 39:
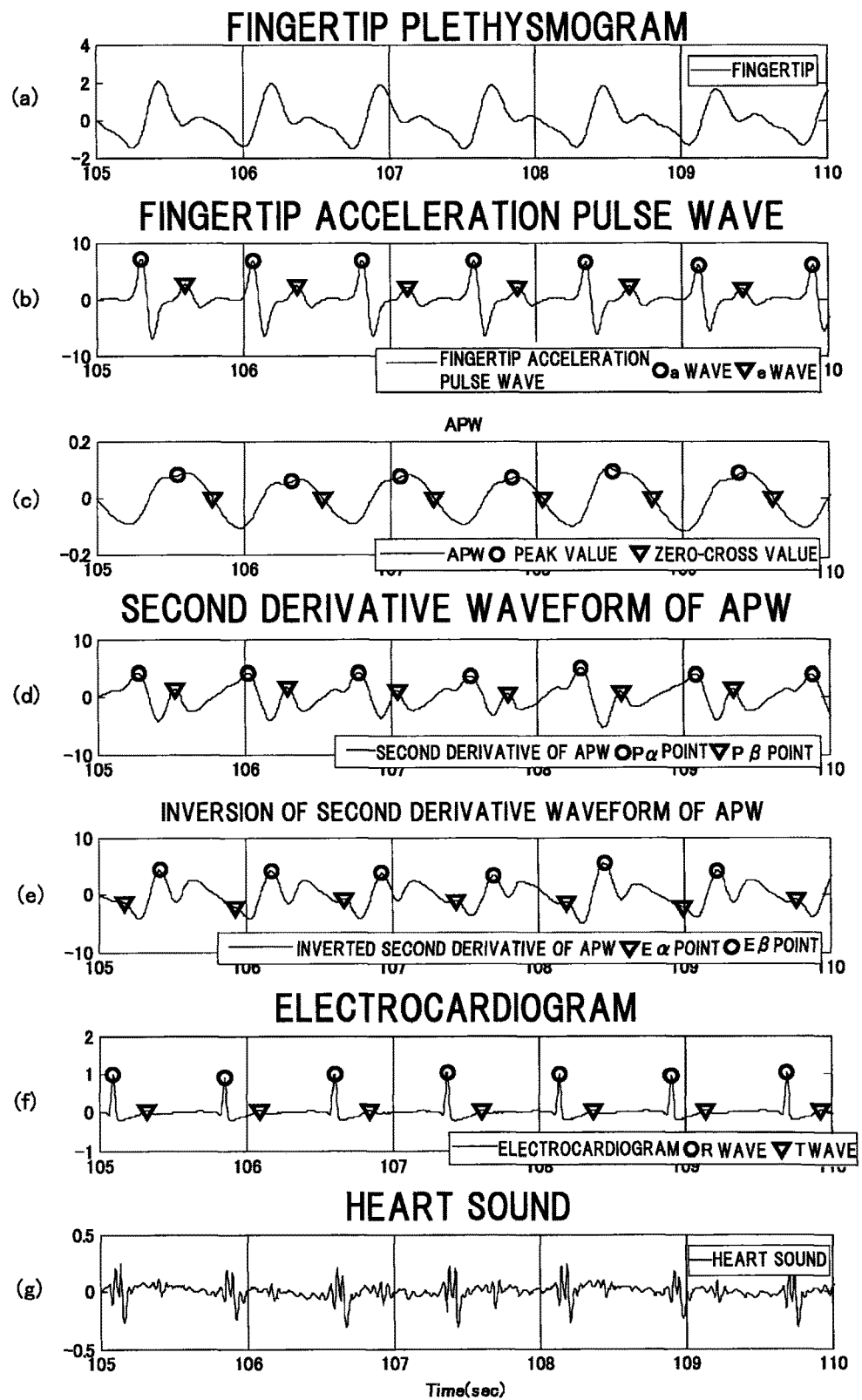
FIGS. 39(*a*) to (*g*) show different examples to explain a relationship among a fingertip initial contracting phase responsive wave (Pα wave), a fingertip initial diastolic phase responsive wave (Pβ wave), an a wave and an e wave of a second derivative waveform of a fingertip plethysmogram, the ventricle initial contracting phase responsive wave (Eα wave), the ventricle initial diastolic phase responsive wave (Eβ wave), an R wave in an electrocardiogram (corresponding to first heart sound heard at an initial stage of a contracting phase), and an end stage of a T wave in the electrocardiogram (corresponding to the second heart sound heard at an end stage of the contracting phase).
Figure 40:
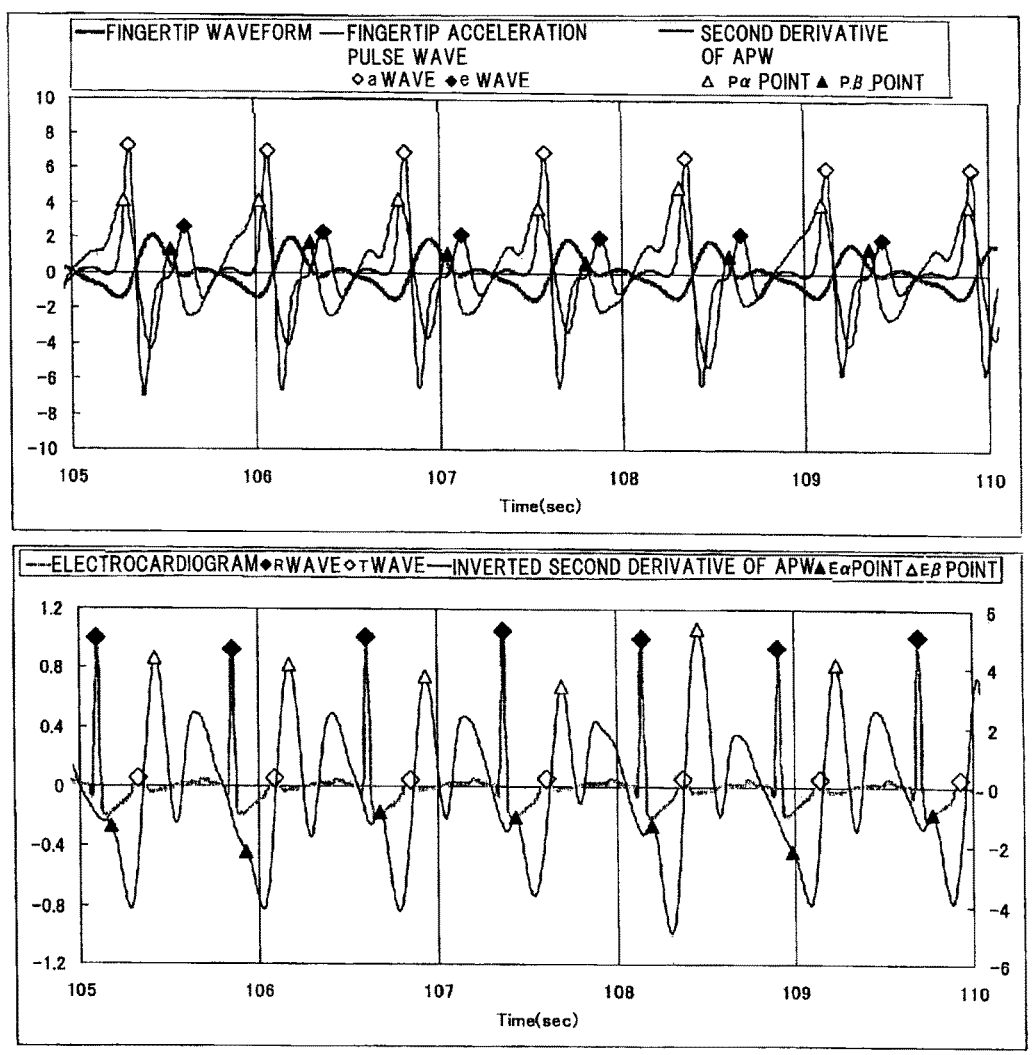
FIG. 40 shows substantially the same substance as in FIG. 38.
Figure 41:
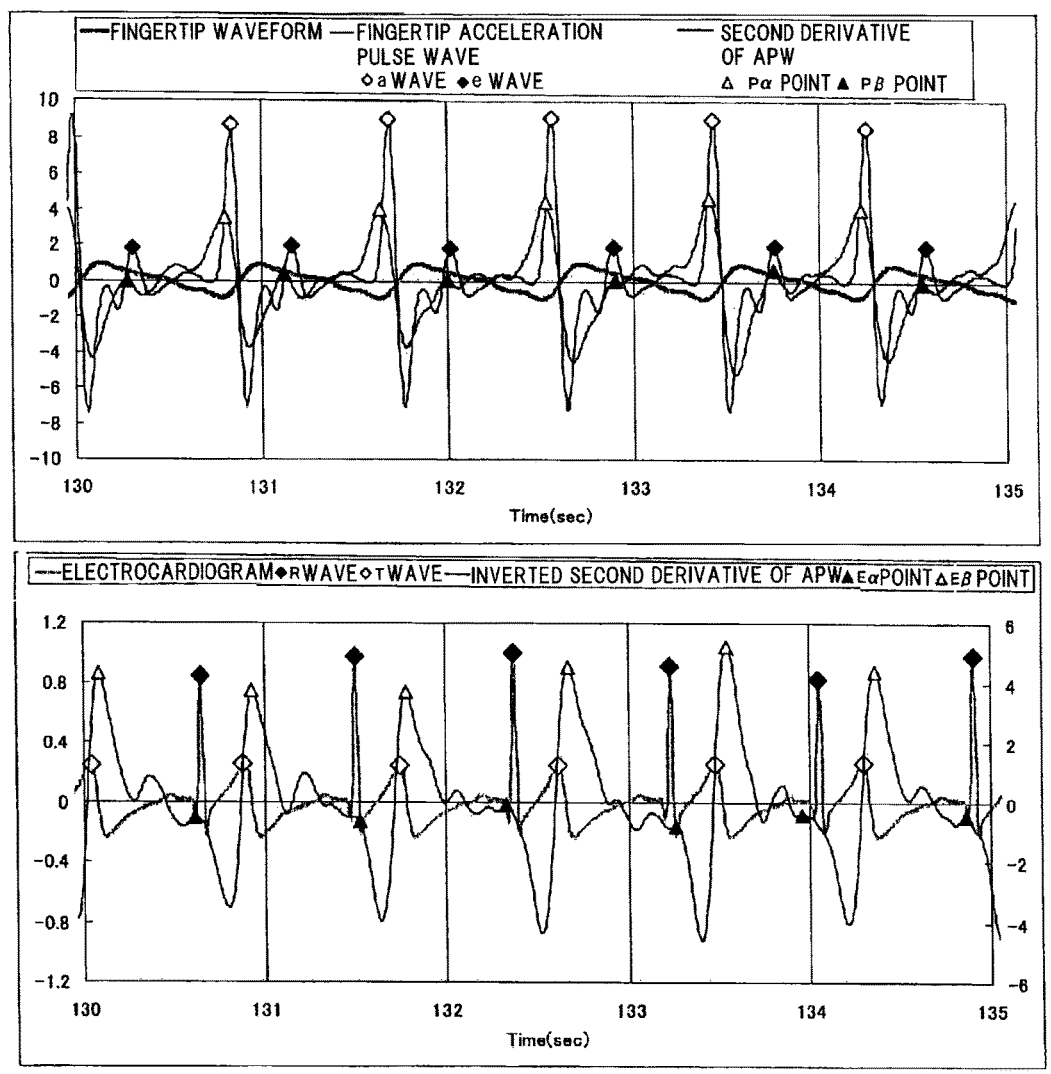
FIG. 41 show still different examples to explain a relationship among a fingertip initial contracting phase responsive wave (Pα wave), a fingertip initial diastolic phase responsive wave (Pβ wave), an a wave and an e wave of a second derivative waveform of a fingertip plethysmogram, the ventricle initial contracting phase responsive wave (Eα wave), the ventricle initial diastolic phase responsive wave (Eβ wave), an R wave in an electrocardiogram, and an end stage of a T wave in the electrocardiogram.

FIGS. 39 and 40 show data about a male subject AT in his twenties. FIG. 41 shows data about a male subject YK in his twenties. Like in the case of the female subject NY shown in FIGS. 37 and 38, regarding both of these male subjects, the fingertip initial contracting phase responsive wave (Pα wave) and the fingertip initial diastolic phase responsive wave (Pβ wave) obtained by the second maximum amplitude waveform component specifying means 622 and the inflection point specifying means 63 are found to agree with an a wave and an e wave of a fingertip plethysmogram respectively. Specifically, an APW contains both information about a part near the center obtained from heart sound or an electrocardiogram and information about a periphery obtained from a fingertip plethysmogram.

As understood from above, in this embodiment, the fingertip initial contracting phase responsive wave (Pα wave) and the fingertip initial diastolic phase responsive wave (Pβ wave) obtained by the second maximum amplitude waveform component specifying means 622 and the inflection point specifying means 63 take the place of an a wave and an e wave respectively of a fingertip plethysmogram used in the aforementioned embodiment.

Specifically, the time phase difference analyzing means 642 plots coordinate points on a coordinate in association with each period. This coordinate has one axis representing the time phase difference (Pα–Eα) between the anterior fingertip initial contracting phase responsive wave (Pα wave) of an APW corresponding to the initial contracting phase positive wave (a wave) of a fingertip plethysmogram and the anterior ventricle initial contracting phase responsive wave (Eα wave) of the APW, and a different axis representing a time phase difference (Pβ–Eβ) between the fingertip initial diastolic phase responsive wave (Pβ wave) of the APW corresponding to the initial diastolic phase positive wave (e wave) of the fingertip plethysmogram and the ventricle initial diastolic phase responsive wave (Eβ wave) of the APW. As a result, like in FIG. 25, a degree of dispersion of coordinates points obtained therefrom can be used to determine the state of a human being.

Figure 42:
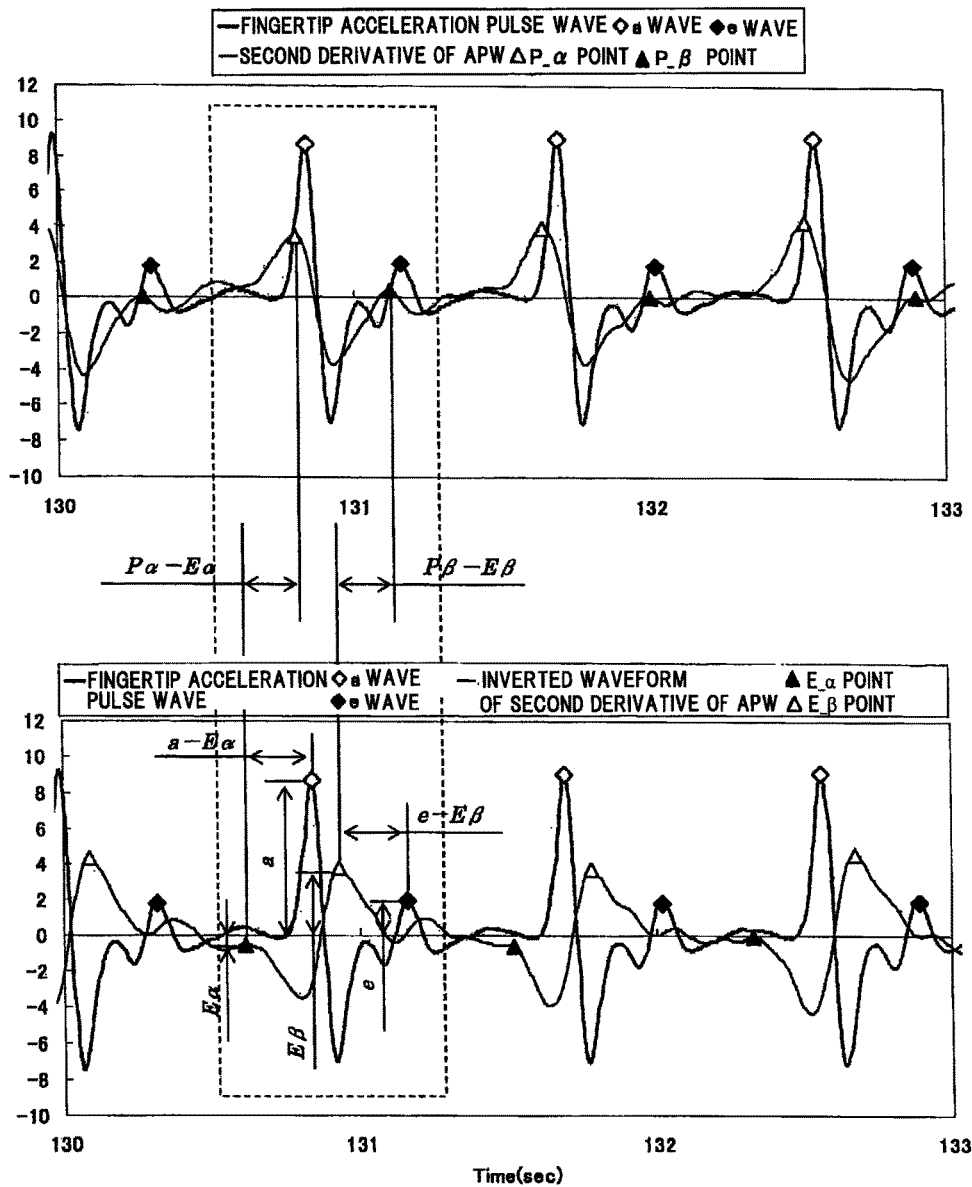
FIG. 42 explains a time phase difference (a–Eα), a time phase difference (e–Eβ), a time phase difference (Pα–Eα), and a time phase difference (Pβ–Eβ).

The vascular information and time phase difference analyzing means 643 uses a time phase difference (Pα–Eα) or a time phase difference (Pβ–Eβ) instead of a time phase difference (a–Eα) or a time phase difference time (e–Eβ) using a fingertip plethysmogram described in the aforementioned embodiment. Vascular information to be used may be the ratio (Eα/Eβ) between the amplitude of the anterior ventricle initial contracting phase responsive wave (Eα wave) and that of the ventricle initial diastolic phase responsive wave (Eβ wave) that respectively correspond to inflection points appearing before and after a maximum amplitude waveform component obtained from the first maximum amplitude waveform component specifying means 621. The vascular information to be used may also be the ratio (Pα/Pβ) between the amplitude of the fingertip initial contracting phase responsive wave (Pα wave) and that of the fingertip initial diastolic phase responsive wave (Pβ wave) that respectively correspond to inflection points appearing before and after a maximum amplitude waveform component obtained from the second maximum amplitude waveform component specifying means 622 (see FIG. 42). As described above, in addition information about the contracting phase and the diastolic phase of a ventricle, an APW contains information such as elasticity information or stiffness information about a vascular wall functioning as an auxiliary pump for circulation or information about a vessel such as its dynamic state that is to change in response to the influence of a foreign matter such as a tumor existing outside the vessel. The amplitude ratio (Eα/Eβ or Pα/Pβ) means a ratio between a value obtained when a blood pressure is at a minimum in a ventricle contracting phase and a value obtained when the blood pressure is at a maximum in a ventricle diastolic phase. A vascular wall of a younger and healthier person makes contraction and dilatation more regularly by means of its elasticity to achieve a stable amplitude ratio. In contrast, a person of a more advanced age is known to increase a blood pressure during a contracting phase and reduce a blood flow into a periphery in a diastolic phase. Specifically, regarding a person of an advanced age or in a bad health state, a vascular wall does not change stably by contraction or dilatation to cause random disturbance. Additionally, the elasticity of a vascular wall of such a person smaller than that of the same person in a younger age makes change by the contraction or dilatation itself smaller. In other words, change in the elasticity of a vascular wall and its vicinity means change in the natural frequency of a body responsive to change in a body tissue such as a vessel or a focus of a disease caused by a age difference or the presence or absence of a disease. This specifically means that an input resulting from pressure fluctuation accompanying contraction or dilatation of a ventricle is reflected at a vascular wall or blood and then propagates to be grasped as acceleration vibration generated in a body trunk, and acceleration response or amplitude response thereof changes in response to the state of a body tissue such as a vessel or a focus of a disease. Thus, by making comparison using the amplitude ratio (Eα/Eβ) between a contracting phase and a diastolic phase, a biological state such as a health state or aging can be shown. Regarding a young and healthy person, dispersion of plotted points changes chaotically in a relatively concentrated range. Regarding an aged person or a person suffering from a disease, points are considered to tend to be dispersed widely and unevenly in a one-dimensional direction. Thus, a non-constant amplitude ratio that changes more widely shows that some adverse effect occurring in a blood flow from the center toward a distal part of a human body acts more seriously.

The vascular information and time phase difference analyzing means 643 of this embodiment plots coordinate points by placing a time phase difference (Pα–Eα) or a time phase difference (Pβ–E) on the horizontal axis and one amplitude ratio (Eα/Eβ or Pα/Pβ) on the vertical axis.

Examples of this plotting correspond to a technique of obtaining output results (4) described later shown in FIGS. 44(*b*), 46(*b*), 48(*b*), 50(*b*), 52(*b*), 54(*b*), 56(*b*), and 58(*b*). As will be described later, FIG. 44(*b*) shows data about Mr. YK as a healthy male subject in his twenties and FIG. 46(*b*) shows data about Ms. NY as a healthy female subject in her twenties, for example. Each of the drawings shows that a time phase difference is small and coordinate points are dispersed not widely in the vertical axis direction but they exist in a relatively concentrated range. In contrast, referring data about Mr. Yoshito Fujita shown in FIG. 48(*b*), for example, coordinate points are found to be dispersed widely in the vertical axis direction. This shows that using the fingertip initial contracting phase responsive wave (Pα wave) and the fingertip initial diastolic phase responsive wave (Pβ wave) specified by the second maximum amplitude waveform component specifying means 622 instead of an a wave and an e wave of a fingertip plethysmogram used in the aforementioned embodiment also allows analysis comparable to that conducted in the aforementioned embodiment. Specifically, this technique requires only data about an APW to analyze a biological state. As described below, for more precise determination, it is preferable that the vascular information and time phase difference analyzing means 643 obtain outputs from combinations of the a and e waves, and the wave height ratio (e/a value) relating to a fingertip plethysmogram, and the Eα and Eβ waves, the Pα and Pβ waves, and an amplitude ratio relating to an APW, and then make determination by comparing these outputs comprehensively.

More specifically, the vascular information and time phase difference analyzing means 643 was set so as to obtain outputs from the following combinations (1) to (4) and resultant outputs were compared mutually.

(1) vertical axis: wave height ratio (e/a value) of fingertip plethysmogram
horizontal axis: time phase difference using fingertip plethysmogram (a–Eα or e–Eβ)

(2) vertical axis: wave height ratio (e/a value) of fingertip plethysmogram
horizontal axis: time phase difference only relating to APW (Pα–Eα or Pβ–Eβ)

(3) vertical axis: amplitude ratio relating to APW (Eα/Eβ)
horizontal axis: time phase difference using fingertip plethysmogram (a–Eα or e–Eβ)

(4) vertical axis: amplitude ratio relating to APW (Eα/Eβ)
horizontal axis: time phase difference only relating to APW (Pα–Eα or Pβ–Eβ)

Figure 44:
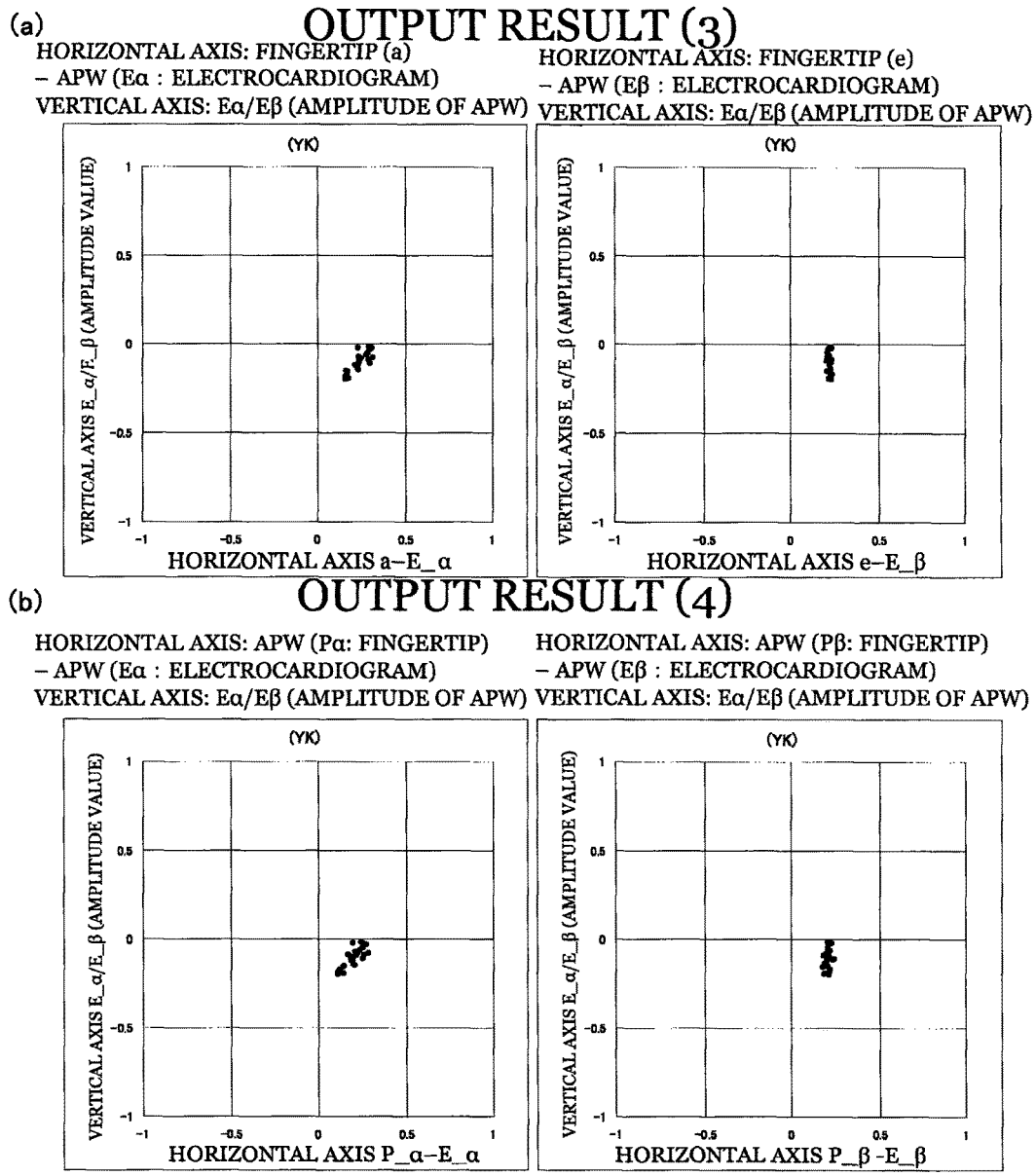
FIG. 44 shows output results (3) and (4) obtained by the vascular information and time phase difference analyzing means using the data about the subject YK.
Figure 45:
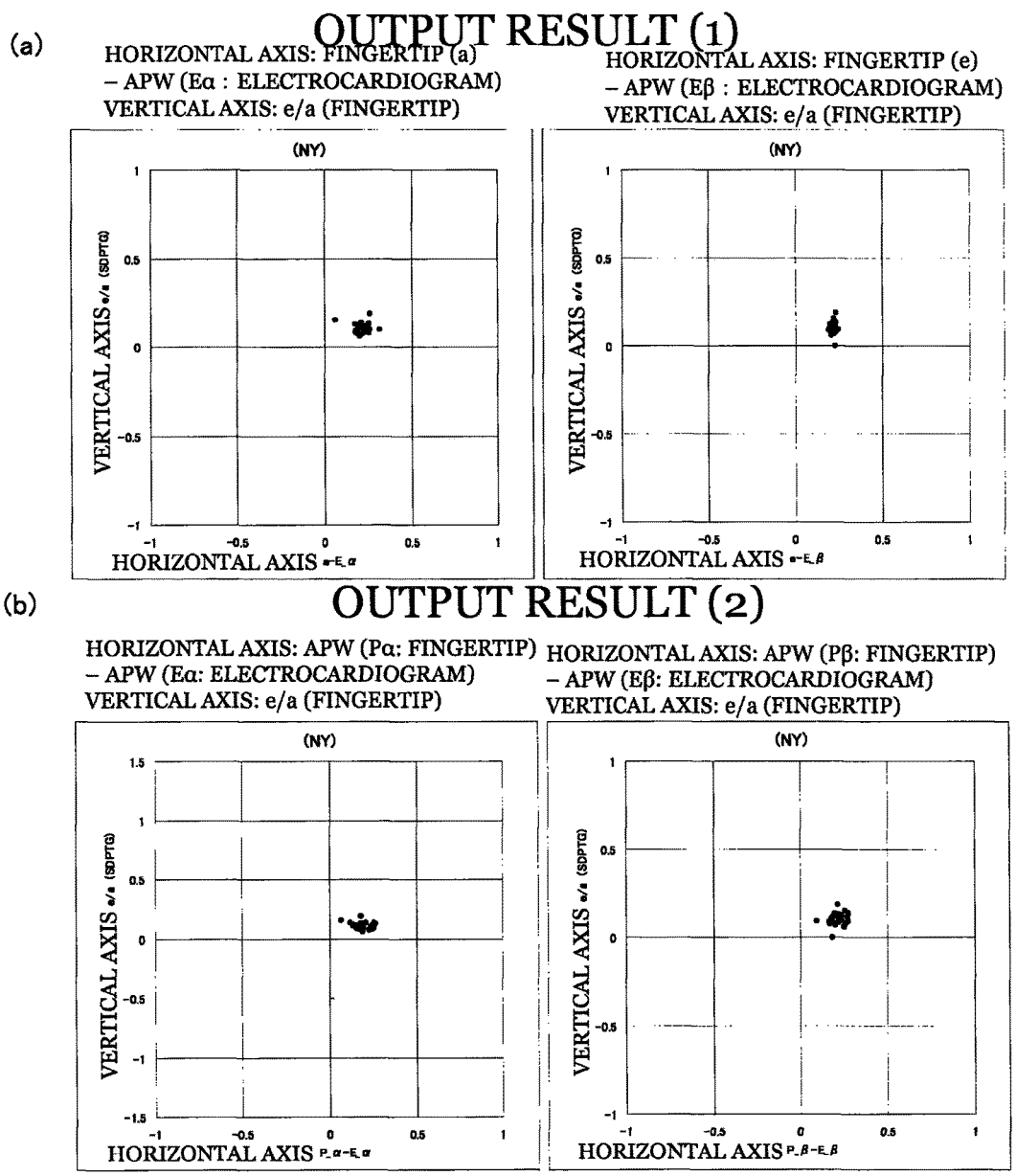
FIG. 45 shows output results (1) and (2) obtained by the vascular information and time phase difference analyzing means using data about a subject NY.

Data about a healthy male subject YK in his twenties shown in FIGS. 43 and 44 is referred to first. A degree of dispersion of coordinate points does not differ largely between the output results (1) and (2). The output results (3) and (4) show that respective time phase differences are small and are substantially the same. This also applies to data about Ms. NY as a female subject in her twenties shown in FIGS. 45 and 46. As seen from comparison between the output results (1) and (2) and comparison between the output results (3) and (4), time phase differences are small and have substantially the same tendency, degrees of dispersions are low, and the dispersions fall within a substantially circular pattern.

Figure 47:
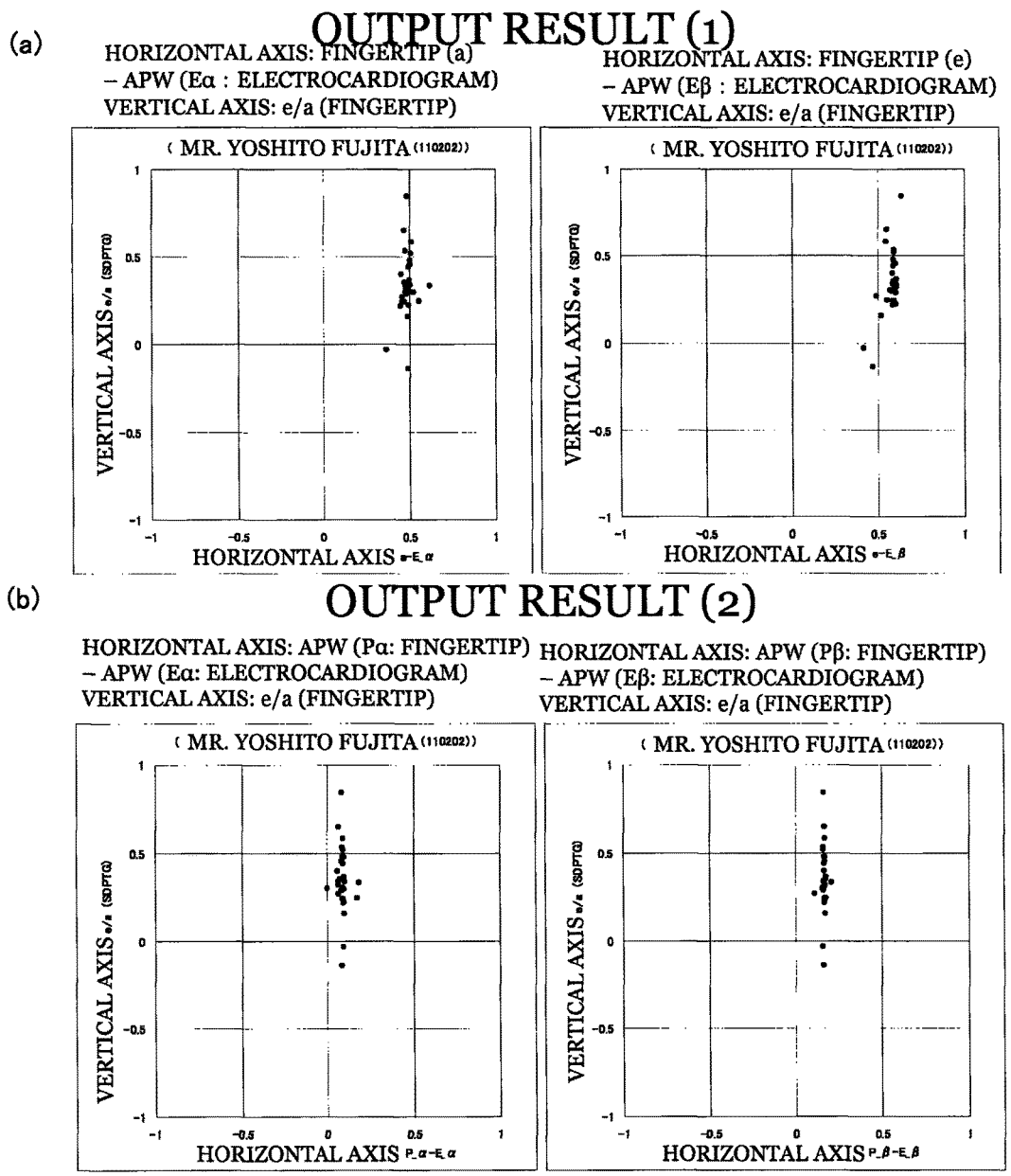
FIG. 47 shows output results (1) and (2) obtained by the vascular information and time phase difference analyzing means using data on 2011, Feb. 2 about a subject, Mr. Yoshito Fujita.

In contrast, data about Mr. Yoshito Fujita in FIGS. 47 and 48 shows that each of the output results (1) to (4) obtained on 2011, Feb. 2 exhibits a high degree of dispersion in the vertical axis direction, as described above. Meanwhile, comparison between the output results (1) and (2) shows that their time phase differences differ from each other significantly. This also applies to comparison of the output results (3) and (4). In either case, the output results (1) and (3) (FIGS. 47(*a*) and 48(*a*)) obtained by placing the time phase difference (a–Eα or e–Eβ) using a fingertip plethysmogram on the horizontal axis are larger in time phase difference than the output results (2) and (4) (FIGS. 47(*b*) and 48(*b*)) respectively obtained by placing a time phase difference only relating to an APW (Pα–Eα or Pβ–Eβ) on the horizontal axis. This results from a difference between an APW as a body trunk biological signal about a part near the center and a fingertip plethysmogram as a biological signal about a periphery (distal end) of a human body. Making the time phase difference using a fingertip plethysmogram larger means the presence of abnormality in an area toward a periphery (distal end), from which the presence of a cardiovascular disease can be estimated.

As described above, the measurement data on 2011, Feb. 2 was obtained at a point in time when Mr. Yoshito Fujita who had undergone surgery for removing part of bowel cancer showed recovery in this part. Meanwhile, it can be estimated that large dispersion in the vertical axis direction observed in each output result shows that Mr. Yoshito Fujita was still not in a perfect physical state. Comparing these output results makes it possible to estimate the presence of a cardiovascular disease more precisely.

Specifically, as described above, the amplitude of the fingertip initial contracting phase responsive wave (Pα wave) and the fingertip initial diastolic phase responsive wave (Pβ wave) obtained from an APW respectively correlate with the initial contracting phase positive wave (a wave) and the initial diastolic phase positive wave (e wave) of a fingertip plethysmogram extremely strongly, so that they can take the place of an a wave and an e wave as indexes. From this viewpoint, the time phase differences in the output results (1) and (2) obtained by comparison thereof are considered to be substantially the same. The time phase differences in the output results (3) and (4) obtained by comparison thereof are also considered to be substantially the same. Nevertheless, the aforementioned results show that there are differences therebetween. This means that comparing output results and determining whether a difference between time phase differences given in these output results is the same as or larger than a certain difference makes it possible to determine whether a person is in good health, specifically, whether the person suffers from cardiovascular abnormality or a different disease.

Thus, to obtain the aforementioned output results (1) to (4), it is preferable that the vascular information and time phase difference analyzing means 643 include means that plots coordinate points while using the wave height ratio (e/a value) of a fingertip plethysmogram and correlating this wave height ratio with the time phase difference using a fingertip plethysmogram (a–Eα or e–Eβ) and with the time phase difference only relating to an APW (Pα–Eα or Pβ–Eβ), and means that plots coordinate points while using the amplitude ratio relating to an APW (Eα/Eβ) and correlating this amplitude ratio with the time phase difference using a fingertip plethysmogram (a–Eα or e–Eβ) and with the time phase difference only relating to an APW (Pα–Eα or Pβ–Eβ). It is further preferable that the vascular information and time phase difference analyzing means 643 be configured so as to determine whether a difference between time phase differences in the output results is the same as or larger than a certain difference by comparing these output results.

Figure 49:
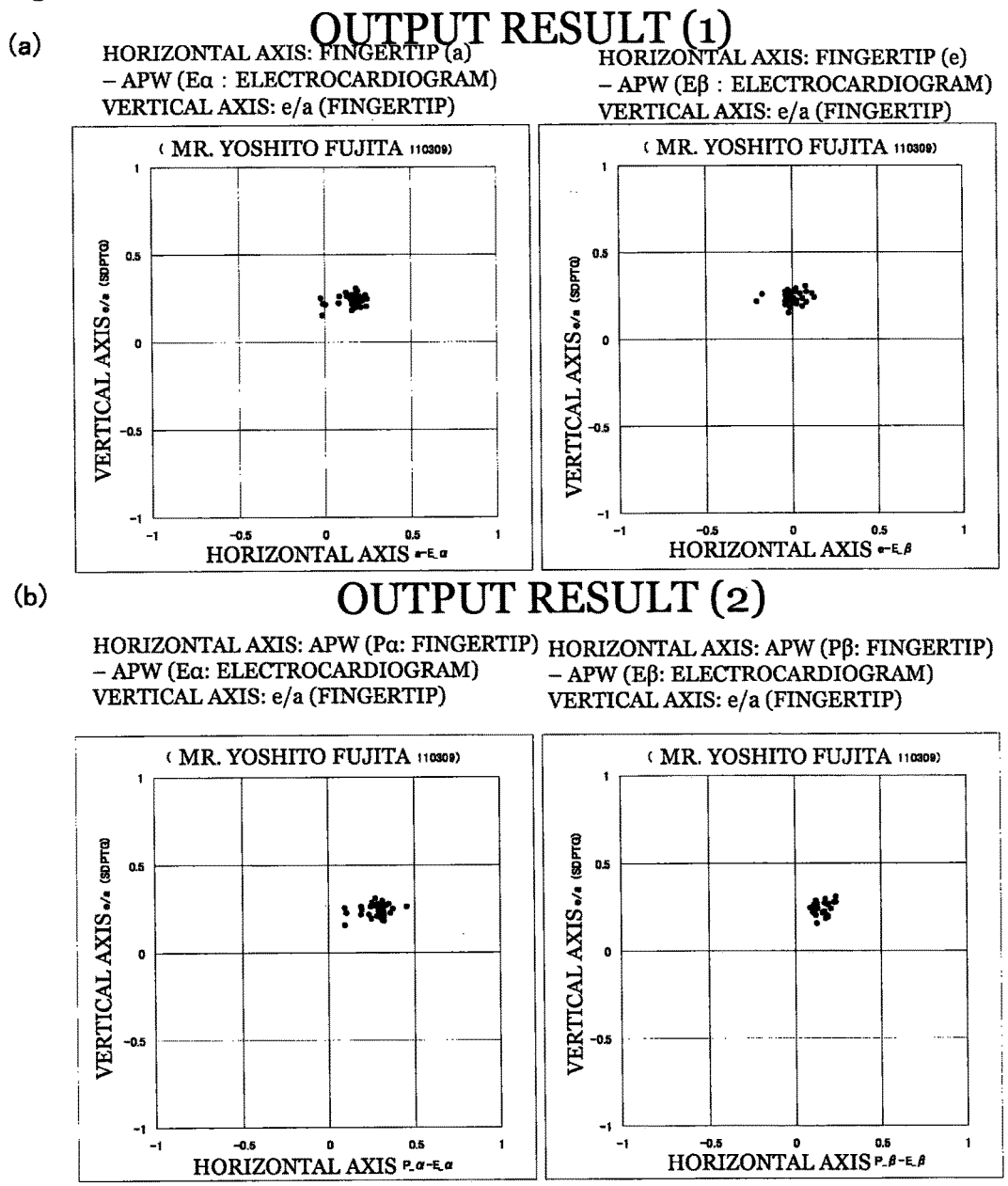
FIG. 49 shows output results (1) and (2) obtained by the vascular information and time phase difference analyzing means using data on 2011, Mar. 9 about the subject, Mr. Yoshito Fujita.

Different examples obtained by the aforementioned determination by the vascular information and time phase difference analyzing means 643 are described next. FIGS. 49 and 50 show output results about Mr. Yoshito Fujita obtained on 2011, Mar. 9. Each of comparison between the output results (1) and (2) of FIG. 49 and comparison between the output results (3) and (4) of FIG. 50 shows that there is still a difference between time phase differences but this difference is smaller than that of 2011, Feb. 2. This shows that Mr. Yoshito Fujita relaxed physically to show temporal tendency toward recovery of his physical state as a result of treatment for removing ascites and pleural effusion. The output results (1) and (2) of FIG. 49 show lower degrees of dispersions along the vertical axis. Meanwhile, the output results (3) and (4) of FIG. 50 show high degrees of dispersions along the vertical axis. This means that considering only the output results of FIG. 49 using the wave height ratio (e/a value) of the fingertip plethysmogram on the vertical axis results in determination that Mr. Yoshito Fujita was in a good health state seemingly. However, considering the output results of FIG. 50 for determination using the amplitude ratio (Eα/Eβ) of the APW on the vertical axis represents that degrees of dispersions are high, from which it can be estimated that abnormality was still present in a part near a central system. This also shows that the vascular information and time phase difference analyzing means 643 preferably includes the aforementioned two means for determination of a biological state in more detail.

Figure 52:
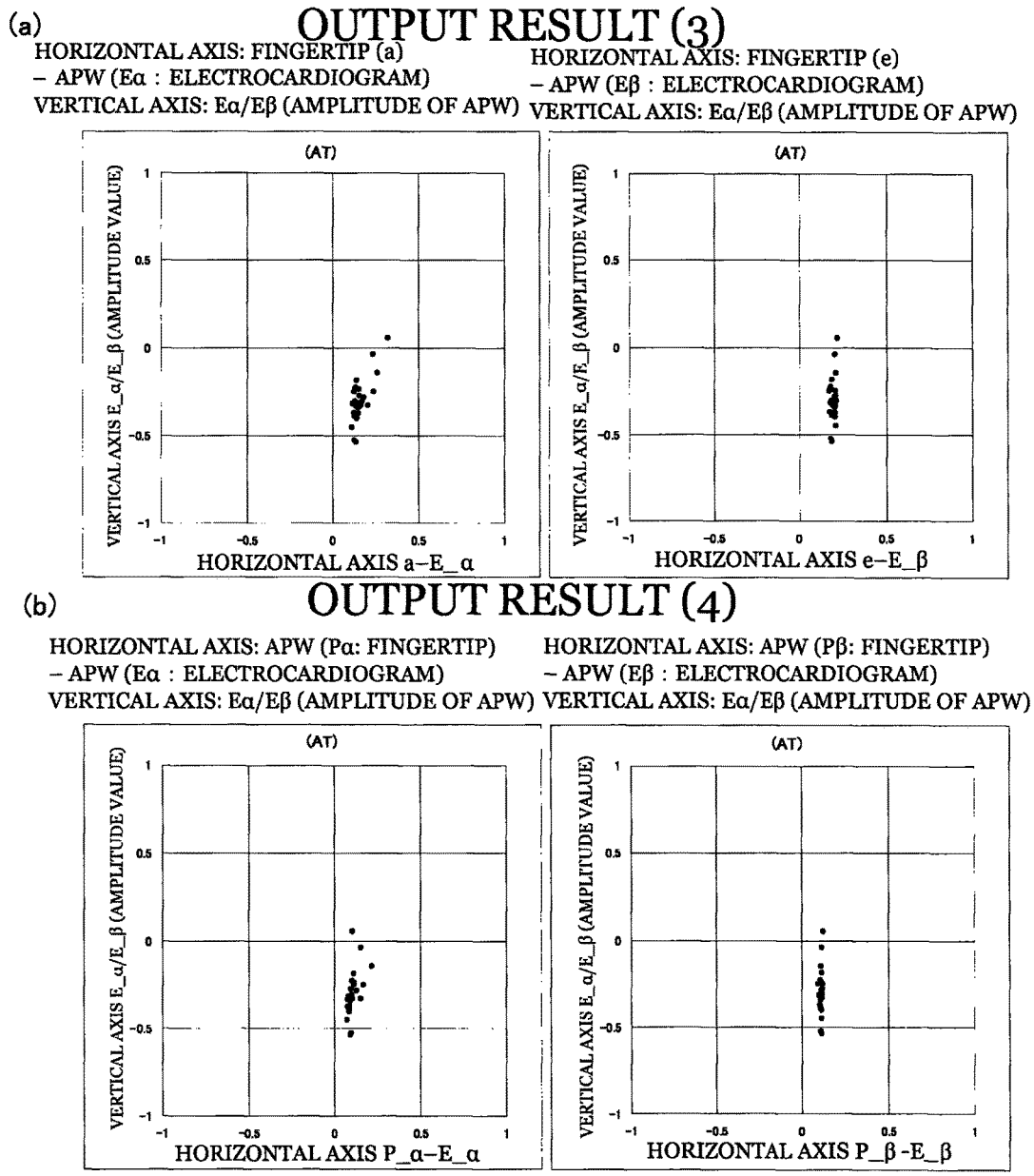

FIGS. 51 and 52 show output results about Mr. AT as a healthy male subject in his twenties. In the output results (1) and (2) of FIG. 51, time phase differences are small in these output results and degrees of dispersions are relatively low. This shows that Mr. AT is in good health. Meanwhile, in the output results (3) and (4) of FIG. 52, degrees of dispersions in the vertical axis direction are higher in both of these output results. Based on the output results (3) and (4) obtained by using the amplitude ratio relating to the APW (Eα/Eβ) on the vertical axis, the presence of some abnormality in a body trunk can be estimated. This subject declared voluntarily that he was in a state of tension during the experiment. The dispersions observed in the output results (3) and (4) are considered to result from this biological state. These results in FIGS. 51 and 52 also show that providing the aforementioned two means to the vascular information and time phase difference analyzing means 643 makes it possible to determine a biological state more precisely.

Figure 53:
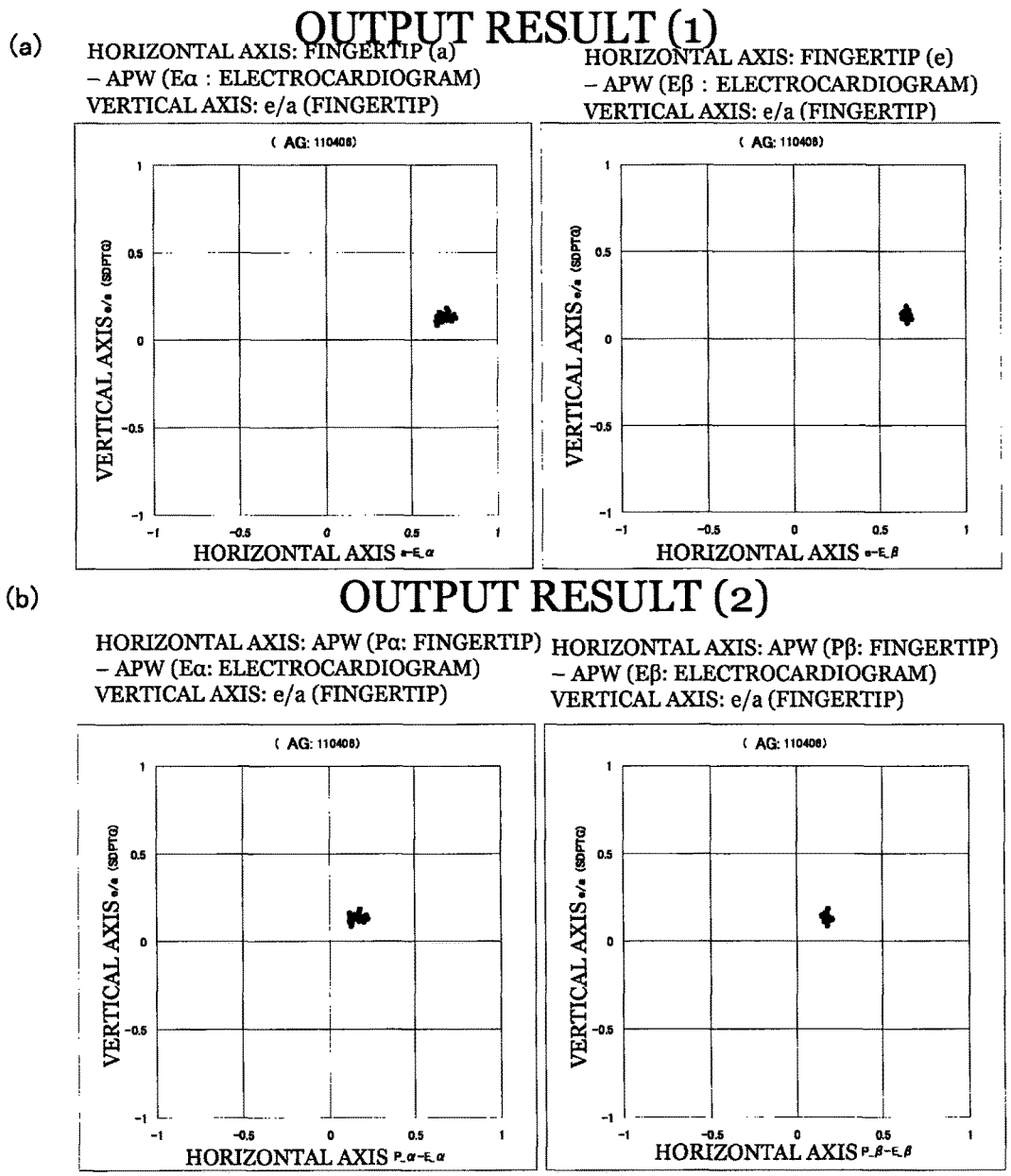
FIG. 53 shows output results (1) and (2) obtained by the vascular information and time phase difference analyzing means using data on 2011, Apr. 6 about a subject AG.
Figure 58:
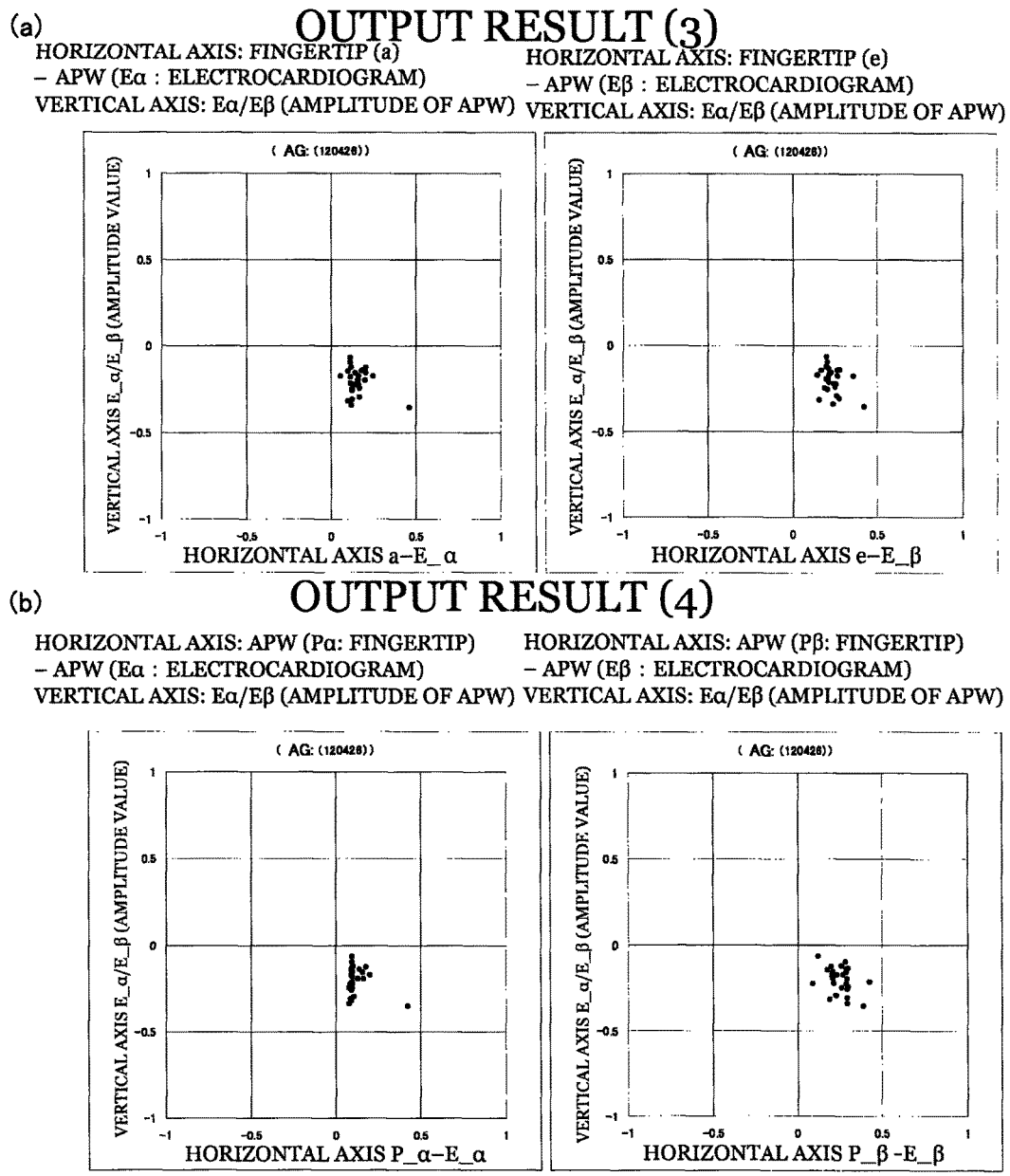
FIG. 58 shows output results (3) and (4) obtained by the vascular information and time phase difference analyzing means using the data on 2012, Apr. 26 about the subject AG.

FIGS. 53 to 58 show output results about Mr. AG as a male subject in his forties. FIGS. 53 and 54 show measurement results obtained on 2011, Apr. 6. FIGS. 55 and 56 show measurement results obtained on 2011, Aug. 23. FIGS. 57 and 58 show measurement results obtained on 2012, Apr. 26. The physical state of this subject, Mr. AG, changed suddenly on the following day of 2011, Aug. 23 and underwent surgery for a symptom of peritonitis.

The data on 2011, Apr. 6 shown in FIGS. 53 and 54 is referred to first. Regarding the output results (1) and (2), while tendency toward dispersion is not high, a large difference is observed between time phase differences in these output results. Regarding the output results (3) and (4), some dispersions are observed in the vertical axis direction, and a large difference is observed between time phase differences in these output results. This data about the subject, Mr. AG, shows that the time phase difference using a fingertip plethysmogram is larger, from which the presence of some abnormality can be estimated in an area from the center toward a periphery (distal end). However, Mr. AG declared voluntarily that he was healthy at the time of the experiment. This shows that even in the absence of a subjective symptom, a difference between time phase differences in corresponding output results still appears and this shows some abnormality in a body.

It can be understood from the data on 2011, Aug. 23 that there is a large difference between time phase differences in the output results (1) and (2) of FIG. 55 and between time phase differences in the output results (3) and (4) of FIG. 56, meaning the presence of abnormality in a body. Meanwhile, regarding the output results (3) and (4) of FIG. 56 using the amplitude ratio (Eα/ER) of the APW on the vertical axis, dispersions to high degrees are observed in the vertical axis direction, from which the presence of some abnormality in a body trunk can be estimated.

The data on 2012, Apr. 26 was obtained at a point in time after elapse of a little over seven months after the surgery for peritonitis. Comparison between the output results (1) and (2) in FIG. 57 shows that there is substantially no difference between time phase differences in these output results and degrees of dispersions are relatively low. Comparison between the output results (3) and (4) in FIG. 58 also shows that there is substantially no difference between time phase differences in these output results whereas slight tendencies toward dispersion are observed. Each comparison shows that there is substantially no difference between the time phase differences. Further, in each output result, a degree of a one-dimensional dispersion is not so high in the vertical axis direction. Thus, it can be estimated that there is no abnormality in an area from a body trunk toward a distal end. Dispersions to some degrees are observed in the output results (3) and (4) in FIG. 58. These dispersions exhibit substantially circular patterns rather than vertically-long dispersions in the vertical axis direction. Thus, these dispersions are considered to be chaotic dispersions resulting from a highly relaxed psychosomatic state and not to be dispersions resulting from a factor relating to a disease or tension.

As described above, the data about the subject, Mr. AG who actually underwent the surgery shows that abnormality in a physical state can be estimated as early as in a stage without a subjective symptom, not to mention a state with a subjective symptom. The output results (1) to (4) obtained when Mr. AG was in a stable physical state after the surgery include no sign of abnormality. This shows that a state determined by the combination of the multiple means of the vascular information and time phase difference analyzing means 643 has a higher degree of precision.

A technique employed by the time phase difference analyzing means 642 or the vascular information and time phase difference analyzing means 643 of the state analyzing means 64 to determine a degree of dispersion or convergence of coordinate points is not limited. As an example, the following technique is applicable. Squares (cells) of a given area are arranged for example lengthwise and crosswise in each event of a coordinate and the number of cells is determined where coordinate points are distributed. By determining change in this number of cells per unit time, trend in the change of coordinate points can be determined that indicates whether the coordinate points tend to be dispersed or converge. Not only by grasping change in the number of cells in a time-series manner but also by making slide calculation conducted by making overlaps in a lap time of 90% and the like to consider the change in the number of cells, the condition of dispersion or convergence can be understood in more fragments. As a result, change in a biological state can be analyzed more finely.

In the aforementioned embodiments, a fingertip plethysmogram meter is used as the peripheral trunk biological signal measuring device and a fingertip plethysmogram is used as a peripheral biological signal. These are given not for limitation. A peripheral biological signal to be used can also be the pulse wave of a part where a pulse can be detected relatively easily such as superficial temporal carotid, a carotid artery, a subclavian artery, a brachial artery, a radial artery, an ulnar artery, a femoral artery, a popliteal artery, a posterior tibial artery, or a dorsalis pedis artery. In the case of bowel cancer, for example, the pulse of a femoral artery exhibits a larger time phase shift from an APW than a fingertip plethysmogram. Thus, in this case, by comparing the time phase of the APW and that of the pulse of the femoral artery, the presence of some factor of a disease such as bowel cancer can be determined in a range from a position including a lumber, a heart and its vicinity where the body trunk biological signal measuring device to measure an APW is attached toward a femoral area. A factor of a disease can be specified more precisely by measuring peripheral biological signals simultaneously at multiple places including the aforementioned fingertip, carotid artery, radial artery and femoral artery, comparing these multiple peripheral biological signals with an APW, and comparing the respective time phase differences.

INDUSTRIAL APPLICABILITY

This invention can also be used as a simple screening device for a health state by implementing this invention while attaching the body trunk biological signal measuring device 1 to a sleeping tool such as a bed and measuring a biological signal using the peripheral biological signal measuring device together with the body trunk biological signal measuring device 1, or by implementing this invention while installing the body trunk biological signal measuring device 1 on a chair and measuring a biological signal. Alternatively, by attaching the body trunk biological signal measuring device 1 to a seat of a vehicle such as an automobile, this invention can also be used as a device to analyze the health state of a driver or that of a person in the vehicle.

REFERENCE SIGNS LIST

1 Body trunk biological signal measuring device
60 Biological state analyzer
61 Body trunk second derivative waveform calculating means
62 Maximum amplitude waveform component specifying means
621 First maximum amplitude waveform component specifying means
622 Second maximum amplitude waveform component specifying means
63 Inflection point specifying means
64 State analyzing means
641 Original waveform comparing and analyzing means
642 Time phase difference analyzing means
643 Vascular information and time phase difference analyzing means

The invention claimed is:
1. A biological state analyzer comprising:
processing circuitry configured to
second differentiate a time-series waveform of a body trunk biological signal extracted from a back of a body trunk of a body by a body trunk biological signal measuring device to obtain a second derivative waveform of the body trunk biological signal in a time-series manner;
specify a maximum amplitude waveform component, which is a waveform component of a maximum amplitude of a low frequency appearing as a result of switch of an amplitude from attenuation to amplification in transition from a contracting phase to a diastolic phase of a ventricle, using a reference form of the second derivative waveform of the body trunk biological signal, the maximum amplitude waveform component being specified in each period of the second derivative waveform of the body trunk biological signal;
specify an inflection point where an amplitude switches from attenuation to amplification as a ventricle initial contracting phase responsive wave (Eα wave), and specify an inflection point where the amplitude switches from amplification to attenuation as a ventricle initial diastolic phase responsive wave (Eβ wave), the ventricle initial contracting phase responsive wave (Eα wave) and the ventricle initial diastolic phase responsive wave (Eβ wave) being arranged in this order along the temporal axis with the maximum amplitude waveform component placed in therebetween;
second differentiate a time-series waveform of a peripheral biological signal extracted from a periphery of the body by a peripheral biological signal measuring device to obtain a second derivative waveform of the peripheral biological signal in a time-series manner;
analyze a biological state of the body, using an initial contracting phase positive wave (a wave) and an initial diastolic phase positive wave (e wave) of the peripheral biological signal obtained from the second derivative waveform of the peripheral biological signal, and using the ventricle initial contracting phase responsive wave (Eα wave) and the ventricle initial diastolic phase responsive wave (Eβ wave); and
output an analysis result of the biological state of the body,
wherein the processing circuitry is further configured to analyze a state of a sympathetic nervous system using a time phase difference of heart-to-fingertip propagation time (a–Eα) between the initial contracting phase positive wave (a wave) of the peripheral biological signal and the ventricle initial contracting phase responsive wave (Eα wave) of the body trunk biological signal, and using a time phase difference of heart-to-fingertip propagation time (e–Eβ) between the initial diastolic phase positive wave (e wave) of the peripheral biological signal and the ventricle initial diastolic phase responsive wave (Eβ wave) of the body trunk biological signal,
wherein the processing circuitry is further configured to analyze the biological state by using a relation between vascular information and information about the sympathetic nervous system represented by at least one of the time differences a–Eα or e–Eβ,
wherein by using, as the vascular information, a wave height ratio (e/a value) between the initial contracting phase positive wave (a wave) and the initial diastolic phase positive wave (e wave) of the time-series waveform of the peripheral biological signal, the processing circuitry is further configured to
plot the wave height ratio e/a versus the time phase difference (a–Eα) or the time phase difference (e–Eβ), and analyze the biological state based on the plot of the e/a ratio versus the difference a–Eα or e–Eβ, thereby estimating a state of stress including a presence or absence of cardiovascular abnormality, without using a stethoscope or a measuring instrument for measuring of heart sound or an electrocardiogram.

2. The biological state analyzer according to claim 1, wherein the processing circuitry is further configured to analyze a biological state by comparing the time-series waveform of the body trunk biological signal and the time-series waveform of the peripheral biological signal.

3. The biological state analyzer according to claim 2, wherein the processing circuitry is further configured to determine the presence or absence of cardiovascular abnormality by comparing the time-series waveform of the body trunk biological signal and the time-series waveform of the peripheral biological signal in frequency and amplitude.

4. A non-transitory computer readable medium including executable instructions, which when executed by a computer cause the computer to:

second differentiate a time-series waveform of a body trunk biological signal extracted from a back of a body trunk of a body by a body trunk biological signal measuring device to obtain a second derivative waveform of the body trunk biological signal in a time-series manner;

specify a maximum amplitude waveform component, which is a waveform component of a maximum amplitude of a low frequency appearing as a result of switch of an amplitude from attenuation to amplification in transition from a contracting phase to a diastolic phase of a ventricle, using a reference form of the second derivative waveform of the body trunk biological signal, the maximum amplitude waveform component being specified in each period of the second derivative waveform of the body trunk biological signal;

specify an inflection point where an amplitude switches from attenuation to amplification as a ventricle initial contracting phase responsive wave (Eα wave), and specify an inflection point where the amplitude switches from amplification to attenuation as a ventricle initial diastolic phase responsive wave (Eβ wave), the ventricle initial contracting phase responsive wave (Eα wave) and the ventricle initial diastolic phase responsive wave (Eβ wave) being arranged in this order along the temporal axis with the maximum amplitude waveform component placed in therebetween;

second differentiate a time-series waveform of a peripheral biological signal extracted from a periphery of the body by a peripheral biological signal measuring device to obtain a second derivative waveform of the peripheral biological signal in a time-series manner;

analyze a biological state of the body, using an initial contracting phase positive wave (a wave) and an initial diastolic phase positive wave (e wave) of the peripheral biological signal obtained from the second derivative waveform of the peripheral biological signal, and using the ventricle initial contracting phase responsive wave (Eα wave) and the ventricle initial diastolic phase responsive wave (Eβ wave); and output an analysis result of the biological state of the body, wherein the instructions, when executed, further cause the computer to:

analyze a state of a sympathetic nervous system using a time phase difference of heart-to-fingertip propagation time (a–Eα) between the initial contracting phase positive wave (a wave) of the peripheral biological signal and the ventricle initial contracting phase responsive wave (Eα wave) of the body trunk biological signal, and using a time phase difference of heart-to-fingertip propagation time (e–Eβ) between the initial diastolic phase positive wave (e wave) of the peripheral biological signal and the ventricle initial diastolic phase responsive wave (Eβ wave) of the body trunk biological signal, analyze the biological state by using a relation between vascular information and information about the sympathetic nervous system represented by at least one of the time differences a–Eα or e–Eβ, the vascular information being, a wave height ratio (e/a value) between the initial contracting phase positive wave (a wave) and the initial diastolic phase positive wave (e wave) of the time-series waveform of the peripheral biological signal, plot the wave height ratio e/a versus the time phase difference (a–Eα) or the time phase difference (e–Eβ), and analyze the biological state based on the plot of the e/a ratio versus the difference a–Eα or e–Eβ, thereby estimating a state of stress including a presence or absence of cardiovascular abnormality, without using a stethoscope or a measuring instrument for measuring of heart sound or an electrocardiogram.

5. The non-transitory computer readable medium according to claim 4, wherein the instructions, when executed, further cause the computer to analyze a biological state by comparing the time-series waveform of the body trunk biological signal and the time-series waveform of the peripheral biological signal.

6. The non-transitory computer readable medium according to claim 5, wherein the instructions, when executed, further cause the computer to determine the presence or absence of cardiovascular abnormality by comparing the time-series waveform of the body trunk biological signal and the time-series waveform of the peripheral biological signal in frequency and amplitude.

* * * * *